US007595305B2

(12) United States Patent
Agrawal et al.

(10) Patent No.: US 7,595,305 B2
(45) Date of Patent: Sep. 29, 2009

(54) MODULATION OF IMMUNOSTIMULATORY PROPERTIES OF OLIGONUCLEOTIDE-BASED COMPOUNDS BY UTILIZING MODIFIED IMMUNOSTIMULATORY DINUCLEOTIDES

(75) Inventors: Sudhir Agrawal, Shrewsbury, MA (US); Lakshmi Bhagat, Framingham, MA (US); Dong Yu, Westboro, MA (US); Ekambar Kandimalla, Southboro, MA (US)

(73) Assignee: Idera Pharmaceuticals, Cambridge, MA (US)

( * ) Notice: Subject to any disclaimer, the term of this patent is extended or adjusted under 35 U.S.C. 154(b) by 140 days.

(21) Appl. No.: 11/173,794

(22) Filed: Jul. 1, 2005

(65) Prior Publication Data
US 2006/0287261 A1    Dec. 21, 2006

Related U.S. Application Data

(63) Continuation of application No. 10/757,345, filed on Jan. 14, 2004.

(60) Provisional application No. 60/440,587, filed on Jan. 16, 2003.

(51) Int. Cl.
*C07H 21/02* (2006.01)
*C07H 21/04* (2006.01)
*A01N 43/04* (2006.01)
*A61K 31/70* (2006.01)

(52) U.S. Cl. ............................ 514/44; 514/45; 536/23.1

(58) Field of Classification Search ........................ None
See application file for complete search history.

(56) References Cited

U.S. PATENT DOCUMENTS

| | | | |
|---|---|---|---|
| 5,149,798 A | 9/1992 | Agrawal et al. | |
| 5,366,878 A | 11/1994 | Pederson et al. | |
| 5,594,121 A | 1/1997 | Froehler et al. | |
| 5,635,377 A | 6/1997 | Pederson et al. | |
| 5,652,355 A | 7/1997 | Metelev et al. | |
| 5,912,332 A | 6/1999 | Agrawal et al. | |
| 6,143,881 A | 11/2000 | Metelev et al. | |
| 6,346,614 B1 | 2/2002 | Metelev et al. | |
| 2004/0097719 A1* | 5/2004 | Agrawal et al. | 536/23.2 |
| 2004/0156825 A1* | 8/2004 | Agrawal et al. | 424/93.2 |
| 2004/0266709 A1* | 12/2004 | Kandimalla et al. | 514/44 |
| 2004/0266710 A1* | 12/2004 | Kandimalla et al. | 514/44 |
| 2005/0026861 A1* | 2/2005 | Kandimalla et al. | 514/44 |
| 2006/0014713 A1* | 1/2006 | Agrawal et al. | 514/44 |
| 2006/0019909 A1* | 1/2006 | Agrawal et al. | 514/44 |
| 2006/0142224 A1* | 6/2006 | Kandimalla et al. | 514/44 |

FOREIGN PATENT DOCUMENTS

| | | |
|---|---|---|
| WO | WO 98/49288 | 11/1998 |
| WO | WO 01/12804 | 2/2001 |
| WO | PCT/US01/13682 | 4/2001 |
| WO | WO 01/55370 | 8/2001 |
| WO | PCT/US01/30137 | 9/2001 |

OTHER PUBLICATIONS

Kandimalla et al, Bioconjugate Chem. 13, 966-974, 2002.*
Kandimalla et al, Nucleic Acid Research vol. 31, No. 9, 2003.*
Kandimalla et al, PNAS 100(24): 14303-14308, 2003.*
Donnelly et al, Nature Medicine, 9(11):1354-1356, 2003.*
DeGruijl et al, Nature Medicine, 5110: 1124-1125, 1999.*
Bitton R. J., Current Opinion in Molecular Therapeutics 611: 17-26, 2004; Abstract only.*
Weiner, J. Leukoc. Biol. 68: 455-463, 2000.*
Krieg et al, Pharmacol. & Therap. 84: 113-120, 1999.*
Ballas et al, J. lmmunol. 167: 4878-4886, 2001.*
Agrawal et al, Trends in Molecular Medicine 8(3): 114-121, 2002.*
Wooldridge et al, Blood 89(8):2994-2998, 1997.*
Baral et al, Cancer Immunol. Immunother. 52(3):317-327, 2003.*
van Ojik et al, Cancer Research 63(17):5595-5600, 2003.*
Souza et al, Clin. and Diag. Lab. lmmunol. 7(2): 175-181, 2000.*
Agrawal et al, Curr. Cancer Drug Targets 1: 197-209, 2001.*
Decker et al, Blood 99(4): 1320-1326, 2002.*
Souza et al, Clin. and Diag. Lab. Immunol. 7(2): 175-181, 2000.*
Kandimalla et al, PNAS 102(19):6925-6930, 2005.*
U.S. Appl. No. 10/757,345, by Sudhir Agrawal, Lakshmi Bhagat, Dong Yu and Ekambar Kandimalla, filed Jan. 14, 2004.
U.S. Appl. No. 11/173,938, by Sudhir Agrawal, Lakshmi Bhagat, Dong Yu and Ekambar Kandimalla, filed Jul. 1, 2005.
U.S. Appl. No. 11/174,002, by Sudhir Agrawal, Lakshmi Bhagat, Dong Yu and Ekambar Kandimalla, filed Jul. 1, 2005.
Agrawal et al., Meth. in Mol. Biol., "Protocols for Oligonucleotides and Analogs", 20:165-189, 1993.
Oligonucleotides and Analogues, A Practical approach, 87-108 (F. Eckstein, ed., 1991).
Khorana et al., J. Mol. Bio., 72:209 (1972).Reese, Tetrahedron lett., 34:3143 3179 (1978).
Beaucage et al., Tetrahedron lett., 22:1859-1862 (1981).
Agrawal et al., Tetrahedron lett., 28:3539-3542 (1987).
Connolly et al., Biochem., 23:3443 (1984).

(Continued)

*Primary Examiner*—Q. Janice Li
*Assistant Examiner*—Kevin K. Hill
(74) *Attorney, Agent, or Firm*—Wayne A. Keown; Joseph C. Zucchero; Keown & Zucchero LLP

(57) ABSTRACT

The invention relates to the therapeutic use of oligonucleotides as immunostimulatory agents in immunotherapy applications. More particularly, the invention provides immunomers and an immunostimulatory oligonucleotides for use in methods for generating an immune response or for treating a patient in need of immunostimulation. The immunomers and an immunostimulatory oligonucleotides of the invention preferably comprise novel purines. The immunomers according to the invention further comprise at least two oligonucleotides linked at their 3' ends, internucleoside linkages or functionalized nucleobase or sugar to a non-nucleotidic linker, at least one of the oligonucleotides being an immunomodulatory oligonucleotide and having an accessible 5' end.

7 Claims, 30 Drawing Sheets

OTHER PUBLICATIONS

Jager et al., Biochem., 27:7237 (1988).
Agrawal et al., Proc. Natl. Acad. Sci. (USA), 85:7079-7082 (1988).
Kuramoto et al., Jpn. J. Cancer Res., 83:1128-1131 (1992).
Krieg et al., nature, 371:546-549 (1995).
Liang et al., J. Clin. Invest., 98:1119-1129 (1996).
Moldoveanu et al., Vaccine, 16:1216-124 (1998).
McCluskie et al., J. Immunol., 161:4463-4466 (1998).
Hartman et al., J. Immunol., 164:1617-1624 (2000).
Zhao et al., Biocehm. Pharmacol., 51:173-182 (1996).
Zhao et al., Biochem. Pharmacol., 52:1537-1544 (1996).
Zhao et al., Antisense Nucleic Acid Drug Dev., 7:495-502 (1997).
Zhao et al., Bioorg. Med. Chem. Lett., 9:3453-3458 (1999).
Zhao et al., Bioorg. Med. Chem. Lett., 10:1051-1054 (2000).
Yu et al., Bioorg. Med. Chem. Lett., 10:2585-2588 (2000).
Yu et al., Bioorg. Med. Chem. Lett., 11:2263-2267 (2001).
Kandimalla et al., Bioorg. Med. Chem., 9:807-813 (2001).
Noronha et al., Biocehm., 39:7050-7062 (2000).

* cited by examiner

Linkers for linear synthesis

Parallel Synthesis of Immunomers

Figure 7
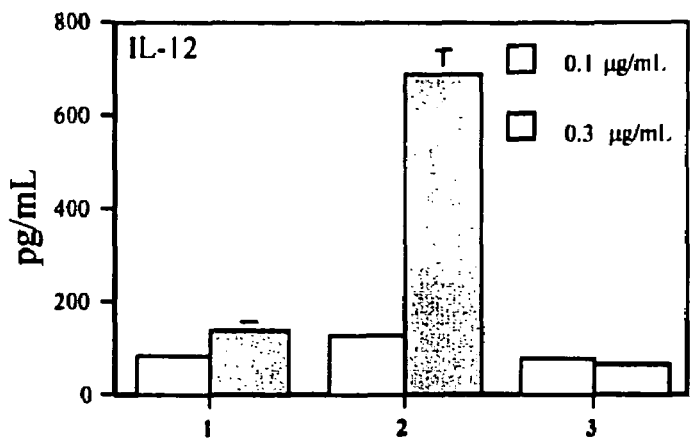
Figure 7A
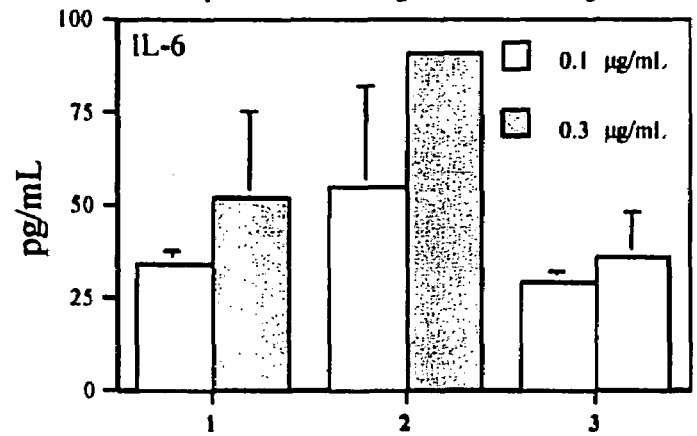
Figure 7B
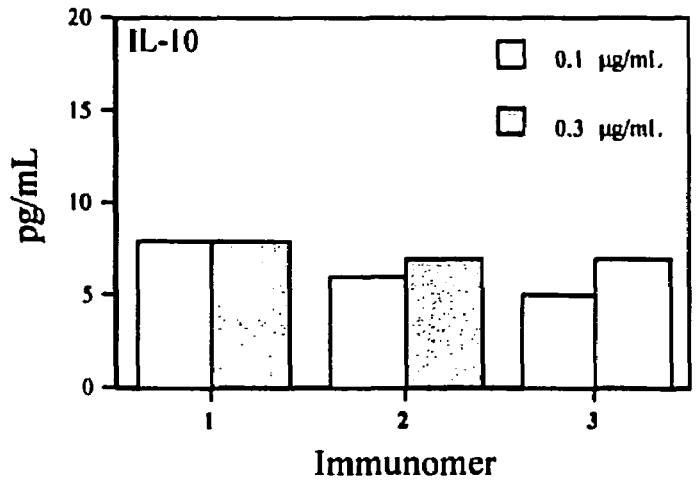
Figure 7C

Figure 8.
Figure 8A
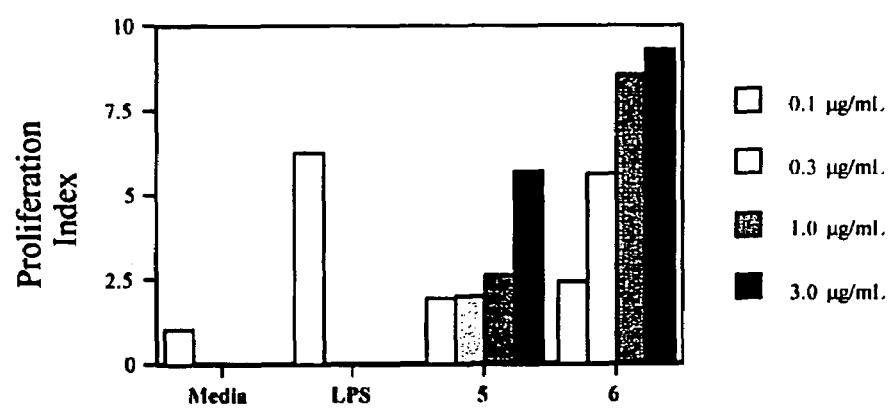
Figure 8B
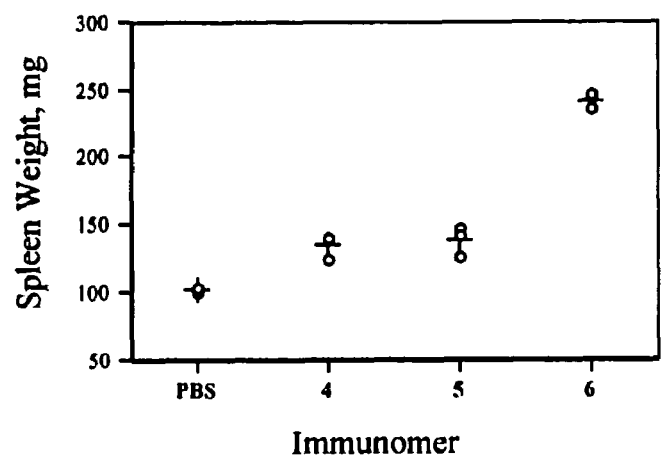

Figure 9.
Figure 9A
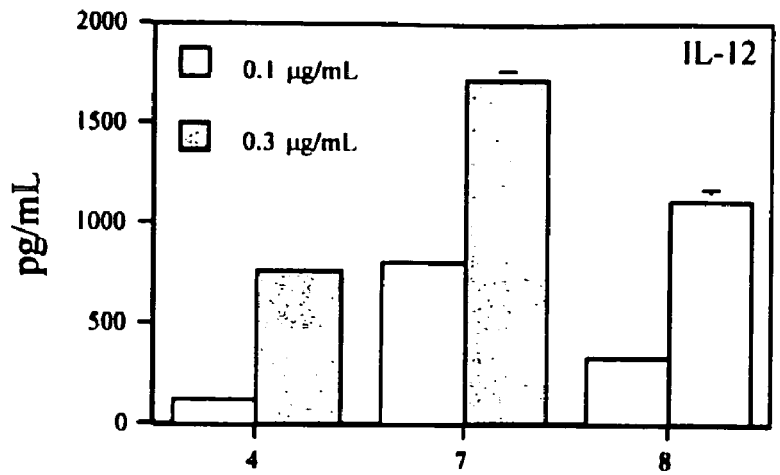
Figure 9B
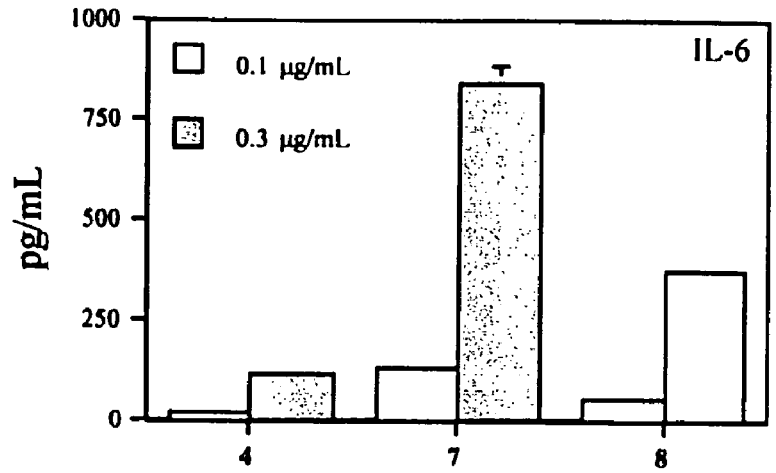
Figure 9C
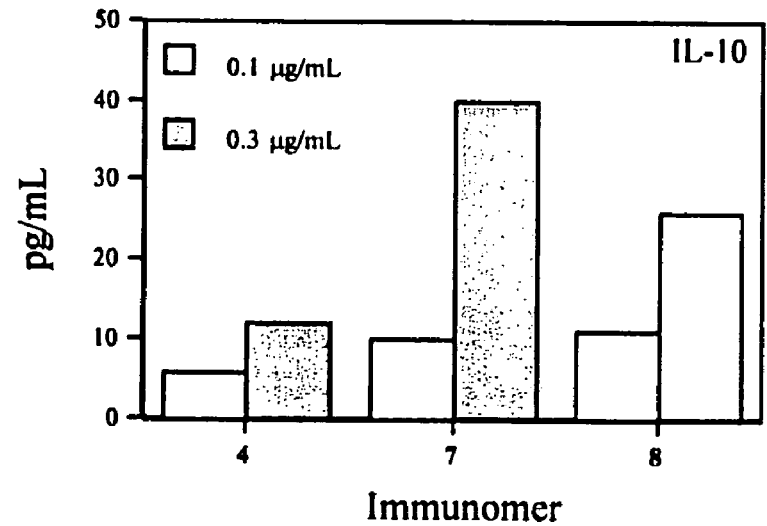

Figure 10.
Figure 10A
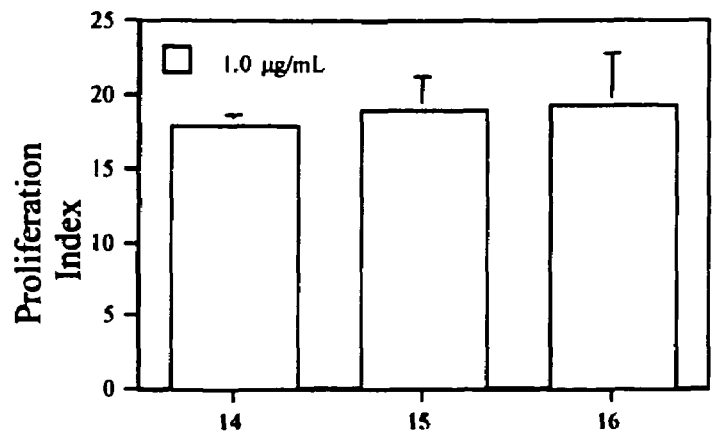
Figure 10B
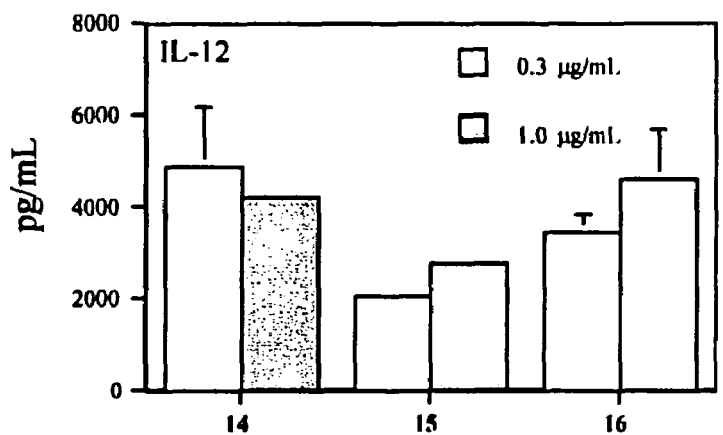
Figure 10C
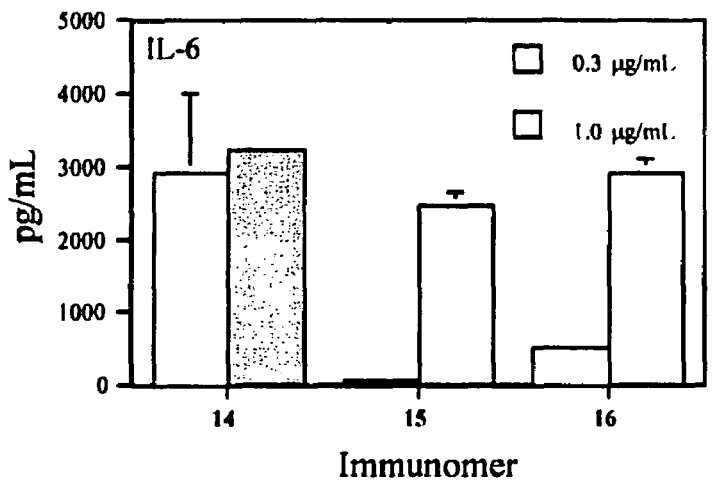

Figure 11.
Figure 11A
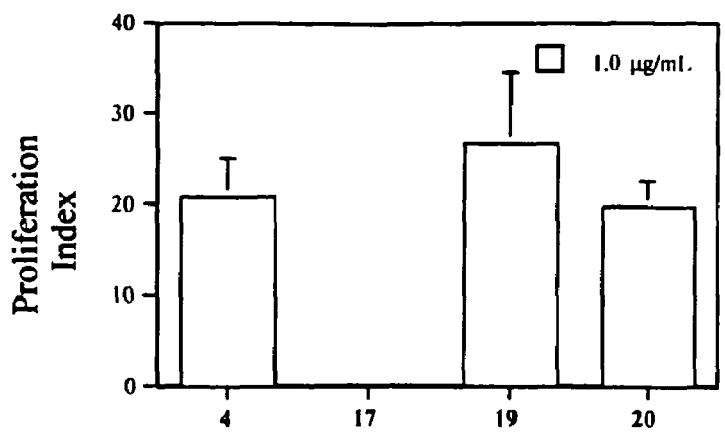
Figure 11B
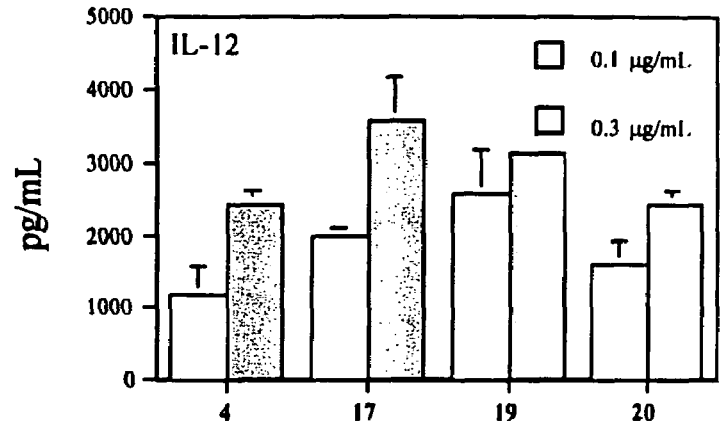
Figure 11C
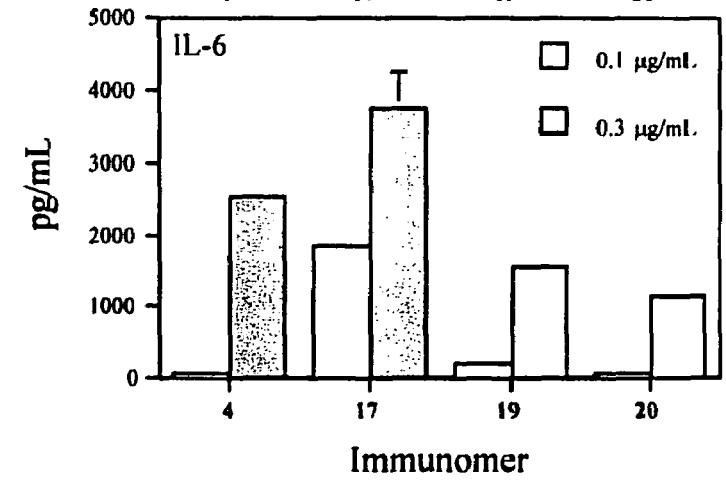

Some pyrimidine and purine structures

2-Oxy-4-amino pyrimidine or cytosine

2-Amino-6-oxy-purine or Guanine    2-Amino-6-oxy-7-deaza-purine    2-Oxy-7-deaza-8-methyl purine
                                    or 7-Deaza-guanine

| | |
|---|---|
| 4 | d(5'-CTATCTGA<u>CG</u>TTCTCTGT-3') |
| 189 | d(5'-CTATCTGA<u>RG</u>TTCTCTGT-3') |
| 10 | d(5'-CTATCTGA<u>CR</u>TTCTCTGT-3') |
| 25 | d(5'-CTATCTGT<u>CG</u>TTCTCTGT-3') |
| 190 | d(5'-CTATCTGT<u>RG</u>TTCTCTGT-3') |
| 191 | d(5'-TCTGA<u>RG</u>TTCT-L-TCTTG<u>RA</u>GTCT-5') |
| 192 | d(5'-TCTGT<u>RG</u>TTCT-L-TCTTG<u>R</u>TGTCT-5') |

Comparison of Natural Pyrimidine-Purine Immunostimulatory Motif and Synthetic-Purine-Guanine Immunostimulatory Motif (RpG)

CpG

RpG

Immunostimulatory activity of parent oligonucleotide 1 containing CpG dinucleotide motif, oligonucleotide 2 containing RpG dinucleotide motif and control oligonucleotide 3 containing GpR dinucleotide motif in mouse spleen cell culture assays. All sequences contain mouse-specific immunostimulatory motif (GACGTT).

Immunostimulatory activity of parent oligonucleotide 4 containing CpG dinucleotide motif, and oligonucleotide 5 containing RpG dinucleotide motif in mouse spleen cell culture assays. All sequences contain human-specific immunostimulatory motif (GTCGTT).

Immunostimulatory activity of parent oligonucleotides 1 and 4 containing CpG dinucleotide motif, and immunomers 6 and 7 containing RpG dinucleotide motif in mouse spleen cell culture assays. Sequences 1 and 6 contain mouse-specific immunostimulatory motif (GACGTT) and sequences 4 and 7 contain human-specific immunostimulatory motif (GTCGTT).

Immunostimulatory activity of parent oligonucleotides 1 and 4 containing CpG dinucleotide motif, and immunomers 6 and 7 containing RpG dinucleotide motif in J774, macrophage-like cell culture assays. Sequences 1 and 6 contain mouse-specific immunostimulatory motif (GACGTT) and sequences 4 and 7 contain human-specific immunostimulatory motif (GTCGTT).

Activation of NF-κB and degradation of Iκ-Bα in J774 cells as a measure of immunostimulatory activity of parent oligonucleotides 1 - 7.

Immunostimulatory activity of immunomer 7 human PBMC cultures (one donor) at 10 µg/mL concentration.

MODULATION OF IMMUNOSTIMULATORY PROPERTIES OF OLIGONUCLEOTIDE-BASED COMPOUNDS BY UTILIZING MODIFIED IMMUNOSTIMULATORY DINUCLEOTIDES

RELATED APPLICATIONS

This Application claims priority to U.S. patent application Ser. No. 10/757,345, filed Jan. 14, 2004, which claims the benefit of U.S. Provisional Application 60/440,587, filed Jan. 16, 2003. The entire teachings of the above-referenced Applications are incorporated herein by reference.

BACKGROUND OF THE INVENTION

1. Field of the Invention

The invention relates to immunology and immunotherapy applications using oligonucleotides as immunostimulatory agents.

2. Summary of the Related Art

Oligonucleotides have become indispensable tools in modern molecular biology, being used in a wide variety of techniques, ranging from diagnostic probing methods to PCR to antisense inhibition of gene expression and immunotherapy applications. This widespread use of oligonucleotides has led to an increasing demand for rapid, inexpensive and efficient methods for synthesizing oligonucleotides.

The synthesis of oligonucleotides for antisense and diagnostic applications can now be routinely accomplished. See, e.g., *Methods in Molecular Biology*, Vol. 20: *Protocols for Oligonucleotides and Analogs* pp. 165-189 (S. Agrawal, ed., Humana Press, 1993); *Oligonucleotides and Analogues, A Practical Approach*, pp. 87-108 (F. Eckstein, ed., 1991); and Uhlmann and Peyman, supra; Agrawal and Iyer, *Curr. Op. in Biotech.* 6:12 (1995); and *Antisense Research and Applications* (Crooke and Lebleu, eds., CRC Press, Boca Raton, 1993). Early synthetic approaches included phosphodiester and phosphotriester chemistries. For example, Khorana et al., *J. Molec. Biol.* 72:209 (1972) discloses phosphodiester chemistry for oligonucleotide synthesis. Reese, *Tetrahedron Lett.* 34:3143-3179 (1978), discloses phosphotriester chemistry for synthesis of oligonucleotides and polynucleotides. These early approaches have largely given way to the more efficient phosphoramidite and H-phosphonate approaches to synthesis. For example, Beaucage and Caruthers, *Tetrahedron Lett.* 22:1859-1862 (1981), discloses the use of deoxyribonucleoside phosphoramidites in polynucleotide synthesis. Agrawal and Zamecnik, U.S. Pat. No. 5,149,798 (1992), discloses optimized synthesis of oligonucleotides by the H-phosphonate approach. Both of these modern approaches have been used to synthesize oligonucleotides having a variety of modified internucleotide linkages. Agrawal and Goodchild, *Tetrahedron Lett.* 28:3539-3542 (1987), teaches synthesis of oligonucleotide methylphosphonates using phosphoramidite chemistry. Connolly et al., *Biochem.* 23:3443 (1984), discloses synthesis of oligonucleotide phosphorothioates using phosphoramidite chemistry. Jager et al., *Biochem.* 27:7237 (1988), discloses synthesis of oligonucleotide phosphoramidates using phosphoramidite chemistry. Agrawal et al., *Proc. Natl. Acad. Sci.* (*USA*) 85:7079-7083 (1988), discloses synthesis of oligonucleotide phosphoramidates and phosphorothioates using H-phosphonate chemistry.

More recently, several researchers have demonstrated the validity of the use of oligonucleotides as immunostimulatory agents in immunotherapy applications. The observation that phosphodiester and phosphorothioate oligonucleotides can induce immune stimulation has created interest in developing this side effect as a therapeutic tool. These efforts have focused on phosphorothioate oligonucleotides containing the dinucleotide natural CpG. Kuramoto et al., *Jpn. J. Cancer Res.* 83:1128-1131 (1992) teaches that phosphodiester oligonucleotides containing a palindrome that includes a CpG dinucleotide can induce interferon-alpha and gamma synthesis and enhance natural killer activity. Krieg et al., *Nature* 371:546-549 (1995) discloses that phosphorothioate CpG-containing oligonucleotides are immunostimulatory. Liang et al., *J. Clin. Invest.* 98:1119-1129 (1996) discloses that such oligonucleotides activate human B cells. Moldoveanu et al., *Vaccine* 16:1216-124 (1998) teaches that CpG-containing phosphorothioate oligonucleotides enhance immune response against influenza virus. McCluskie and Davis, *J. Immunol.* 161:4463-4466 (1998) teaches that CpG-containing oligonucleotides act as potent adjuvants, enhancing immune response against hepatitis B surface antigen. Hartman et al., J. Immunol 164: 1617-1624 (2000) teaches that the immunostimulatory sequence is species specific, and different between mice and primates.

Other modifications of CpG-containing phosphorothioate oligonucleotides can also affect their ability to act as modulators of immune response. See, e.g., Zhao et al., *Biochem. Pharmacol.* (1996) 51:173-182; Zhao et al., *Biochem Pharmacol.* (1996) 52:1537-1544; Zhao et al., *Antisense Nucleic Acid Drug Dev.* (1997) 7:495-502; Zhao et al., *Bioorg. Med. Chem. Lett.* (1999) 9:3453-3458; Zhao et al., *Bioorg Med. Chem. Lett.* (2000) 10:1051-1054; Yu et al., *Bioorg. Med. Chem. Lett.* (2000) 10:2585-2588; Yu et al., *Bioorg. Med. Chem. Lett.* (2001) 11:2263-2267; and Kandimalla et al., *Bioorg. Med. Chem.* (2001) 9:807-813.

These reports make clear that there remains a need to be able to modulate the immune response caused by immunostimulatory oligonucleotides and to overcome species specificity of the immunostimulatory sequences.

BRIEF SUMMARY OF THE INVENTION

The invention provides methods for modulating the immune response caused by oligonucleotide compounds. The methods according to the invention enable modifying the cytokine profile produced by immunostimulatory oligonucleotides for immunotherapy applications. The present inventors have surprisingly discovered that modification of immunostimulatory dinucleotides allows flexibility in the nature of the immune response produced and that certain modifications overcome the species specificities observed to date of the immunostimulatory sequences. In cetain preferred embodiments, the modified dinucleotide is in the context of an "immunomer", as further described below.

In a first aspect, therefore, the invention provides immunostimulatory oligonucleotides or immunomers comprising at least one immunostimulatory dinucleotide comprising at least one modified purine or pyrimidine.

In one embodiment, the immunomodulatory oligonucleotide or immunomer comprises an immunostimulatory dinucleotide of formula 5'-Pyr-Pur-3', wherein Pyr is a natural or non-natural pyrimidine nucleoside and Pur is a natural or non-natural purine nucleoside. In another preferred embodiment, the immunomodulatory oligonucleotide or immunomer comprises an immunostimulatory dinucleotide of formula 5'-Pur*-Pur-3', wherein Pur* is a non-natural purine nucleoside and Pur is a natural or non-natural purine nucleoside. A particularly preferred synthetic purine is 2-oxo-7-deaza-8-methyl-purine. When this synthetic purine is in the Pur* position of the dinucleotide, species-specificity (sequence dependence) of the immunostimulatory effect is overcome and cytokine profile is improved.

In another embodiment, the immunomodulatory oligonucleotide or immunomer comprises an immunostimulatory dinucleotide selected from the group consisting of CpG, C*pG, CpG*, and C*pG*, wherein the base of C is cytosine, the base of C* is thymine, 5-hydroxycytosine, N4-alkyl-cytosine, 4-thiouracil or other non-natural pyrimidine nucleoside or 2-oxo-7-deaza-8-methyl-purine, wherein when the base is 2-oxo-7-deaza-8-methyl-purine, it is preferably covalently bound to the 1'-position of a pentose via the 1 position of the base; the base of G is guanine, the base of G* is 2-ammno-6-oxo-7-deazapurine, 2-amino-6-thiopurine, 6-oxopurine, or other non-natural purine nucleoside, and p is an internucleoside linkage selected from the group consisting of phosphodiester, phosphorothioate, and phosphorodithioate. In certain preferred embodiments, the immunostimulatory dinucleotide is not CpG.

In yet another embodiment, the immunomodulatory oligonucleotide comprises an immunostimulatory domain of formula (III):

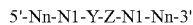 (III)

wherein:

the base of Y is cyto sine, thymine, 5-hydroxycytosine, N4-alkyl-cytosine, 4-thiouracil, or 2-oxo-7-deaza-8-methyl-purine, wherein when the base is 2-oxo-7-deaza-8-methyl-purine, it is preferably covalently bound to the 1'-position of a pentose via the 1 position of the base;

the base of Z is guanine, 2-amino-6-oxo-7-deazapurine, 2-amino-6-thiopurine, or 6-oxopurine.

N1 and Nn independently at each occurrence, is preferably a naturally occurring or a synthetic nucleoside or an immunostimulatory moiety selected from the group consisting of abasic nucleosides, arabinonucleosides, 2'-deoxyuridine, α-deoxyribonucleosides, β-L-deoxyribonucleosides, and nucleosides linked by a phosphodiester or modified internucleoside linkage to the adjacent nucleoside on the 3' side, the modified internucleotide linkage being selected from, without limitation, a linker having a length of from about 2 angstroms to about 200 angstroms, C2-C18 alkyl linker, poly (ethylene glycol) linker, 2-aminobutyl-1,3-propanediol linker, glyceryl linker, 2'-5' internucleoside linkage, and phosphorothioate, phosphorodithioate, or methylphosphonate internucleoside linkage;

provided that at least one N1 or Nn is optionally an immunostimulatory moiety;

wherein n is a number from 0-30;

wherein the 3'end, an internucleotide linkage, or a functionalized nucleobase or sugar may or may not be linked directly or via a non-nucleotidic linker to another oligonucleotide, which may or may not be immunostimulatory. When the immunomodulatory oligonucleotide is linked to another oligonucleotide, it is referred to as an "immunomer".

In a second aspect, the invention provides immunomer conjugates, comprising an immunomer, as described above, and an antigen conjugated to the immunomer at a position other than the accessible 5' end. Similarly, if the oligonucleotide is not linked to another oligonucleotide, but is linked to an antigen at any position other than its accessible 5' end it is referred to as an "immunomodulatory oligonucleotide conjugate."

In a third aspect, the invention provides pharmaceutical formulations comprising an immunostimulatory oligonucleotide, an immunomodulatory oligonucleotide conjugate, an immunomer or an immunomer conjugate according to the invention or combinations of two or more thereof and a physiologically acceptable carrier.

In a fourth aspect, the invention provides methods for generating an immune response in a vertebrate, such methods comprising administering to the vertebrate an immunostimulatory oligonucleotide, an immunomodulatory oligonucleotide conjugate, an immunomer or an immunomer conjugate according to the invention, or combinations of two or more thereof. In some embodiments, the vertebrate is a mammal.

In a fifth aspect, the invention provides methods for therapeutically treating a patient having a disease or disorder, such methods comprising administering to the patient an immunostimulatory oligonucleotide, an immunomodulatory oligonucleotide conjugate, an immunomer or immunomer conjugate according to the invention, or combinations of two or more thereof. In various embodiments, the disease or disorder to be treated is cancer, an autoimmune disorder, airway inflammation, asthma, allergy, or a disease caused by a pathogen.

BRIEF DESCRIPTION OF THE DRAWINGS

FIG. 7A is a graphic representation of the induction of IL-12 by immunomers 1-3 in BALB/c mouse spleen cell cultures. These data suggest that Immunomer 2, which has accessible 5'-ends, is a stronger inducer of IL-12 than monomeric Oligo 1, and that Immunomer 3, which does not have accessible 5'-ends, has equal or weaker ability to produce immune stimulation compared with oligo 1. (e.g., SEQ ID NOS 1, 2, 3)

FIG. 7B is a graphic representation of the induction of IL-6 (top to bottom, respectively) by Immunomers 1-3 in BALB/c mouse spleen cells cultures. These data suggest that Immunomer 2, which has accessible 5'-ends, is a stronger inducer of IL-6 than monomeric Oligo 1, and that Immunomer 3, which does not have accessible 5'-ends, has equal or weaker ability to induce immune stimulation compared with Oligo 1. (SEQ ID NOS 1, 2 and 3)

FIG. 7C is a graphic representation of the induction of IL-10 by Immunomers 1-3 (top to bottom, respectively) in BALB/c mouse spleen cell cultures. (SEQ ID NOS 1, 2 and 3)

FIG. 8A is a graphic representation of the induction of BALB/c mouse spleen cell proliferation in cell cultures by different concentrations of Immunomers 5 and 6, which have inaccessible and accessible 5'-ends, respectively. (SEQ ID NOS 5 and 6)

FIG. 8B is a graphic representation of BALB/c mouse spleen enlargement by Immunomers 4-6, which have an immunogenic chemical modification in the 5'-flanking sequence of the CpG motif. Again, the immunomer, which has accessible 5'-ends (6), has a greater ability to increase spleen enlargement compared with Immunomer 5, which does not have accessible 5'-end and with monomeric Oligo 4. (SEQ ID NOS 4, 5 and 6)

FIG. 9A is a graphic representation of induction of IL-12 by different concentrations of Oligo 4 and Immunomers 7 and 8 in BALB/c mouse spleen cell cultures. (SEQ ID NOS 4, 7 and 8)

FIG. 9B is a graphic representation of induction of IL-6 by different concentrations of Oligo 4 and Immunomers 7 and 8 in BALB/c mouse spleen cell cultures. (SEQ ID NOS 4, 7 and 8)

FIG. 9C is a graphic representation of induction of IL-10 by different concentrations of Oligo 4 and Immunomers 7 and 8 in BALB/c mouse spleen cell cultures. (SEQ ID NOS 4, 7 and 8)

FIG. 10A is a graphic representation of the induction of cell proliferation by Immunomers 14, 15, and 16 in BALB/c mouse spleen cell cultures. (SEQ ID NOS 14, 15 and 16)

FIG. 10B is a graphic representation of the induction of cell proliferation by IL-12 by different concentrations of Immunomers 14 and 16 in BALB/c mouse spleen cell cultures. (SEQ ID NOS 14, 15 and 16)

FIG. 10C is a graphic representation of the induction of cell proliferation by IL-6 by different concentrations of Immunomers 14 and 16 in BALB/c mouse spleen cell cultures. (SEQ ID NOS 14, 15 and 16)

FIG. 11A is a graphic representation of the induction of cell proliferation by Oligo 4 and 17 and Immunomers 19 and 20 in BALB/c mouse spleen cell cultures. (SEQ ID NOS 4, 17, 19 and 20)

FIG. 11B is a graphic representation of the induction of IL-12 production by different concentrations of Oligo 4 and 17 and Immunomers 19 and 20 in BALB/c mouse spleen cell cultures. (SEQ ID NOS 4, 17, 19 and 20)

FIG. 11C is a graphic representation of the induction of IL-6 production by different concentrations of Oligo 4 and 17 and Immunomers 19 and 20 in BALB/c mouse spleen cell cultures. (SEQ ID NOS 4, 17, 19 and 20)

DETAILED DESCRIPTION OF THE PREFERRED EMBODIMENTS

The invention relates to the therapeutic use of oligonucleotides as immunostimulatory agents for immunotherapy applications. The issued patents, patent applications, and references that are cited herein are hereby incorporated by reference to the same extent as if each was specifically and individually indicated to be incorporated by reference. In the event of inconsistencies between any teaching of any reference cited herein and the present specification, the latter shall prevail for purposes of the invention.

The invention provides methods for enhancing the immune response caused by immunostimulatory compounds used for immunotherapy applications such as, but not limited to, treatment of cancer, autoimmune disorders, asthma, respiratory allergies, food allergies, and bacteria, parasitic, and viral infections in adult and pediatric human and veterinary applications. Thus, the invention further provides compounds having optimal levels of immunostimulatory effect for immunotherapy and methods for making and using such compounds. In addition, compounds of the invention are useful as adjuvants in combination with DNA vaccines, antibodies, and allergens; and in combination with chemotherapeutic agents and/or antisense oligonucleotides.

The present inventors have surprisingly discovered that modification of an immunomodulatory oligonucleotide to optimally present its 5' ends dramatically affects its immunostimulatory capabilities. In addition, the present inventors have discovered that the cytokine profile and species specificity of an immune response can be modulated by using novel purine or pyrimidine structures as part of an immunomodulatory oligonucleotide or an immunomer.

In a first aspect, the invention provides immunostimulatory oligonucleotides or "immunomers", the latter comprising at least two oligonucleotides linked at their 3' ends, or an internucleoside linkage or a functionalized nucleobase or sugar to a non-nucleotidic linker, at least one of the oligonucleotides being an immunomodulatory oligonucleotide and having an accessible 5' end. As used herein, the term "accessible 5' end" means that the 5' end of the oligonucleotide is sufficiently available such that the factors that recognize and bind to immunomers and stimulate the immune system have access to it. In oligonucleotides having an accessible 5' end, the 5' OH position of the terminal sugar is not covalently linked to more than two nucleoside residues or any other moiety that interferes with interaction with the 5' end. Optionally, the 5' OH can be linked to a phosphate, phosphorothioate, or phosphorodithioate moiety, an aromatic or aliphatic linker, cholesterol, or another entity which does not interfere with accessibility. The immunostimulatory oligonucleotides or immunomers according to the invention preferably further comprise an immunostimulatory dinucleotide comprising a novel purine or pyrimidine.

Figure 14:
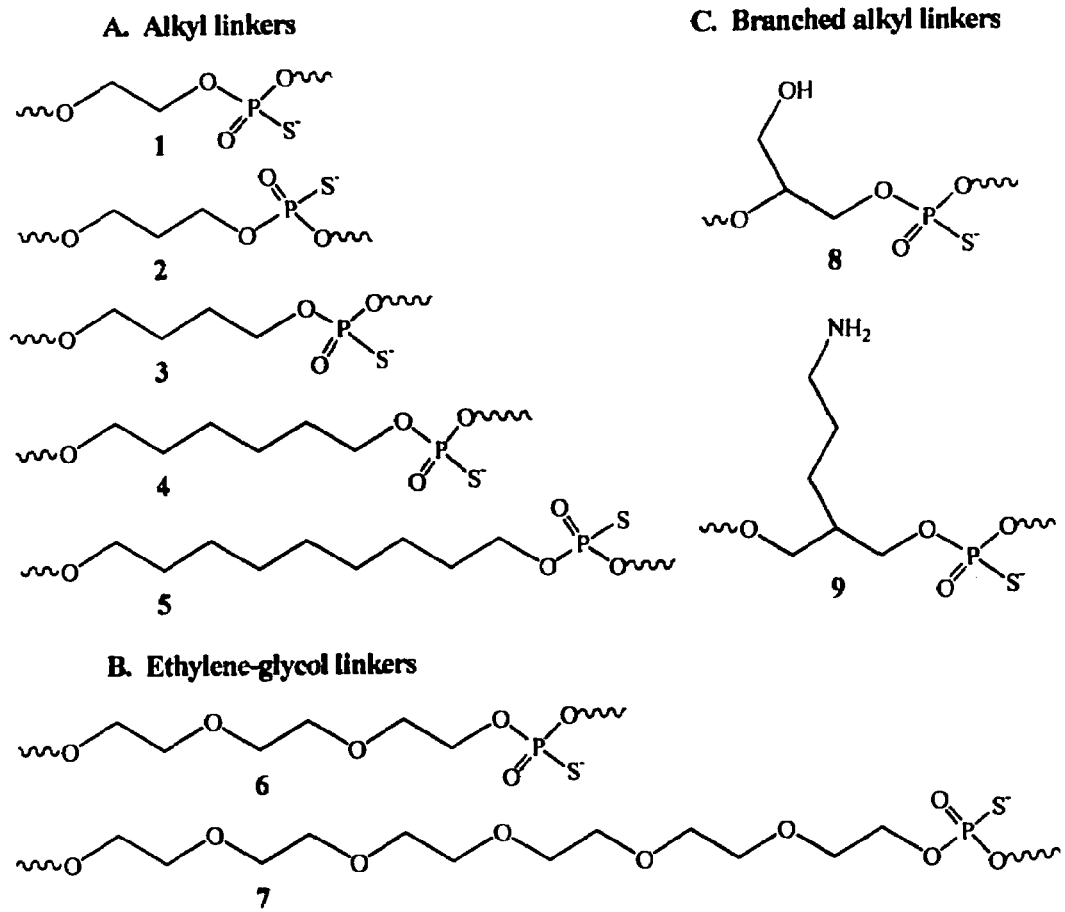
FIG. 14 shows the chemical substitutions used in Example 13.

In some embodiments, immunostimulatory oligonucleotides according to the invention may have oligonucleotide sequences connected 5' to 3' by linkers, such as those shown in FIG. 14.

In some embodiments, the immunomer comprises two or more immunostimulatory oligonucleotides, (in the context of the immunomer) which may be the same or different. Preferably, each such immunomodulatory oligonucleotide has at least one accessible 5' end.

In certain embodiments, in addition to the immunostimulatory oligonucleotide(s), the immunomer also comprises at least one oligonucleotide that is complementary to a gene or its RNA product. As used herein, the term "complementary to" means that the oligonucleotide hybridizes under physiological conditions to a region of the gene. In some embodiments, the oligonucleotide downregulates expression of a gene. Such downregulatory oligonucleotides preferably are selected from the group consisting of antisense oligonucleotides, ribozyme oligonucleotides, small inhibitory RNAs and decoy oligonucleotides. As used herein, the term "downregulate a gene" means to inhibit the transcription of a gene or translation of a gene product. Thus, the immunomers according to these embodiments of the invention can be used to target one or more specific disease targets, while also stimulating the immune system.

In certain embodiments, the immunomer includes a ribozyme or a decoy oligonucleotide. As used herein, the term "ribozyme" refers to an oligonucleotide that possesses catalytic activity. Preferably, the ribozyme binds to a specific nucleic acid target and cleaves the target. As used herein, the term "decoy oligonucleotide" refers to an oligonucleotide that binds to a transcription factor in a sequence-specific manner and arrests transcription activity. Preferably, the ribozyme or decoy oligonucleotide exhibits secondary structure, including, without limitation, stem-loop or hairpin structures. In certain embodiments, at least one oligonucleotide comprises poly(I)-poly(C). In certain embodiments, at least one set of Nn includes a string of 3 to 10 dGs and/or Gs or 2'-substituted ribo or arabino Gs.

For purposes of the invention, the term "oligonucleotide" refers to a polynucleoside formed from a plurality of linked nucleoside units. Such oligonucleotides can be obtained from existing nucleic acid sources, including genomic or cDNA, but are preferably produced by synthetic methods. In preferred embodiments each nucleoside unit includes a heterocyclic base and a pentofuranosyl, trehalose, arabinose, 2'-deoxy-2'-substituted arabinose, 2'-O-substituted arabinose or hexose sugar group. The nucleoside residues can be coupled to each other by any of the numerous known internucleoside linkages. Such internucleoside linkages include, without limitation, phosphodiester, phosphorothioate, phosphorodithioate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone internucleoside linkages. The term "oligonucleotide" also encompasses polynucleosides having one or more stereospecific internucleoside linkage (e.g., (Rp)- or (Sp)-phosphorothioate, alkylphosphonate, or phosphotriester linkages). As used herein, the terms "oligonucleotide" and "dinucleotide" are expressly intended to include polynucleosides and dinucleosides having any such internucleoside linkage, whether or not the linkage comprises a phosphate group. In certain preferred embodiments, these internucleoside linkages may be phosphodiester, phosphorothioate, or phosphorodithioate linkages, or combinations thereof.

In some embodiments, the oligonucleotides each have from about 3 to about 35 nucleoside residues, preferably from about 4 to about 30 nucleoside residues, more preferably from about 4 to about 20 nucleoside residues. In some embodiments, the immunomers comprise oligonucleotides have from about 5 to about 18, or from about 5 to about 14, nucleoside residues. As used herein, the term "about" implies that the exact number is not critical. Thus, the number of nucleoside residues in the oligonucleotides is not critical, and oligonucleotides having one or two fewer nucleoside residues, or from one to several additional nucleoside residues are contemplated as equivalents of each of the embodiments described above. In some embodiments, one or more of the oligonucleotides have 11 nucleotides. In the context of immunostimulatory oligonucleotides, preferred embodiments have from about 13 to about 35 nucleotides, more preferably from about 13 to about 26 nucleotides.

The term "oligonucleotide" also encompasses polynucleosides having additional substituents including, without limitation, protein groups, lipophilic groups, intercalating agents, diamines, folic acid, cholesterol and adamantane. The term "oligonucleotide" also encompasses any other nucleobase containing polymer, including, without limitation, peptide nucleic acids (PNA), peptide nucleic acids with phosphate groups (PHONA), locked nucleic acids (LNA), morpholino-backbone oligonucleotides, and oligonucleotides having backbone sections with alkyl linkers or amino linkers.

The oligonucleotides of the invention can include naturally occurring nucleosides, modified nucleosides, or mixtures thereof. As used herein, the term "modified nucleoside" is a nucleoside that includes a modified heterocyclic base, a modified sugar moiety, or a combination thereof. In some embodiments, the modified nucleoside is a non-natural pyrimidine or purine nucleoside, as herein described. In some embodiments, the modified nucleoside is a 2'-substituted ribonucleoside an arabinonucleoside or a 2'-deoxy-2'-substituted-arabinoside.

For purposes of the invention, the term "2'-substituted ribonucleoside" or "2'-substituted arabinoside" includes ribonucleosides or arabinonucleoside in which the hydroxyl group at the 2' position of the pentose moiety is substituted to produce a 2'-substituted or 2'-O-substituted ribonucleoside. Preferably, such substitution is with a lower alkyl group containing 1-6 saturated or unsaturated carbon atoms, or with an aryl group having 6-10 carbon atoms, wherein such alkyl, or aryl group may be unsubstituted or may be substituted, e.g., with halo, hydroxy, trifluoromethyl, cyano, nitro, acyl, acyloxy, alkoxy, carboxyl, carboalkoxy, or amino groups. Examples of 2'-O-substituted ribonucleosides or 2'-O-substituted-arabinosides include, without limitation 2'-O-methylribonucleosides or 2'-O-methylarabinosides and 2'-O-methoxyethylribonucleosides or 2'-O-methoxyethylarabinosides.

The term "2'-substituted ribonucleoside" or "2'-substituted arabinoside" also includes ribonucleosides or arabinonucleosides in which the 2'-hydroxyl group is replaced with a lower alkyl group containing 1-6 saturated or unsaturated carbon atoms, or with an amino or halo group. Examples of such 2'-substituted ribonucleosides or 2'-substituted arabinosides include, without limitation, 2'-amino, 2'-fluoro, 2'-allyl, and 2'-propargyl ribonucleosides or arabinosides.

The term "oligonucleotide" includes hybrid and chimeric oligonucleotides. A "chimeric oligonucleotide" is an oligonucleotide having more than one type of internucleoside linkage. One preferred example of such a chimeric oligonucleotide is a chimeric oligonucleotide comprising a phosphorothioate, phosphodiester or phosphorodithioate region and non-ionic linkages such as alkylphosphonate or alkylphosphonothioate linkages (see e.g., Pederson et al. U.S. Pat. Nos. 5,635,377 and 5,366,878).

A "hybrid oligonucleotide" is an oligonucleotide having more than one type of nucleoside. One preferred example of such a hybrid oligonucleotide comprises a ribonucleotide or 2'-substituted ribonucleotide region, and a deoxyribonucleotide region (see, e.g., Metelev and Agrawal, U.S. Pat. Nos. 5,652,355, 6,346,614 and 6,143,881).

For purposes of the invention, the term "immunostimulatory oligonucleotide" refers to an oligonucleotide as described above that induces an immune response when administered to a vertebrate, such as a fish, fowl, or mammal. As used herein, the term "mammal" includes, without limitation rats, mice, cats, dogs, horses, cattle, cows, pigs, rabbits, non-human primates, and humans. Useful immunostimulatory oligonucleotides can be found described in Agrawal et al., WO 98/49288, published Nov. 5, 1998; WO 01/12804, published Feb. 22, 2001; WO 01/55370, published Aug. 2, 2001; PCT/US01/13682, filed Apr. 30, 2001; and PCT/US01/30137, filed Sep. 26, 2001. Preferably, the immunomodulatory oligonucleotide comprises at least one phosphodiester, phosphorothioate, or phosphorodithioate internucleoside linkage.

In some embodiments, the immunomodulatory oligonucleotide comprises an immunostimulatory dinucleotide of formula 5'-Pyr-Pur-3', wherein Pyr is a natural or synthetic pyrimidine nucleoside and Pur is a natural or synthetic purine nucleoside. In some preferred embodiments, the immunomodulatory oligonucleotide comprises an immunostimulatory dinucleotide of formula 5'-Pur*-Pur-3', wherein Pur* is a synthetic purine nucleoside and Pur is a natural or synthetic purine nucleoside. In various places the dinucleotide is expressed as RpG, C*pG or YZ, in which case respectively, R, C*, or Y represents a synthetic purine. A particularly preferred synthetic purine is 2-oxo-7-deaza-8-methyl-purine. When this synthetic purine is in the Pur* position of the dinucleotide, species-specificity (sequence dependence) of the immunostimulatory effect is overcome and cytokine profile is improved. As used herein, the term "pyrimidine nucleoside" refers to a nucleoside wherein the base component of the nucleoside is a monocyclic nucleobase. Similarly, the term "purine nucleoside" refers to a nucleoside wherein the base component of the nucleoside is a bicyclic nucleobase. For purposes of the invention, a "synthetic" pyrimidine or purine nucleoside includes a non-naturally occurring pyrimidine or purine base, a non-naturally occurring sugar moiety, or a combination thereof.

Preferred pyrimidine nucleosides according to the invention have the structure (I):

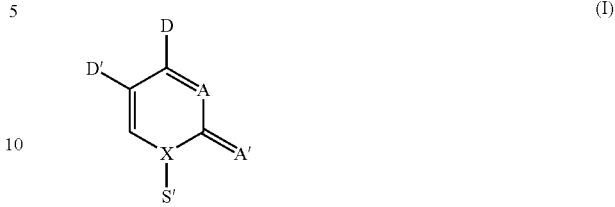

wherein:

D is a hydrogen bond donor;

D' is selected from the group consisting of hydrogen, hydrogen bond donor, hydrogen bond acceptor, hydrophilic group, hydrophobic group, electron withdrawing group and electron donating group;

A is a hydrogen bond acceptor or a hydrophilic group;

A' is selected from the group consisting of hydrogen bond acceptor, hydrophilic group, hydrophobic group, electron withdrawing group and electron donating group;

X is carbon or nitrogen; and

S' is a pentose or hexose sugar ring, or a non-naturally occurring sugar.

Preferably, the sugar ring is derivatized with a phosphate moiety, modified phosphate moiety, or other linker moiety suitable for linking the pyrimidine nucleoside to another nucleoside or nucleoside analog.

Preferred hydrogen bond donors include, without limitation, —NH—, —NH$_2$, —SH and —OH. Preferred hydrogen bond acceptors include, without limitation, C=O, C=S, and the ring nitrogen atoms of an aromatic heterocycle, e.g., N3 of cytosine.

In some embodiments, the base moiety in (I) is a non-naturally occurring pyrimidine base. Examples of preferred non-naturally occurring pyrimidine bases include, without limitation, 5-hydroxycytosine, 5-hydroxymethylcytosine, N4-alkylcytosine, preferably N4-ethylcytosine, and 4-thiouracil. However, in some embodiments 5-bromocytosine is specifically excluded.

In some embodiments, the sugar moiety S' in (I) is a non-naturally occurring sugar moiety. For purposes of the present invention, a "naturally occurring sugar moiety" is a sugar moiety that occurs naturally as part of nucleic acid, e.g., ribose and 2'-deoxyribose, and a "non-naturally occurring sugar moiety" is any sugar that does not occur naturally as part of a nucleic acid, but which can be used in the backbone for an oligonucleotide, e.g, hexose. Arabinose and arabinose derivatives are examples of preferred sugar moieties.

Preferred purine nucleoside analogs according to the invention have the structure (II):

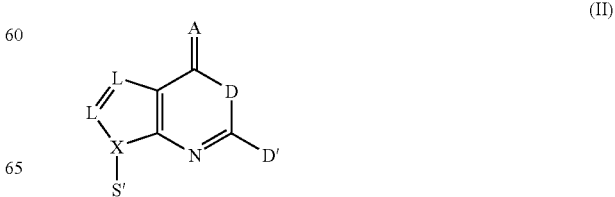

wherein:
D is a hydrogen bond donor;
D' is selected from the group consisting of hydrogen, hydrogen bond donor, and hydrophilic group;
A is a hydrogen bond acceptor or a hydrophilic group;
X is carbon or nitrogen;
each L is independently an atom selected from the group consisting of C, O, N and S; and
S' is a pentose or hexose sugar ring, or a non-naturally occurring sugar.

Preferably, the sugar ring is derivatized with a phosphate moiety, modified phosphate moiety, or other linker moiety suitable for linking the pyrimidine nucleoside to another nucleoside or nucleoside analog.

Preferred hydrogen bond donors include, without limitation, —NH—, —NH$_2$, —SH and —OH. Preferred hydrogen bond acceptors include, without limitation, C═O, C═S, —NO$_2$ and the ring nitrogen atoms of an aromatic heterocycle, e.g., N1 of guanine.

In some embodiments, the base moiety in (II) is a non-naturally occurring purine base. Examples of preferred non-naturally occurring purine bases include, without limitation, 2-amino-6-thiopurine and 2-amino-6-oxo-7-deazapurine. In some embodiments, the sugar moiety S' in (II) is a naturally occurring sugar moiety, as described above for structure (I).

In preferred embodiments, the immunostimulatory dinucleotide is selected from the group consisting of CpG, C*pG, CpG*, and C*pG*, wherein the base of C is cytosine, the base of C* is 2'-thymine, 5-hydroxycytosine, N4-alkyl-cytosine, 4-thiouracil or other non-natural pyrimidine, or 2-oxo-7-deaza-8-methylpurine, wherein when the base is 2-oxo-7-deaza-8-methyl-purine, it is preferably covalently bound to the 1'-position of a pentose via the 1 position of the base; the base of G is guanosine, the base of G* is 2-amino-6-oxo-7-deazapurine, 2-oxo-7-deaza-8-methylpurine, 6-thioguanine, 6-oxopurine, or other non-natural purine nucleoside, and p is an internucleoside linkage selected from the group consisting of phosphodiester, phosphorothioate, and phosphorodithioate. In certain preferred embodiments, the immunostimulatory dinucleotide is not CpG.

The immunostimulatory oligonucleotides may include immunostimulatory moieties on one or both sides of the immunostimulatory dinucleotide. Thus, in some embodiments, the immunomodulatory oligonucleotide comprises an immunostimulatory domain of structure (III):

5'-Nn-N1-Y-Z-N1-Nn-3'  (III)

wherein:
the base of Y is cytosine, thymine, 5-hydroxycytosine, N4-alkyl-cytosine, 4-thiouracil or other non-natural pyrimidine nucleoside, or 2-oxo-7-deaza-8 methyl purine, wherein when the base is 2-oxo-7-deaza-8-methyl-purine, it is preferably covalently bound to the 1'-position of a pentose via the 1 position of the base;
the base of Z is guanine, 2-amino-6-oxo-7-deazapurine, 2-oxo-7deaza-8-methylpurine, 2-amino-6-thio-purine, 6-oxopurine or other non-natural purine nucleoside;
N1 and Nn, independent at each occurrence, is preferably a naturally occurring or a synthetic nucleoside or an immunostimulatory moiety selected from the group consisting of abasic nucleosides, arabinonucleosides, 2'-deoxyuridine, α-deoxyribonucleosides, β-L-deoxyribonucleosides, and nucleosides linked by a phosphodiester or modified internucleoside linkage to the adjacent nucleoside on the 3' side, the modified internucleotide linkage being selected from, without limitation, a linker having a length of from about 2 angstroms to about 200 angstroms, C2-C18 alkyl linker, poly(ethylene glycol) linker, 2-aminobutyl-1,3-propanediol linker, glyceryl linker, 2'-5' internucleoside linkage, and phosphorothioate, phosphorodithioate, or methylphosphonate internucleoside linkage;
provided that at least one N1 or Nn is optionally an immunostimulatory moiety;
wherein n is a number from 0 to 30; and
wherein the 3'end, an internucleoside linker, or a derivatized nucleobase or sugar is linked directly or via a non-nucleotidic linker to another oligonucleotide, which may or may not be immunostimulatory.

In some preferred embodiments, YZ is arabinocytidine or 2'-deoxy-2'-substituted arabinocytidine and arabinoguanosine or 2'deoxy-2'-substituted arabinoguanosine. Preferred immunostimulatory moieties include natural phosphodiester backbones and modifications in the phosphate backbones, including, without limitation, methylphosphonates, methylphosphonothioates, phosphotriesters, phosphothiotriesters, phosphorothioates, phosphorodithioates, triester prodrugs, sulfones, sulfonamides, sulfamates, formacetal, N-methylhydroxylamine, carbonate, carbamate, morpholino, boranophosphonate, phosphoramidates, especially primary amino-phosphoramidates, N3 phosphoramidates and N5 phosphoramidates, and stereospecific linkages (e.g., (Rp)- or (Sp)-phosphorothioate, alkylphosphonate, or phosphotriester linkages).

Preferred immunostimulatory moieties according to the invention further include nucleosides having sugar modifications, including, without limitation, 2'-substituted pentose sugars including, without limitation, 2'-O-methylribose, 2'-O-methoxyethylribose, 2'-O-propargylribose, and 2'-deoxy-2'-fluororibose; 3'-substituted pentose sugars, including, without limitation, 3'-O-methylribose; 1',2'-dideoxyribose; arabinose; substituted arabinose sugars, including, without limitation, 1'-methylarabinose, 3'-hydroxymethylarabinose, 4'-hydroxymethylarabinose, 3'-hydroxyarabinose and 2'-substituted arabinose sugars; hexose sugars, including, without limitation, 1,5-anhydrohexitol; and alpha-anomers. In embodiments in which the modified sugar is a 3'-deoxyribonucleoside or a 3'-O-substituted ribonucleoside, the immunostimulatory moiety is attached to the adjacent nucleoside by way of a 2'-5' internucleoside linkage.

Preferred immunostimulatory moieties according to the invention further include oligonucleotides having other carbohydrate backbone modifications and replacements, including peptide nucleic acids (PNA), peptide nucleic acids with phosphate groups (PHONA), locked nucleic acids (LNA), morpholino backbone oligonucleotides, and oligonucleotides having backbone linker sections having a length of from about 2 angstroms to about 200 angstroms, including without limitation, alkyl linkers or amino linkers. The alkyl linker may be branched or unbranched, substituted or unsubstituted, and chirally pure or a racemic mixture. Most preferably, such alkyl linkers have from about 2 to about 18 carbon atoms. In some preferred embodiments such alkyl linkers have from about 3 to about 9 carbon atoms. Some alkyl linkers include one or more functional groups selected from the group consisting of hydroxy, amino, thiol, thioether, ether, amide, thioamide, ester, urea, and thioether. Some such functionalized alkyl linkers are poly(ethylene glycol) linkers of formula —O—(CH$_2$—CH$_2$—O—)$_n$ (n=1-9). Some other functionalized alkyl linkers are peptides or amino acids.

Preferred immunostimulatory moieties according to the invention further include DNA isoforms, including, without limitation, β-L-deoxyribonucleosides and α-deoxyribonucleosides. Preferred immunostimulatory moieties according to the invention incorporate 3' modifications, and further include nucleosides having unnatural internucleoside linkage positions, including, without limitation, 2'-5', 2'-2', 3'-3' and 5'-5' linkages.

Preferred immunostimulatory moieties according to the invention further include nucleosides having modified heterocyclic bases, including, without limitation, 5-hydroxycytosine, 5-hydroxymethylcytosine, N4-alkylcytosine, preferably N4-ethylcytosine, 4-thiouracil, 6-thioguanine, 7-deazaguanine, inosine, nitropyrrole, C5-propynylpyrimidine, and diaminopurines, including, without limitation, 2,6-diaminopurine.

By way of specific illustration and not by way of limitation, for example, in the immunostimulatory domain of structure (III), a methylphosphonate internucleoside linkage at position N1 or Nn is an immunostimulatory moiety, a linker having a length of from about 2 angstroms to about 200 angstroms, C2-C18 alkyl linker at position X1 is an immunostimulatory moiety, and a β-L-deoxyribonucleoside at position X1 is an immunostimulatory moiety. See Table 1 below for representative positions and structures of immunostimulatory moieties. It is to be understood that reference to a linker as the immunostimulatory moiety at a specified position means that the nucleoside residue at that position is substituted at its 3'-hydroxyl with the indicated linker, thereby creating a modified internucleoside linkage between that nucleoside residue and the adjacent nucleoside on the 3' side. Similarly, reference to a modified internucleoside linkage as the immunostimulatory moiety at a specified position means that the nucleoside residue at that position is linked to the adjacent nucleoside on the 3' side by way of the recited linkage.

TABLE 1

| Position | TYPICAL IMMUNOSTIMULATORY MOIETIES |
|---|---|
| N1 | Naturally-occurring nucleosides, abasic nucleoside, arabinonucleoside, 2'-deoxyuridine, β-L-deoxyribonucleoside C2-C18 alkyl linker, poly(ethylene glycol) linkage, 2-aminobutyl-1,3-propanediol linker (amino linker), 2'-5' internucleoside linkage, methylphosphonate internucleoside linkage |
| Nn | Naturally-occurring nucleosides, abasic nucleoside, arabinonucleosides, 2'-deoxyuridine, 2'-O-substituted ribonucleoside, 2'-5'internucleoside linkage, methylphosphonate internucleoside linkage, provided that N1 and N2 cannot both be abasic linkages |

Table 2 shows representative positions and structures of immunostimulatory moieties within an immunomodulatory oligonucleotide having an upstream potentiation domain. As used herein, the term "Spacer 9" refers to a poly(ethylene glycol) linker of formula —O—(CH$_2$CH$_2$—O)$_n$—, wherein n is 3. The term "Spacer 18" refers to a poly(ethylene glycol) linker of formula —O—(CH$_2$CH$_2$—O)$_n$—, wherein n is 6. As used herein, the term "C2-C18 alkyl linker refers to a linker of formula —O—(CH$_2$)$_q$—O—, where q is an integer from 2 to 18. Accordingly, the terms "C3-linker" and "C3-alkyl linker" refer to a linker of formula —O—(CH$_2$)$_3$—O—. For each of Spacer 9, Spacer 18, and C2-C18 alkyl linker, the linker is connected to the adjacent nucleosides by way of phosphodiester, phosphorothioate, or phosphorodithioate linkages.

TABLE 2

| Position | TYPICAL IMMUNOSTIMULATORY MOIETY |
|---|---|
| 5' N2 | Naturally-occurring nucleosides, 2-aminobutyl-1,3-propanediol linker |
| 5' N1 | Naturally-occurring nucleosides, β-L-deoxyribonucleoside, C2-C18 alkyl linker, poly(ethylene glycol), abasic linker, 2-aminobutyl-1,3-propanediol linker |
| 3' N1 | Naturally-occurring nucleosides, 1',2'-dideoxyribose, 2'-O-methyl-ribonucleoside, C2-C18 alkyl linker, Spacer 9, Spacer 18 |
| 3' N2 | Naturally-occurring nucleosides, 1',2'-dideoxyribose, 3'-deoxyribonucleoside, β-L-deoxyribonucleoside, 2'-O-propargyl-ribonucleoside, C2-C18 alkyl linker, Spacer 9, Spacer 18, methylphosphonate internucleoside linkage |
| 3' N3 | Naturally-occurring nucleosides, 1',2'-dideoxyribose, C2-C18 alkyl linker, Spacer 9, Spacer 18, methylphosphonate internucleoside linkage, 2'-5' internucleoside linkage, d(G)n, polyI-polyC |
| 3' N2 + 3' N3 | 1',2'-dideoxyribose, β-L-deoxyribonucleoside, C2-C18 alkyl linker, d(G)n, polyI-polyC |
| 3' N3 + 3' N4 | 2'-O-methoxyethyl-ribonucleoside, methylphosphonate internucleoside linkage, d(G)n, polyI-polyC |
| 3' N5 + 3' N6 | 1',2'-dideoxyribose, C2-C18 alkyl linker, d(G)n, polyI-polyC |
| 5' N1 + 3' N3 | 1',2'-dideoxyribose, d(G)n, polyI-polyC |

Table 3 shows representative positions and structures of immunostimulatory moieties within an immunomodulatory oligonucleotide having a downstream potentiation domain.

TABLE 3

| Position | TYPICAL IMMUNOSTIMULATORY MOIETY |
|---|---|
| 5' N2 | methylphosphonate internucleoside linkage |
| 5' N1 | methylphosphonate internucleoside linkage |
| 3' N1 | 1',2'-dideoxyribose, methylphosphonate internucleoside linkage, 2'-O-methyl |
| 3' N2 | 1',2'-dideoxyribose, β-L-deoxyribonucleoside, C2-C18 alkyl linker, Spacer 9, Spacer 18, 2-aminobutyl-1,3-propanediol linker, methylphosphonate internucleoside linkage, 2'-O-methyl |
| 3' N3 | 3'-deoxyribonucleoside, 3'-O-substituted ribonucleoside, 2'-O-propargyl-ribonucleoside |
| 3' N2 + 3' N3 | 1',2'-dideoxyribose, β-L-deoxyribonucleoside |

The immunomers according to the invention comprise at least two oligonucleotides linked at their 3' ends or internucleoside linkage or a functionalized nucleobase or sugar via a non-nucleotidic linker. For purposes of the invention, a "non-nucleotidic linker" is any moiety that can be linked to the oligonucleotides by way of covalent or non-covalent linkages. Preferably such linker is from about 2 angstroms to about 200 angstroms in length. Several examples of preferred linkers are set forth below. Non-covalent linkages include, but are not limited to, electrostatic interaction, hydrophobic interactions, π-stacking interactions, and hydrogen bonding. The term "non-nucleotidic linker" is not meant to refer to an internucleoside linkage, as described above, e.g., a phosphodiester, phosphorothioate, or phosphorodithioate functional group, that directly connects the 3'-hydroxyl groups of two nucleosides. For purposes of this invention, such a direct 3'-3' linkage (no linker involved) is considered to be a "nucleotidic linkage."

In some embodiments, the non-nucleotidic linker is a metal, including, without limitation, gold particles. In some other embodiments, the non-nucleotidic linker is a soluble or insoluble biodegradable polymer bead.

Figure 13:
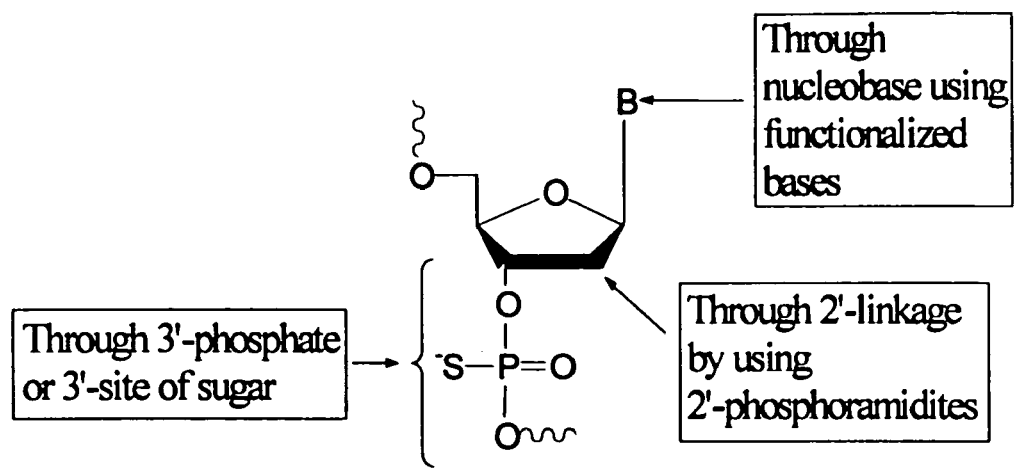
FIG. 13 is a schematic representation of the 3'-terminal nucleoside of an oligonucleotide, showing that a non-nucleotidic linkage can be attached to the nucleoside at the nucleobase, at the 3' position, or at the 2' position.

In yet other embodiments, the non-nucleotidic linker is an organic moiety having functional groups that permit attachment to the oligonucleotide. Such attachment preferably is by any stable covalent linkage. As a non-limiting example, the linker may be attached to any suitable position on the nucleoside, as illustrated in FIG. 13. In some preferred embodiments, the linker is attached to the 3'-hydroxyl. In such embodiments, the linker preferably comprises a hydroxyl functional group, which preferably is attached to the 3'-hydroxyl by means of a phosphodiester, phosphorothioate, phosphorodithioate or non-phosphate-based linkages.

In some embodiments, the non-nucleotidic linker is a biomolecule, including, without limitation, polypeptides, antibodies, lipids, antigens, allergens, and oligosaccharides. In some other embodiments, the non-nucleotidic linker is a small molecule. For purposes of the invention, a small molecule is an organic moiety having a molecular weight of less than 1,000 Da. In some embodiments, the small molecule has a molecular weight of less than 750 Da.

In some embodiments, the small molecule is an aliphatic or aromatic hydrocarbon, either of which optionally can include, either in the linear chain connecting the oligonucleotides or appended to it, one or more functional groups selected from the group consisting of hydroxy, amino, thiol, thioether, ether, amide, thioamide, ester, urea, and thiourea. The small molecule can be cyclic or acyclic. Examples of small molecule linkers include, but are not limited to, amino acids, carbohydrates, cyclodextrins, adamantane, cholesterol, haptens and antibiotics. However, for purposes of describing the non-nucleotidic linker, the term "small molecule" is not intended to include a nucleoside.

In some embodiments, the small molecule linker is glycerol or a glycerol homolog of the formula HO—$(CH_2)_o$—CH(OH)—$(CH_2)_p$—OH, wherein o and p independently are integers from 1 to about 6, from 1 to about 4, or from 1 to about 3. In some other embodiments, the small molecule linker is a derivative of 1,3-diamino-2-hydroxypropane. Some such derivatives have the formula HO—$(CH_2)_m$—C(O)NH—$CH_2$—CH(OH)—$CH_2$—NHC(O)—$(CH_2)_m$—OH, wherein m is an integer from 0 to about 10, from 0 to about 6, from 2 to about 6, or from 2 to about 4.

Figure 1:
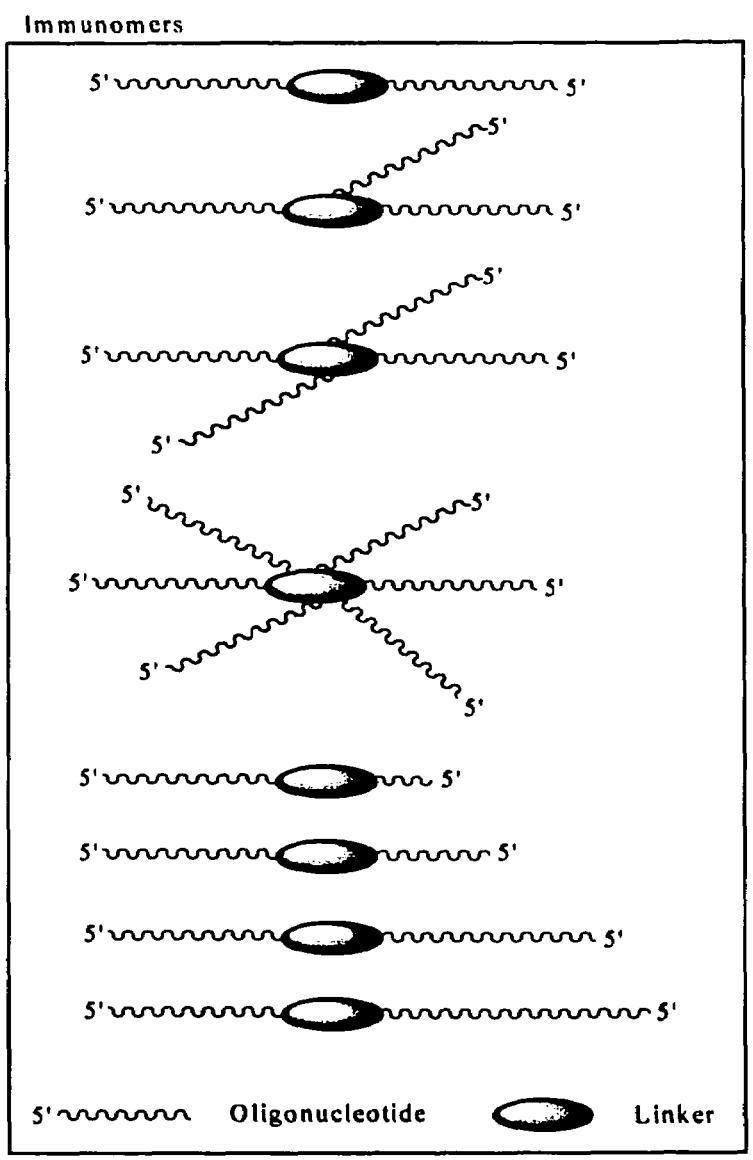
FIG. 1 is a schematic representation of representative immunomers of the invention.
Figure 2:
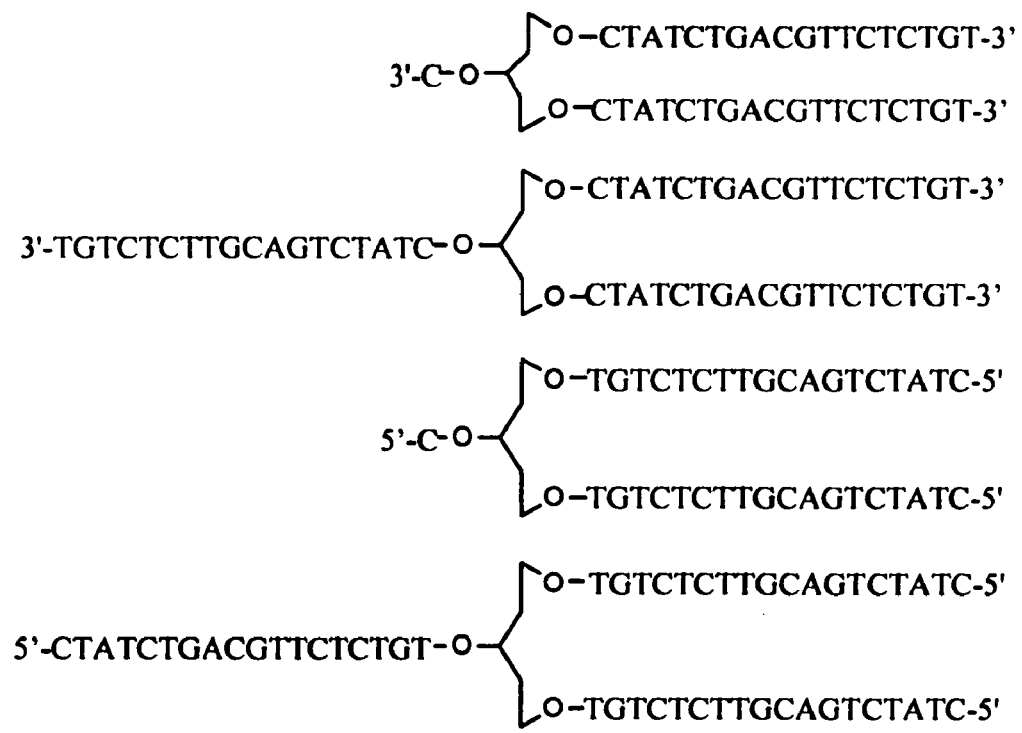
FIG. 2 depicts several representative immunomers of the invention (e.g., SEQ ID NO: 8).
Figure 3:
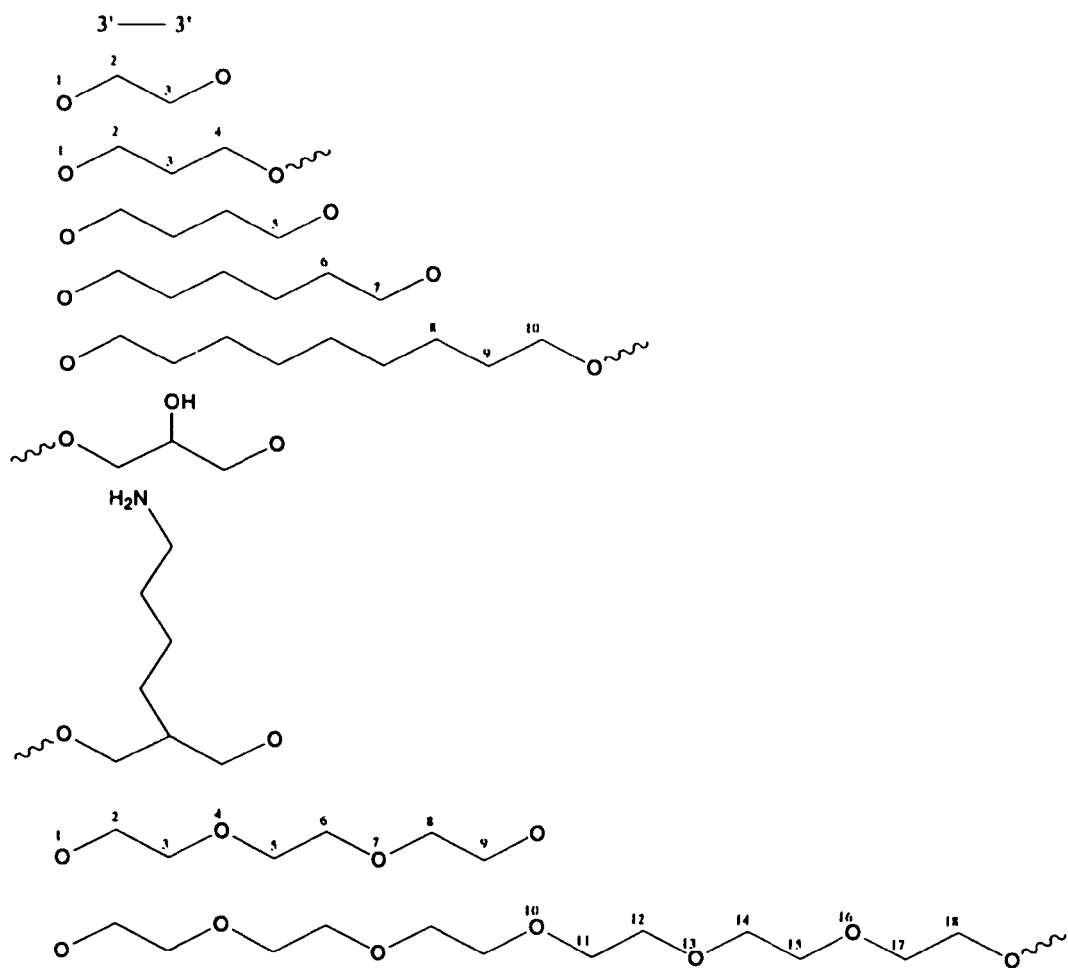
FIG. 3 depicts a group of representative small molecule linkers suitable for linear synthesis of immunomers of the invention.

Some non-nucleotidic linkers according to the invention permit attachment of more than two oligonucleotides, as schematically depicted in FIG. 1. For example, the small molecule linker glycerol has three hydroxyl groups to which oligonucleotides may be covalently attached. Some immunomers according to the invention, therefore, comprise more than two oligonucleotides linked at their 3' ends to a non-nucleotidic linker. Some such immunomers comprise at least two immunostimulatory oligonucleotides, each having an accessible 5' end.

Figure 5:
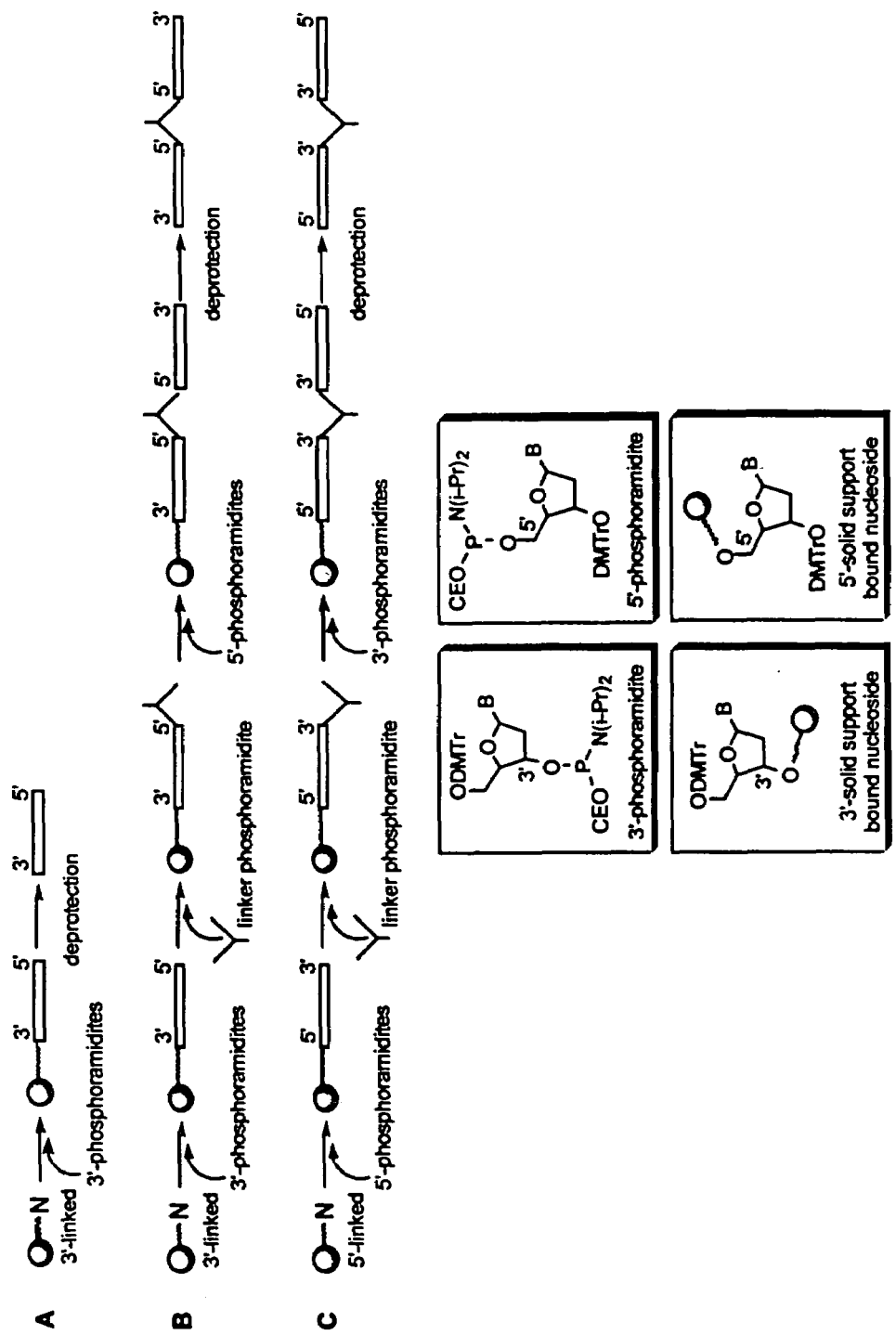
FIG. 5 is a synthetic scheme for the linear synthesis of immunomers of the invention. DMTr=4,4'-dimethoxytrityl; CE=cyanoethyl.
Figure 6:
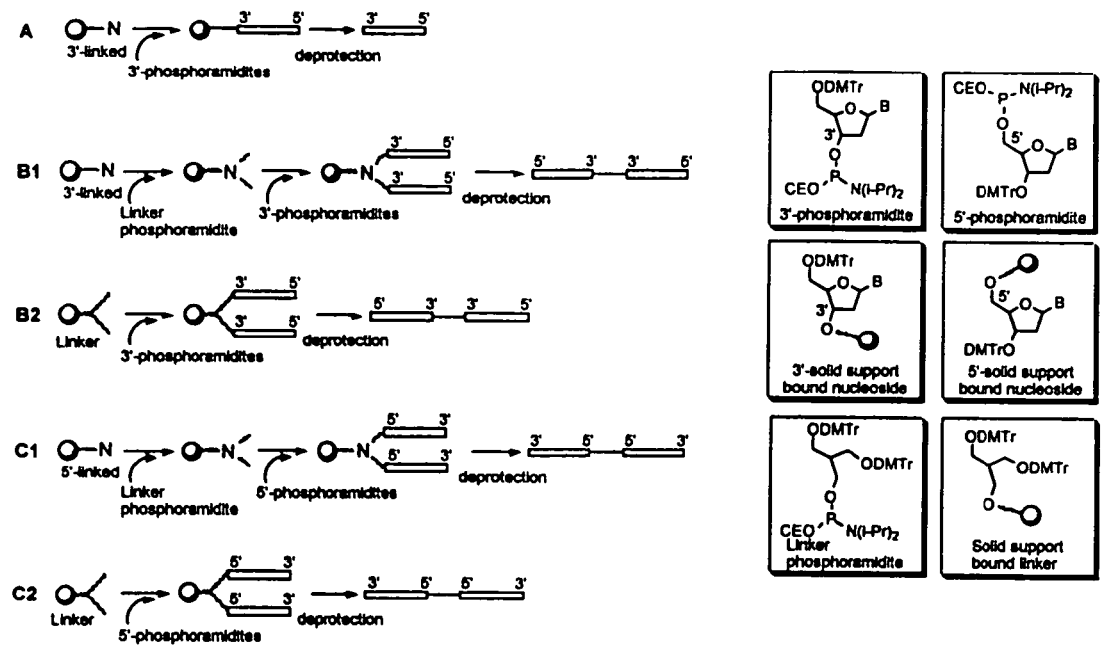
FIG. 6 is a synthetic scheme for the parallel synthesis of immunomers of the invention. DMTr=4,4'-dimethoxytrityl; CE=cyanoethyl.
Figure 12:
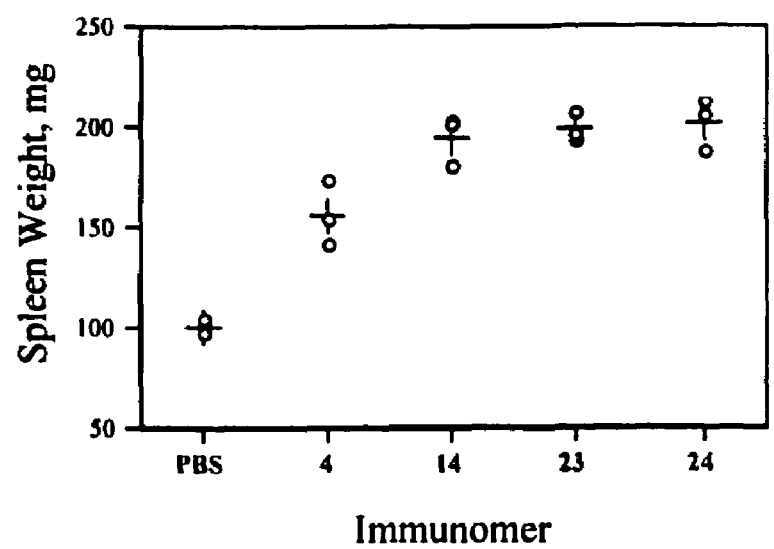
FIG. 12 is a graphic representation of BALB/c mouse spleen enlargement using oligonucleotides 4 and immunomers 14, 23, and 24. (SEQ ID NOS 4, 17, 23 and 24)

The immunomers of the invention may conveniently be synthesized using an automated synthesizer and phosphoramidite approach as schematically depicted in FIGS. 5 and 6, and further described in the Examples. In some embodiments, the immunomers are synthesized by a linear synthesis approach (see FIG. 5). As used herein, the term "linear synthesis" refers to a synthesis that starts at one end of the immunomer and progresses linearly to the other end. Linear synthesis permits incorporation of either identical or un-identical (in terms of length, base composition and/or chemical modifications incorporated) monomeric units into the immunomers.

An alternative mode of synthesis is "parallel synthesis", in which synthesis proceeds outward from a central linker moiety (see FIG. 6). A solid support attached linker can be used for parallel synthesis, as is described in U.S. Pat. No. 5,912,332. Alternatively, a universal solid support (such as phosphate attached controlled pore glass) support can be used.

Parallel synthesis of immunomers has several advantages over linear synthesis: (1) parallel synthesis permits the incorporation of identical monomeric units; (2) unlike in linear synthesis, both (or all) the monomeric units are synthesized at the same time, thereby the number of synthetic steps and the time required for the synthesis is the same as that of a monomeric unit; and (3) the reduction in synthetic steps improves purity and yield of the final immunomer product.

At the end of the synthesis by either linear synthesis or parallel synthesis protocols, the immunomers may conveniently be deprotected with concentrated ammonia solution or as recommended by the phosphoramidite supplier, if a modified nucleoside is incorporated. The product immunomer is preferably purified by reversed phase HPLC, detritylated, desalted and dialyzed.

Table 4A and Table 4B show representative immunomers according to the invention. Additional immunomers are found described in the Examples.

TABLE 4A

Examples of Immunomer Sequences

| (Oligo or Immunomer No.) SEQ ID NO. | Sequences and Modification (5'-3') |
|---|---|
| 1 | 5'-GAGAACGCTCGACCTT-3' |
| 2 | 5'-GAGAACGCTCGACCTT-3'-3'-TTCCAGCTCGCAAGAG-5' |
| 3 | 3'-TTCCAGCTCGCAAGAG-5'-5'-GAGAACGCTCGACCTT-3' |
| 4 | 5'-CTATCTGACGTTCTCTGT-3' |
| 5 | 5'-T-3'—[HNCO—$C_4H_8$-5'-CTATLTGACGTTCTCTGT-3' / HNCO—$C_4H_8$-5'-CTATLTGACGTTCTCTGT-3'] |
| 6 | 5'-CTATLTGACGTTCTCTGT-3'-$C_4H_8$—CONH / 5'-CTATLTGACGTTCTCTGT-3'-$C_4H_8$—CONH ]—3'-C-5' |
| 7 | 5'-CTATCTGACGTTCTCTGT-3'-$C_4H_8$—CONH / 5'-CTATCTGACGTTCTCTGT-3'-$C_4H_8$—CONH ]—3'-C-5' |
| 8 | 5'-CTATCTGACGTTCTCTGT-3' / 5'-CTATCTGACGTTCTCTGT-3' ]—3'-C-5' |
| 9 | 5'-CTATCTGAYGTTCTCTGT-3' / 5'-CTATCTGAYGTTCTCTGT-3' ]—3'-C-5' |
| 10 | 5'-CTATCTGACRTTCTCTGT-3' / 5'-CTATCTGACRTTCTCTGT-3' ]—3'-C-5' |
| 11 | 5'-CTALCTGAYGTTCTCTGT-3' / 5'-CTALCTGAYGTTCTCTGT-3' ]—3'-C-5' |
| 12 | 5'-CTALCTGACRTTCTCTGT-3' / 5'-CTALCTGACRTTCTCTGT-3' ]—3'-C-5' |
| 13 | 5'-CTGACGTTCTCTGT-3' |
| 14 | 5'-CTGACGTTCTCTGT-3' / 5'-CTGACGTTCTCTGT-3' ]—3'-C-5' |

TABLE 4A-continued

Examples of Immunomer Sequences

| (Oligo or Immunomer No.) SEQ ID NO. | Sequences and Modification (5'-3') |
|---|---|
| 15 | 5'-CTGAYGTTCTCTGT-3'  ⎤<br>5'-CTGAYGTTCTCTGT-3'  ⎦ ]–3'-C-5' |
| 16 | 5'-CTGACRTTCTCTGT-3'  ⎤<br>5'-CTGACRTTCTCTGT-3'  ⎦ ]–3'-C-5' |
| 17 | 5'-XXTGACGTTCTCTGT-3' |
| 18 | 5'-XXXTGACGTTCTCTGT-3'  ⎤<br>5'-XXXTGACGTTCTCTGT-3'  ⎦ ]–3'-C-5' |
| 19 | 5'-XXXTGAYGTTCTCTGT-3'  ⎤<br>5'-XXXTGAYGTTCTCTGT-3'  ⎦ ]–3'-C-5' |
| 20 | 5'-XXXTGACRTTCTCTGT-3'  ⎤<br>5'-XXXTGACRTTCTCTGT-3'  ⎦ ]–3'-C-5' |
| 21 | 5'-TCTGACGTTCT-3' |
| 22 | 5'-XXXTCTGACGTTCT-3'  ⎤<br>5'-XXXTCTGACGTTCT-3'  ⎦ ]–3'-C-5' |
| 23 | 5'-XXXTCTGAYGTTCT-3'  ⎤<br>5'-XXXTCTGAYGTTCT-3'  ⎦ ]–3'-C-5' |
| 24 | 5'-XXXTCTGACRTTCT-3'  ⎤<br>5'-XXXTCTGACRTTCT-3'  ⎦ ]–3'-C-5' |

⎡–NHCOC$_4$H$_8$–<br>⎣–NHCOC$_4$H$_8$–   = Symmetric longer branches;

] = Symmetric glycerol (short) branches

L = C3-alkyl linker;
X = 1',2'-dideoxyriboside;
Y = $^{5OH}$dC;
R = 7-deaza-dG

TABLE 4B

Examples of Immunomer Sequences

| SEQ ID NO. | Sequences (5'-3') | Modifications |
|---|---|---|
| 26 | 5'-TCTGTCG$_1$TTCT-X-TCTTG$_1$CTGTCT-5' | G$_1$ = 2'-deoxy-7-deazaguanosine; X = glycerol linker |
| 173 | 5'-TCTGTCG$_2$TTCT-X-TCTTG$_2$CTGTCT-5' | G$_2$ = arabinoguanosine; X = glycerol linker |
| 170 | 5'-TCTGTC$_1$GTTCT-X-TCTTGC$_1$TGTCT-5' | C$_1$ = 1-(2'-deoxy-β-D-ribofuranosyl)-2-oxo-7-deaza-8-methylpurine; X = glycerol linker |
| 174 | 5'-TCTGTC$_2$GTTCT-X-TGTTGC$_2$TGTCT-5' | C$_2$ = arabinocytidine; X = glycerol linker |
| 175 | 5'-TCTGTC$_3$GTTCT-X-TCTTGC$_3$TGTCT-5' | C$_3$ = 2'-deoxy-5-hydroxycytidine; X = glycerol linker |
| 176 | 5'-CTGTCG$_1$TTCTC-X-CTCTTG$_1$CTGTC-5' | G$_1$ = 2'-deoxy-7-deazaguanosine; X = glycerol linker |
| 171 | 5'-CTGTCG$_2$TTCTC-X-CTCTTG$_2$CTGTC-5' | G$_2$ = arabinoguanosine; X = glycerol linker |
| 177 | 5'-CTGTC$_1$GTTCTC-X-CTCTTGC$_1$TGTC-5' | C$_1$ = 1-(2'-deoxy-β-D-ribofuranosyl)-2-oxo-7-deaza-8-methylpurine; X = glycerol linker |
| 178 | 5'-CTGTC$_2$GTTCTC-X-CTCTTGC$_2$TGTC-5' | C$_2$ = arabinocytidine; X = glycerol linker |
| 179 | 5'-CTGTC$_3$GTTCTC-X-CTCTTGC$_3$TGTC-5' | C$_3$ = 2'-deoxy-5-hydroxycytidine; X = glycerol linker |
| 172 | 5'-TCG$_1$TCG$_1$TTCTG-X-GTCTTG$_1$CTG$_1$CT-5' | G$_1$ = 2'-deoxy-7-deazaguanosine; X = glycerol linker |
| 180 | 5'-TCG$_2$TCG$_2$TTCTG-X-GTCTTG$_2$CTG$_2$CT-5' | G$_2$ = arabinoguanosine; X = glycerol linker |
| 181 | 5'-TC$_1$GTC$_1$GTTCTG-X-GTCTTGC$_1$TGC$_1$T-5' | C$_1$ = 1-(2'-deoxy-β-D-ribofuranosyl)-2-oxo-7-deaza-8-methylpurine; X = glycerol linker |
| 182 | 5'-TC$_2$GTC$_2$GTTCTG-X-GTCTTGC$_2$TGC$_2$T-5' | C$_2$ = arabinocytidine; X = glycerol linker |

TABLE 4B-continued

Examples of Immunomer Sequences

| SEQ ID NO. | Sequences (5'-3') | Modifications |
|---|---|---|
| 183 | 5'-TC$_3$GTC$_3$GTTCTG-X-GTCTTGC$_3$TGC$_3$T-5' | C$_3$ = 2'-deoxy-5-hydroxycytidine; X = glycerol linker |
| 184 | 5'-TC$_1$G$_1$TC$_2$G$_2$TTCTG-X-GTCTTG$_3$C$_3$TG$_4$C$_4$T-5' | C1, C2, C3, and C4 are independently 2'-deoxycytidine, 1-(2'-deoxy-β-D-ribofuranosyl)-2-oxo-7-deaza-8-methylpurine, arabinocytidine, or 2'-deoxy-5-hydroxycytidine. G1, G2, G3, and G4 are independently 2'-deoxyguanosine, 2'-deoxy-7-deazaguanosine, or arabinoguanosine |

In a second aspect, the invention provides immunomodulatory oligonucleotide conjugates and immunomer conjugates, comprising an immunomodulatory oligonucleotide or an immunomer, as described above, and an antigen conjugated to the immunomer at a position other than the accessible 5' end. In some embodiments, the non-nucleotidic linker comprises an antigen, which is conjugated to the oligonucleotide. In some other embodiments, the antigen is conjugated to the oligonucleotide at a position other than its 3' end. In some embodiments, the antigen produces a vaccine effect.

The antigen is preferably selected from the group consisting of antigens associated with a pathogen, antigens associated with a cancer, antigens associated with an auto-immune disorder, and antigens associated with other diseases such as, but not limited to, veterinary or pediatric diseases. For purposes of the invention, the term "associated with" means that the antigen is present when the pathogen, cancer, auto-immune disorder, food allergy, respiratory allergy, asthma or other disease is present, but either is not present, or is present in reduced amounts, when the pathogen, cancer, auto-immune disorder, food allergy, respiratory allergy, or disease is absent.

The immunomodulatory oligonucleotide or immunomer is covalently linked to the antigen, or it is otherwise operatively associated with the antigen. As used herein, the term "operatively associated with" refers to any association that maintains the activity of both immunomer and antigen. Nonlimiting examples of such operative associations include being part of the same liposome or other such delivery vehicle or reagent. In embodiments wherein the immunomer is covalently linked to the antigen, such covalent linkage preferably is at any position on the immunomer other than an accessible 5' end of an immunostimulatory oligonucleotide. For example, the antigen may be attached at an internucleoside linkage or may be attached to the non-nucleotidic linker. Alternatively, the antigen may itself be the non-nucleotidic linker.

In a third aspect, the invention provides pharmaceutical formulations comprising an immunomodulatory oligonucleotide, immunomodulatory oligonucleotide conjugate, immunomer or immunomer conjugate according to the invention and a physiologically acceptable carrier. As used herein, the term "physiologically acceptable" refers to a material that does not interfere with the effectiveness of the immunomer and is compatible with a biological system such as a cell, cell culture, tissue, or organism. Preferably, the biological system is a living organism, such as a vertebrate.

As used herein, the term "carrier" encompasses any excipient, diluent, filler, salt, buffer, stabilizer, solubilizer, lipid, or other material well known in the art for use in pharmaceutical formulations. It will be understood that the characteristics of the carrier, excipient, or diluent will depend on the route of administration for a particular application. The preparation of pharmaceutically acceptable formulations containing these materials is described in, e.g., *Remington's Pharmaceutical Sciences*, 18th Edition, ed. A. Gennaro, Mack Publishing Co., Easton, Pa., 1990.

In a fourth aspect, the invention provides methods for generating an immune response in a vertebrate, such methods comprising administering to the vertebrate an immunomodulatory oligonucleotide, immunomodulatory oligonucleotide conjugate, immunomer or immunomer conjugate according to the invention. In some embodiments, the vertebrate is a mammal. For purposes of this invention, the term "mammal" is expressly intended to include humans. In preferred embodiments, the immunomer or immunomer conjugate is administered to a vertebrate in need of immunostimulation.

In the methods according to this aspect of the invention, administration of immunomodulatory oligonucleotide, immunomodulatory oligonucleotide conjugate, immunomer or immunomer conjugate can be by any suitable route, including, without limitation, parenteral, oral, sublingual, transdermal, topical, intranasal, aerosol, intraocular, intratracheal, intrarectal, vaginal, by gene gun, dermal patch or in eye drop or mouthwash form. Administration of the therapeutic compositions of immunomers can be carried out using known procedures at dosages and for periods of time effective to reduce symptoms or surrogate markers of the disease. When administered systemically, the therapeutic composition is preferably administered at a sufficient dosage to attain a blood level of immunomer from about 0.0001 micromolar to about 10 micromolar. For localized administration, much lower concentrations than this may be effective, and much higher concentrations may be tolerated. Preferably, a total dosage of immunomer ranges from about 0.001 mg per patient per day to about 200 mg per kg body weight per day. It may be desirable to administer simultaneously, or sequentially a therapeutically effective amount of one or more of the therapeutic compositions of the invention to an individual as a single treatment episode.

In certain preferred embodiments, immunomodulatory oligonucleotide, immunomodulatory oligonucleotide conjugate, immunomer or immunomer conjugate according to the invention are administered in combination with vaccines, antibodies, cytotoxic agents, allergens, antibiotics, antisense oligonucleotides, peptides, proteins, gene therapy vectors, DNA vaccines and/or adjuvants to enhance the specificity or magnitude of the immune response. In these embodiments, the immunomers of the invention can variously act as adjuvants and/or produce direct immunostimulatory effects.

Either the immunomodulatory oligonucleotide, immunomodulatory oligonucleotide conjugate, immunomer, immunomer conjugate or the vaccine, or both, may optionally be linked to an immunogenic protein, such as keyhole limpet hemocyanin (KLH), cholera toxin B subunit, or any other immunogenic carrier protein. Any of the plethora of adjuvants may be used including, without limitation, Freund's complete adjuvant, KLH, monophosphoryl lipid A (MPL), alum, and saponins, including QS-21, imiquimod, R848, or combinations thereof.

For purposes of this aspect of the invention, the term "in combination with" means in the course of treating the same disease in the same patient, and includes administering the immunomer and/or the vaccine and/or the adjuvant in any order, including simultaneous administration, as well as temporally spaced order of up to several days apart. Such combination treatment may also include more than a single administration of the immunomer, and/or independently the vaccine, and/or independently the adjuvant. The administration of the immunomer and/or vaccine and/or adjuvant may be by the same or different routes.

The methods according to this aspect of the invention are useful for model studies of the immune system. The methods are also useful for the prophylactic or therapeutic treatment of human or animal disease. For example, the methods are useful for pediatric and veterinary vaccine applications.

In a fifth aspect, the invention provides methods for therapeutically treating a patient having a disease or disorder, such methods comprising administering to the patient an immunomodulatory oligonucleotide, immunomodulatory oligonucleotide conjugate, immunomer or immunomer conjugate according to the invention. In various embodiments, the disease or disorder to be treated is cancer, an autoimmune disorder, airway inflammation, inflammatory disorders, allergy, asthma or a disease caused by a pathogen. Pathogens include bacteria, parasites, fungi, viruses, viroids and prions. Administration is carried out as described for the fourth aspect of the invention.

For purposes of the invention, the term "allergy" includes, without limitation, food allergies and respiratory allergies. The term "airway inflammation" includes, without limitation, asthma. As used herein, the term "autoimmune disorder" refers to disorders in which "self" proteins undergo attack by the immune system. Such term includes autoimmune asthma.

In any of the methods according to this aspect of the invention, the immunomodulatory oligonucleotide, immunomodulatory oligonucleotide conjugate, immunomer or immunomer conjugate can be administered in combination with any other agent useful for treating the disease or condition that does not diminish the immunostimulatory effect of the immunomer. For example, in the treatment of cancer, it is contemplated that the immunomodulatory oligonucleotide, immunomodulatory oligonucleotide conjugate, immunomer or immunomer conjugate may be administered in combination with a chemotherapeutic compound.

The examples below are intended to further illustrate certain preferred embodiments of the invention, and are not intended to limit the scope of the invention.

EXAMPLES

Example 1
Synthesis of Oligonucleotides Containing Immunomodulatory Moieties

Oligonucleotides were synthesized on a 1 μmol scale using an automated DNA synthesizer (Expedite 8909; PerSeptive Biosystems, Framingham, Mass.), following the linear synthesis or parallel synthesis procedures outlined in FIGS. 5 and 6.

Deoxyribonucleoside phosphoramidites were obtained from Applied Biosystems (Foster City, Calif.). 1',2'-dideoxyribose phosphoramidite, propyl-1-phosphoramidite, 2-deoxyuridine phosphoramidite, 1,3-bis-[5-(4,4'-dimethoxytrityl)pentylamidyl]-2-propanol phosphoramidite and methyl phosponamidite were obtained from Glen Research (Sterling, Va.). β-L-2'-deoxyribonucleoside phosphoramidite, α-2'-deoxyribonucleoside phosphoramidite, mono-DMT-glycerol phosphoramidite and di-DMT-glycerol phosphoramidite were obtained from ChemGenes (Ashland, Mass.). (4-Aminobutyl)-1,3-propanediol phosphoramidite was obtained from Clontech (Palo Alto, Calif.). Arabinocytidine phosphoramidite, arabinoguanosine, arabinothymidine and arabinouridine were obtained from Reliable Pharmaceutical (St. Louis, Mo.). Arabinoguanosine phosphoramidite, arabinothymidine phosphoramidite and arabinouridine phosphoramidite were synthesized at Hybridon, Inc. (Cambridge, Mass.) (Noronha et al. (2000) *Biochem.,* 39:7050-7062).

All nucleoside phosphoramidites were characterized by $^{31}P$ and $^1H$ NMR spectra. Modified nucleosides were incorporated at specific sites using normal coupling cycles. After synthesis, oligonucleotides were deprotected using concentrated ammonium hydroxide and purified by reverse phase HPLC, followed by dialysis. Purified oligonucleotides as sodium salt form were lyophilized prior to use. Purity was tested by CGE and MALDI-TOF MS.

Example 2
Analysis of Spleen Cell Proliferation

In vitro analysis of splenocyte proliferation was carried out using standard procedures as described previously (see, e.g., Zhao et al., Biochem Pharma 51:173-182 (1996)). The results are shown in FIG. 8A. These results demonstrate that at the higher concentrations, Immunomer 6, having two accessible 5' ends results in greater splenocyte proliferation than does Immunomer 5, having no accessible 5' end or Oligonucleotide 4, with a single accessible 5' end. Immunomer 6 also causes greater splenocyte proliferation than the LPS positive control.

Example 3

In Vivo Splenomegaly Assays

To test the applicability of the in vitro results to an in vivo model, selected oligonucleotides were administered to mice and the degree of splenomegaly was measured as an indicator of the level of immunostimulatory activity. A single dose of 5 mg/kg was administered to BALB/c mice (female, 4-6 weeks old, Harlan Sprague Dawley Inc, Baltic, Conn.) intraperitoneally. The mice were sacrificed 72 hours after oligonucleotide administration, and spleens were harvested and weighed. The results are shown in FIG. 8B. These results demonstrate that Immunomer 6, having two accessible 5' ends, has a far greater immunostimulatory effect than do Oligonucleotide 4 or Immunomer 5.

Example 4

Cytokine Analysis

The secretion of IL-12 and IL-6 in vertebrate cells, preferably BALB/c mouse spleen cells or human PBMC, was measured by sandwich ELISA. The required reagents including cytokine antibodies and cytokine standards were purchased form PharMingen, San Diego, Calif. ELISA plates (Costar) were incubated with appropriate antibodies at 5 μg/mL in PBSN buffer (PBS/0.05% sodium azide, pH 9.6) overnight at 4° C. and then blocked with PBS/1% BSA at 37° C. for 30 minutes. Cell culture supernatants and cytokine standards were appropriately diluted with PBS/10% FBS, added to the plates in triplicate, and incubated at 25° C. for 2 hours. Plates were overlaid with 1 μg/mL appropriate biotinylated antibody and incubated at 25° C. for 1.5 hours. The plates were then washed extensively with PBS-T Buffer (PBS/0.05% Tween 20) and further incubated at 25° C. for 1.5 hours after adding streptavidin conjugated peroxidase (Sigma, St. Louis, Mo.). The plates were developed with Sure Blue™ (Kirkegaard and Perry) chromogenic reagent and the reaction was terminated by adding Stop Solution (Kirkegaard and Perry). The color change was measured on a Ceres 900 HDI Spectrophotometer (Bio-Tek Instruments). The results are shown in Table 5A below.

Human peripheral blood mononuclear cells (PBMCs) were isolated from peripheral blood of healthy volunteers by Ficoll-Paque density gradient centrifugation (Histopaque-1077, Sigma, St. Louis, Mo.). Briefly, heparinized blood was layered onto the Histopaque-1077 (equal volume) in a conical centrifuge and centrifuged at 400×g for 30 minutes at room temperature. The buffy coat, containing the mononuclear cells, was removed carefully and washed twice with isotonic phosphate buffered saline (PBS) by centrifugation at 250×g for 10 minutes. The resulting cell pellet was then resuspended in RPMI 1640 medium containing L-glutamine (MediaTech, Inc., Herndon, Va.) and supplemented with 10% heat inactivated FCS and penicillin-streptomycin (100 U/ml). Cells were cultured in 24 well plates for different time periods at $1 \times 10^6$ cells/ml/well in the presence or absence of oligonucleotides. At the end of the incubation period, supernatants were harvested and stored frozen at −70° C. until assayed for various cytokines including IL-6 (BD Pharmingen, San Diego, Calif.), IL-10 (BD Pharmingen), IL-12 (BioSource International, Camarillo, Calif.), IFN-α (BioSource International) and -γ (BD Pharmingen) and TNF-α (BD Pharmingen) by sandwich ELISA. The results are shown in Table 5 below.

In all instances, the levels of IL-12 and IL-6 in the cell culture supernatants were calculated from the standard curve constructed under the same experimental conditions for IL-12 and IL-6, respectively. The levels of IL-10, IFN-gamma and TNF-α in the cell culture supernatants were calculated from the standard curve constructed under the same experimental conditions for IL-10, IFN-gamma and TNF-α, respectively.

TABLE 5

Immunomer Structure and Immunostimulatory Activity in Human PBMC Cultures

| (Oligo No.) SEQ ID NO. | Sequences and Modification (5'-3') | Oligo Length/ or Each Chain | IL-12 (pg/mL) D1 | IL-12 (pg/mL) D2 | IL-6 (pg/mL) D1 | IL-6 (pg/mL) D2 |
|---|---|---|---|---|---|---|
| 25 | 5'-CTATCTGTCGTTCTCTGT-3' | 18mer (PS) | 184 | 332 | 3077 | 5369 |
| 26 | 5'-TCTGTCR$_1$TTCT-3'↘<br>　　　　　　　　　X$_1$<br>5'-TCTGTCR$_1$TTCT-3'↗ | 11mer (PS) | 237 | 352 | 3724 | 4892 |

| (Oligo No.) SEQ ID NO. | Sequences and Modification (5'-3') | Oligo Length/ or Each Chain | IL-10 (pg/mL) D1 | IL-10 (pg/mL) D2 | IFN-γ (pg/mL) D1 | IFN-γ (pg/mL) D2 |
|---|---|---|---|---|---|---|
| 25 | 5'-CTATCTGTCGTTCTCTGT-3' | 18mer (PS) | 37 | 88 | 125 | 84 |
| 26 | 5'-TCTGTCR$_1$TTCT-3'↘<br>　　　　　　　　　X$_1$<br>5'-TCTGTCR$_1$TTCT-3'↗ | 11mer (PS) | 48 | 139 | 251 | 40 |

| (Oligo No.) SEQ ID NO. | Sequences and Modification (5'-3') | Oligo Length/ or Each Chain | TNF-α (pg/mL) D1 | TNF-α (pg/mL) D2 |
|---|---|---|---|---|
| 25 | 5'-CTATCTGTCGTTCTCTGT-3' | 18mer (PS) | 537 | nt |
| 26 | 5'-TCTGTCR$_1$TTCT-3'↘<br>　　　　　　　　　X$_1$<br>5'-TCTGTCR$_1$TTCT-3'↗ | 11mer (PS) | 681 | nt |

D1 and D2 are donors 1 and 2.

TABLE 5A

Immunomer Structure and Immunostimulatory Activity in BALB/c Mouse Spleen Cell Cultures

| (Oligo No.) SEQ ID NO. | Sequences and Modification (5'-3') | Oligo Length/ or Each Chain | IL-12 (pg/mL) 3 µg/mL | IL-6 (pg/mL) 10 µg/mL |
|---|---|---|---|---|
| 26 | 5'-TCTGTC$R_1$TTCT-3'<br>    $\searrow X_1$<br>5'-TCTGTC$R_1$TTCT-3'$\nearrow$ | 11mer (PS) | 870 | 10670 |
| 27 | 5'-TCTGTC$R_2$TTCT-3'<br>    $\searrow X_1$<br>5'-TCTGTC$R_2$TTCT-3'$\nearrow$ | 11mer (PS) | 1441 | 7664 |
| 28 | 5'-TCTGT$Y_2R_2$TTCT-3'<br>    $\searrow X_1$<br>5'-TCTGT$Y_2R_2$TTCT-3'$\nearrow$ | 11mer (PS) | 1208 | 1021 |
| 29 | 5'-XXTCTGTC$R_1$TTCT-3'<br>    $\searrow X_1$<br>5'-XXTCTGTC$R_1$TTCT-3'$\nearrow$ | 11mer (PS) | 162 | 1013 |
| 30 | 5'-CTGTC$R_2$TTCTCTGT-3'<br>    $\searrow X_1$<br>5'-CTGTC$R_2$TTCTCTGT-3'$\nearrow$ | 14mer (PO) | 264 | 251 |
| 31 | 5'-CTGT$Y_2R_2$TTCTCTGT-3'<br>    $\searrow X_1$<br>5'-CTGT$Y_2R_2$TTCTCTGT-3'$\nearrow$ | 14mer (PO) | 149 | 119 |
| 32 | 5'-TCTGAC$R_1$TTCT-3'<br>    $\searrow X_1$<br>5'-TCTGAC$R_1$TTCT-3'$\nearrow$ | 11mer (PS) | 2520 | 9699 |
| 33 | 5'-XXTCTGAC$R_1$TTCT-3'<br>    $\searrow X_1$<br>5'-XXTCTGAC$R_1$TTCT-3'$\nearrow$ | 11mer (PS) | 2214 | 16881 |
| 34 | 5'-TCTGAC$R_2$TTCT-3'<br>    $\searrow X_1$<br>5'-TCTGAC$R_2$TTCT-3'$\nearrow$ | 11mer (PS) | 3945 | 10766 |
| 35 | 5'-TCTGA$Y_2R_2$TTCT-3'<br>    $\searrow X_1$<br>5'-TCTGA$Y_2R_2$TTCT-3'$\nearrow$ | 11mer (PS) | 2573 | 19411 |
| 36 | 5'-CTGA$Y_2$GTTCTCTGT-3'<br>    $\searrow X_1$<br>5'-CTGA$Y_2$GTTCTCTGT-3'$\nearrow$ | 14mer (PO) | 2699 | 408 |
| 37 | 5'-CTGAC$R_2$TTCTCTGT-3'<br>    $\searrow X_1$<br>5'-CTGAC$R_2$TTCTCTGT-3'$\nearrow$ | 14mer (PO) | 839 | 85 |
| 38 | 5'-CTGA$Y_2R_2$TTCTCTGT-3'<br>    $\searrow X_1$<br>5'-CTGA$Y_2R_2$TTCTCTGT-3'$\nearrow$ | 14mer (PO) | 143 | 160 |

Normal phase represents a phosphorothioate linkage; Italic phase represents a phosphodiester linkage.

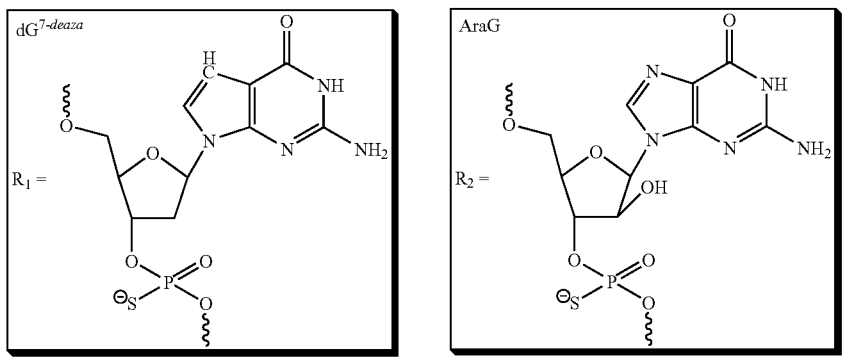

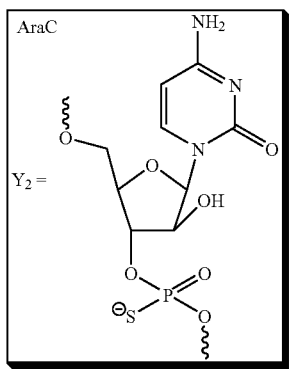

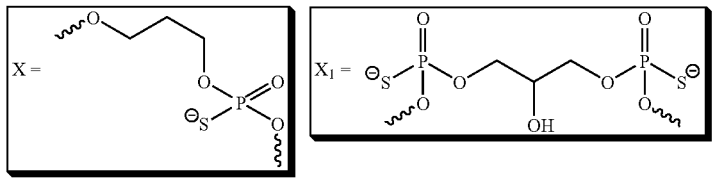

In addition, the results shown in FIGS. 7A-C demonstrate that Oligonucleotide 2, with two accessible 5' ends elevates IL-12 and IL-6, but not IL-10 at lower concentrations than Oligonucleotides 1 or 3, with one or zero accessible 5' ends, respectively.

Example 5

Effect of Chain Length on Immunostimulatory Activity of Immunomers

In order to study the effect of length of the oligonucleotide chains, immunomers containing 18, 14, 11, and 8 nucleotides in each chain were synthesized and tested for immunostimulatory activity, as measured by their ability to induce secretion of the cytokines IL-12 and IL-6 in BALB/c mouse spleen cell cultures (Tables 6-8). In this, and all subsequent examples, cytokine assays were carried out in BALB/c spleen cell cultures as described in Example 4.

TABLE 6

Immunomer Structure and Immunostimulatory Activity

| (Oligo No.) SEQ ID NO. | Sequences and Modification (5'-3') | Oligo Length/ or Each Chain | IL-12 (pg/mL) @ 0.3 µg/mL | IL-6 (pg/mL) @ 0.3 µg/mL |
|---|---|---|---|---|
| 4 | 5'-CTATCTGACGTTCTCTGT-3' | 18mer | 1802 | 176 |
| 39 | 5'-CTATCTGACGTTCTCTGT-3'<br>5'-CTATCTGACGTTCTCTGT-3' ┤3'-T-5' | 18mer | 1221 | 148 |
| 40 | 5'-CTGACGTTCTCTGT-3'<br>5'-CTGACGTTCTCTGT-3' ┤3'-T-5' | 14mer | 2107 | 548 |
| 41 | 5'-TCTGACGTTCT-3'<br>5'-TCTGACGTTCT-3' ┤3'-T-5' | 11mer | 3838 | 1191 |
| 42 | 5'-GACGTTCT-3'<br>5'-GACGTTCT-3' ┤3'-T-5' | 8mer | 567 | 52 |

TABLE 7

Immunomer Structure and Immunostimulatory Activity

| (Oligo No.) SEQ ID NO. | Sequences and Modification (5'-3') | Oligo Length/ or Each Chain | IL-12 (pg/mL) 1 µg/mL | IL-6 (pg/mL) 1 µg/mL |
|---|---|---|---|---|
| 25 | 5'-CTATCTGTCGTTCTCTGT-3' | 18mer | 291 | 65 |
| 43 | 5'-CTATCTGTCGTTCTCTGT-3'<br>5'-CTATCTGTCGTTCTCTGT-3' ┤3'-T-5' | 18mer | 430 | 39 |
| 44 | 5'-CTGTCGTTCTCTGT-3'<br>5'-CTGTCGTTCTCTGT-3' ┤3'-T-5' | 14mer | 813 | 59 |
| 45 | 5'-CTGTCGTTCTCT-3'<br>5'-CTGTCGTTCTCT-3' ┤3'-T-5' | 12mer | 1533 | 123 |
| 46 | 5'-TCTGTCGTTCT-3'<br>5'-TCTGTCGTTCT-3' ┤3'-T-5' | 11mer | 2933 | 505 |
| 47 | 5'-GTCGTTCT-3'<br>5'-GTCGTTCT-3' ┤3'-T-5' | 8mer | 1086 | 26 |
| 48 | 5'-GTCGTTC-3'<br>5'-GTCGTTC-3' ┤3'-T-5' | 7mer | 585 | 34 |
| 49 | 5'-GTCGTT-3'<br>5'-GTCGTT-3' ┤3'-T-5' | 6mer | 764 | 76 |
| 50 | 5'-TCGTT-3'<br>5'-TCGTT-3' ┤3'-T-5' | 5mer | 28 | 29 |

TABLE 8

Immunomer Structure and Immunostimulatory Activity

| (Oligo No.) SEQ ID NO. | Sequences and Modification (5'-3') | Oligo Length/ or Each Chain | IL-12 (pg/mL) 1 µg/mL | IL-6 (pg/mL) 1 µg/mL |
|---|---|---|---|---|
| 51 | 5'-CTCACTTTCGTTCTCTGT-3' | 18mer | 91 | 73 |
| 52 | 5'-CTCACTTTCGTTCTCTGT-3'⌉<br>⎣3'-T-5'<br>5'-CTCACTTTCGTTCTCTGT-3'⌋ | 18mer | 502 | 99 |
| 53 | 5'-CTTTCGTTCTCTGT-3'⌉<br>⎣3'-T-5'<br>5'-CTTTCGTTCTCTGT-3'⌋ | 14mer | 683 | 119 |
| 54 | 5'-CTTTCGTTCTCT-3'⌉<br>⎣3'-T-5'<br>5'-CTTTCGTTCTCT-3'⌋ | 12mer | 633 | 102 |
| 55 | 5'-TTCGTTCT-3'⌉<br>⎣3'-T-5'<br>5'-TTCGTTCT-3'⌋ | 8mer | 687 | 243 |
| 56 | 5'-TCGTTCT-3'⌉<br>⎣3'-T-5'<br>5'-TCGTTCT-3'⌋ | 7mer | 592 | 1252 |

The results suggest that the immunostimulatory activity of immunomers increased as the length of the oligonucleotide chains is decreased from 18-mers to 7-mers. Immunomers having oligonucleotide chain lengths as short as 6-mers or 5-mers showed immunostimulatory activity comparable to that of the 18-mer oligonucleotide with a single 5' end. However, immunomers having oligonucleotide chain lengths as short as 6-mers or 5-mers have increased immunostimulatory activity when the linker is in the length of from about 2 angstroms to about 200 angstroms.

Example 6

Immunostimulatory Activity of Immunomers Containing a Non-Natural Pyrimidine or Non-Natural Purine Nucleoside As shown in Tables 9-11, immunostimulatory activity was maintained for immunomers of various lengths having a non-natural pyrimidine nucleoside or non-natural purine nucleoside in the immunostimulatory dinucleotide motif.

TABLE 9

Immunomer Structure and Immunostimulatory Activity

| (Oligo No.) SEQ ID NO. | Sequences and Modification (5'-3') | Oligo Length/ or Each Chain | IL-12 (pg/mL) @ 3 µg/mL | IL-6 (pg/mL) @ 3 µg/mL |
|---|---|---|---|---|
| 51 | 5'-CTCACTTTCGTTCTCTGT-3' | 18mer | 404 | 348 |
| 57 | 5'-TCTTTYGTTCT-3'⌉<br>⎣3'-T-5'<br>5'-TCTTTYGTTCT-3'⌋ | 11mer | 591 | 365 |
| 58 | 5'-TCTTTCRTTCT-3'⌉<br>⎣3'-T-5'<br>5'-TCTTTCRTTCT-3'⌋ | 11mer | 303 | 283 |

TABLE 9-continued

Immunomer Structure and Immunostimulatory Activity

| (Oligo No.) SEQ ID NO. | Sequences and Modification (5'-3') | Oligo Length/ or Each Chain | IL-12 (pg/mL) @ 3 µg/mL | IL-6 (pg/mL) @ 3 µg/mL |
|---|---|---|---|---|
| 59 | 5'-TTYGTTCT-3' ⌐<br>                              ⊢3'-T-5'<br>5'-TTYGTTCT-3' ⌐ | 8mer | 55 | 66 |
| 60 | 5'-TTCRTTCT-3' ⌐<br>                              ⊢3'-T-5'<br>5'-TTCRTTCT-3' ⌐ | 8mer | 242 | 143 |

Y = 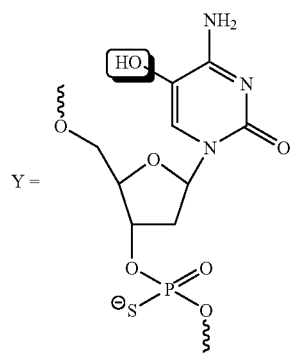

R = 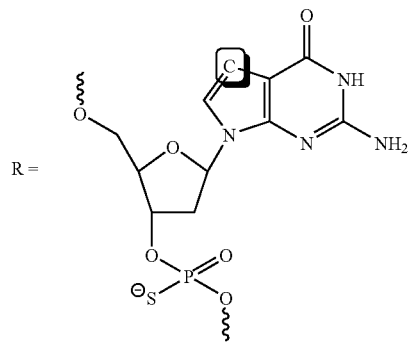

TABLE 10

Immunomer Structure and Immunostimulatory Activity

| (Oligo No.) SEQ ID NO. | Sequences and Modification (5'-3') | Oligo Length/ or Each Chain | IL-12 (pg/mL) 3 µg/mL | IL-6 (pg/mL) 3 µg/mL |
|---|---|---|---|---|
| 25 | 5'-CTATCTGTCGTTCTCTGT-3' | 18mer | 379 | 339 |
| 61 | 5'-TCTGTYGTTCT-3' ⌐<br>                              ⊢3'-T-5'<br>5'-TCTGTYGTTCT-3' ⌐ | 11mer | 1127 | 470 |
| 62 | 5'-TCTGTCRTTCT-3' ⌐<br>                              ⊢3'-T-5'<br>5'-TCTGTCRTTCT-3' ⌐ | 11mer | 787 | 296 |
| 63 | 5'-GTYGTTCT-3' ⌐<br>                              ⊢3'-T-5'<br>5'-GTYGTTCT-3' ⌐ | 8mer | 64 | 126 |
| 64 | 5'-GTCRTTCT-3' ⌐<br>                              ⊢3'-T-5'<br>5'-GTCRTTCT-3' ⌐ | 8mer | 246 | 113 |

TABLE 10-continued

Immunomer Structure and Immunostimulatory Activity

| (Oligo No.) SEQ ID NO. | Sequences and Modification (5'-3') | Oligo Length/ or Each Chain | IL-12 (pg/mL) 3 μg/mL | IL-6 (pg/mL) 3 μg/mL |
|---|---|---|---|---|

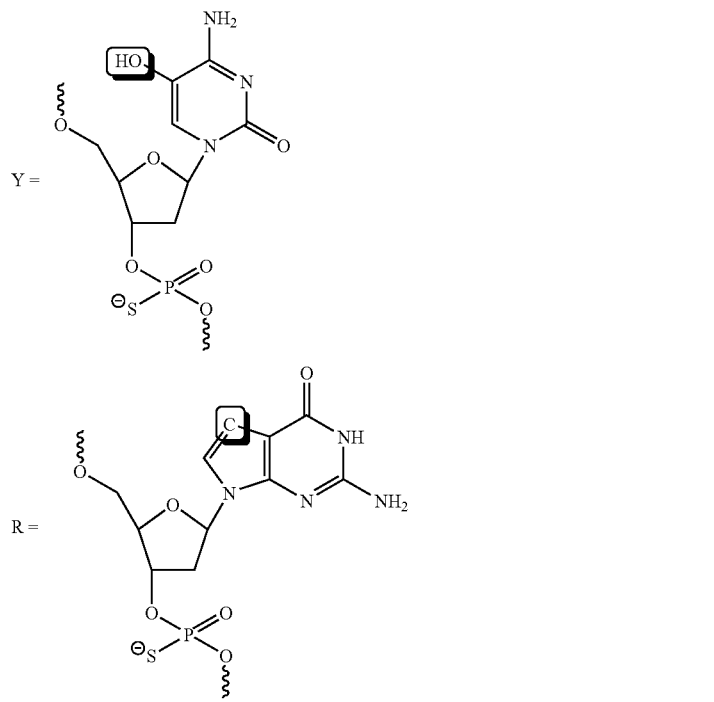

TABLE 11

Immunomer Structure and Immunostimulatory Activity

| (Oligo No.) SEQ ID NO. | Sequences and Modification (5'-3') | Oligo Length/ or Each Chain | IL-12 (pg/mL) 3 μg/mL | IL-6 (pg/mL) 3 μg/mL |
|---|---|---|---|---|
| 4 | 5'-CTATCTGACGTTCTCTGT-3' | 18mer | 1176 | 1892 |
| 65 | 5'-CTATCTGAYGTTCTCTGT-3'⎤<br>⎦3'-T-5'<br>5'-CTATCTGAYGTTCTCTGT-3'⎦ | 18mer | 443 | 192 |
| 66 | 5'-CTATCTGACRTTCTCTGT-3'⎤<br>⎦3'-T-5'<br>5'-CTATCTGACRTTCTCTGT-3'⎦ | 18mer | 627 | 464 |
| 67 | 5'-CTGAYGTTCTCTGT-3'⎤<br>⎦3'-T-5'<br>5'-CTGAYGTTCTCTGT-3'⎦ | 14mer | 548 | 152 |
| 68 | 5'-CTGACRTTCTCTGT-3'⎤<br>⎦3'-T-5'<br>5'-CTGACRTTCTCTGT-3'⎦ | 14mer | 1052 | 1020 |
| 69 | 5'-TCTGAYGTTCT-3'⎤<br>⎦3'-T-5'<br>5'-TCTGAYGTTCT-3'⎦ | 11mer | 2050 | 2724 |

TABLE 11-continued
Immunomer Structure and Immunostimulatory Activity
| (Oligo No.) SEQ ID NO. | Sequences and Modification (5'-3') | Oligo Length/ or Each Chain | IL-12 (pg/mL) 3 µg/mL | IL-6 (pg/mL) 3 µg/mL |
|---|---|---|---|---|
| 70 | 5'-TCTGACRTTCT-3'⌐<br>  ├3'-T-5'<br>5'-TCTGACRTTCT-3'⌐ | 11mer | 1780 | 1741 |
| 71 | 5'-GAYGTTCT-3'⌐<br>  ├3'-T-5'<br>5'-GAYGTTCT-3'⌐ | 8mer | 189 | 55 |
| 72 | 5'-GACRTTCT-3'⌐<br>  ├3'-T-5'<br>5'-GACRTTCT-3'⌐ | 8mer | 397 | 212 |
Y = 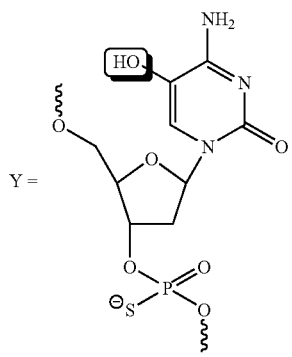
R = 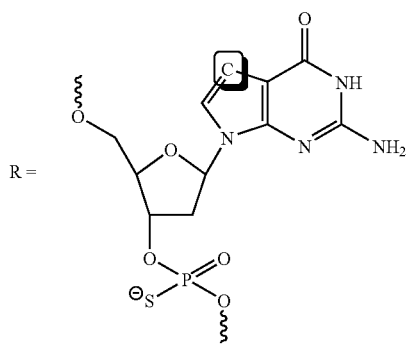

Example 7

Effect of the Linker on Immunostimulatory Activity

In order to examine the effect of the length of the linker connecting the two oligonucleotides, immunomers that contained the same oligonucleotides, but different linkers were synthesized and tested for immunostimulatory activity. The results shown in Table 12 suggest that linker length plays a role in the immunostimulatory activity of immunomers. The best immunostimulatory effect was achieved with C3- to C6-alkyl linkers or abasic linkers having interspersed phosphate charges.

TABLE 12

Immunomer Structure and Immunostimulatory Activity

| (Oligo No.) SEQ ID NO. | Sequences and Modification (5'-3') | Oligo Length/ or Each Chain | IL-12 (pg/mL) 0.3 μg/mL | IL-6 (pg/mL) 1 μg/mL |
|---|---|---|---|---|
| 4 | 5'-CTATCTGACGTTCTCTGT-3' | 18mer | 257 | 635 |
| 73 | 5'-CTGACGTTCT-3'⟩X₁ / 5'-CTGACGTTCT-3' | 10mer | 697 | 1454 |
| 74 | 5'-CTGACGTTCT-3'⟩X₂ / 5'-CTGACGTTCT-3' | 10mer | 1162 | 669 |
| 75 | 5'-CTGACGTTCT-3'⟩X₃ / 5'-CTGACGTTCT-3' | 10mer | 1074 | 1375 |
| 76 | 5'-CTGACGTTCT-3'⟩X₄ / 5'-CTGACGTTCT-3' | 10mer | 563 | 705 |
| 77 | 5'-CTGACGTTCT-3'⟩X₅ / 5'-CTGACGTTCT-3' | 10mer | 264 | 543 |
| 78 | 5'-CTGACGTTCT-3'⟩X₆ / 5'-CTGACGTTCT-3' | 10mer | 1750 | 2258 |
| 79 | 5'-CTGACGTTCT-3'⟩(X₃psX₃) / 5'-CTGACGTTCT-3' | 10mer | 2255 | 2034 |
| 80 | 5'-CTGACGTTCT-3'⟩(X₃psX₃psX₃) / 5'-CTGACGTTCT-3' | 10mer | 1493 | 1197 |
| 81 | 5'-CTGACGTTCT-3'⟩(X₆psX₆) / 5'-CTGACGTTCT-3' | 10mer | 3625 | 2642 |
| 82 | 5'-CTGACGTTCT-3'⟩(X₆psX₆psX₆) / 5'-CTGACGTTCT-3' | 10mer | 4248 | 2988 |
| 83 | 5'-CTGACGTTCT-3'⟩PO₃S / 5'-CTGACGTTCT-3' | 10mer | 1241 | 1964 |

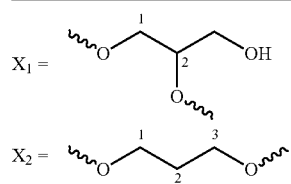

TABLE 12-continued

Immunomer Structure and Immunostimulatory Activity

| (Oligo No.) SEQ ID NO. | Sequences and Modification (5'-3') | Oligo Length/ or Each Chain | IL-12 (pg/mL) 0.3 µg/mL | IL-6 (pg/mL) 1 µg/mL |
|---|---|---|---|---|

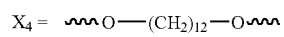

$X_3 =$ 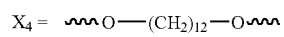

$X_4 =$ ~O—(CH$_2$)$_{12}$—O~

$X_5 =$ 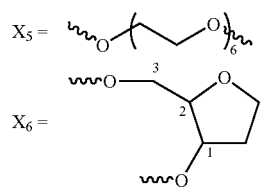

$X_6 =$ 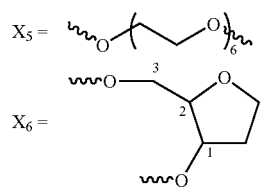

Example 8

Effect of Oligonucleotide Backbone on Immunostimulatory Activity

In general, immunostimulatory oligonucleotides that contain natural phosphodiester backbones are less immunostimulatory than are the same length oligonucleotides with a phosphorothioate backbones. This lower degree of immunostimulatory activity could be due in part to the rapid degradation of phosphodiester oligonucleotides under experimental conditions. Degradation of oligonucleotides is primarily the result of 3'-exonucleases, which digest the oligonucleotides from the 3' end. The immunomers of this example do not contain a free 3' end. Thus, immunomers with phosphodiester backbones should have a longer half life under experimental conditions than the corresponding monomeric oligonucleotides, and should therefore exhibit improved immunostimulatory activity. The results presented in Table 13 demonstrate this effect, with Immunomers 84 and 85 exhibiting immunostimulatory activity as determined by cytokine induction in BALB/c mouse spleen cell cultures.

TABLE 13

Immunomer Structure and Immunostimulatory Activity

| (Oligo No.) SEQ ID NO. | Sequences and Modification (5'-3') | Oligo Length/ or Each Chain | IL-12 (pg/mL) 0.3 µg/mL | IL-6 (pg/mL) 1 µg/mL |
|---|---|---|---|---|
| 4 | 5'-CTATCTGACGTTCTCTGT-3' | 18mer | 225 | 1462 |
| 84 | 5'-CTGACGTTCTCTGT-3'⌉<br>              ⌐3'-T-5' (PO)<br>5'-CTGACGTTCTCTGT-3'⌋ | 14mer | 1551 | 159 |
| 85 | 5'-LLCTGACGTTCTCTGT-3'⌉<br>              ⌐3'-T-5' (PO)<br>5'-LLCTGACGTTCTCTGT-3'⌋ | 14mer | 466 | 467 |

L = C3-Linker

Example 9

Synthesis of Immunomers 73-92

Oligonucleotides were synthesized on 1 µmol scale using an automated DNA synthesizer (Expedite 8909 PerSeptive Biosystems). Deoxynucleoside phosphoramidites were obtained from Applied Biosystems (Foster City, Calif.). 7-Deaza-2'-deoxyguanosine phosphoramidite was obtained from Glen Research (Sterling Va.). 1,3-Bis-DMT-glycerol-CPG was obtained from ChemGenes (Ashland, Mass.). Modified nucleosides were incorporated into the oligonucleotides at specific site using normal coupling cycles. After the synthesis, oligonucleotides were deprotected using concentrated ammonium hydroxide and purified by reversed-phase HPLC, followed by dialysis. Purified oligonucleotides as sodium salt form were lyophilized prior to use. Purity of oligonucleotides was checked by CGE and MALDI-TOF MS (Bruker Proflex III MALDI-TOF Mass spectrometer).

Example 11

Immunomer Stability

Oligonucleotides were incubated in PBS containing 10% bovine serum at 37° C. for 4, 24 or 48 hours. Intact oligonucleotide was determined by capillary gel electrophoresis. The results are shown in Table 14.

(v/v) FCS and antibiotics (100 IU/mL of penicillin G/streptomycin). All other culture reagents were purchased from Mediatech (Gaithersburg, Md.).

ELISAs for IL-12 and IL-6. BALB/c mouse spleen or J774 cells were plated in 24-well dishes at a density of $5 \times 10^6$ or $1 \times 10^6$ cells/mL, respectively. The CpG DNA dissolved in TE buffer (10 mM Tris-HCl, pH 7.5, 1 mM EDTA) was added to a final concentration of 0.03, 0.1, 0.3, 1.0, 3.0, or 10.0 µg/mL to mouse spleen cell cultures and 1.0, 3.0, or 10.0 µg/mL to J774 cell cultures. The cells were then incubated at 37° C. for 24 hr and the supernatants were collected for ELISA assays. The experiments were performed two or three times for each CpG DNA in triplicate for each concentration.

The secretion of IL-12 and IL-6 was measured by sandwich ELISA. The required reagents, including cytokine antibodies and standards were purchased from PharMingen. ELISA plates (Costar) were incubated with appropriate antibodies at 5 µg/mL in PBSN buffer (PBS/0.05% sodium azide, pH 9.6) overnight at 4° C. and then blocked with PBS/1% BSA at 37° C. for 30 min. Cell culture supernatants and cytokine standards were appropriately diluted with PBS/1% BSA, added to the plates in triplicate, and incubated at 25° C. for 2 hr. Plates were washed and incubated with 1 µg/mL of appropriate biotinylated antibody and incubated at 25° C. for 1.5 hr. The plates were washed extensively with PBS/0.05% Tween 20

TABLE 14

Digestion of Oligonucleotides in 10% Bovine Serum PBS Solution

| (Oligo No.) SEQ ID NO. | Sequences and Modification (5'-3') | CE analysis of oligos (% intact) oligo remained after digestion) | | |
|---|---|---|---|---|
| | | after 4 h | After 24 h | after 48 h |
| 4 | 5-CTATCTGACGTTCTCTGT-3'/PS | 90.9 | 71.8 | 54.7 |
| 26 | (5'-TCTGTCGTTCT)$_2$S/PS (G = dG$^{deaza}$) | 97.1 | 91.0 | 88.1 |
| 86 | (5'-CTGTCGTTCTCTGT)$_2$S/PO | | 37.8 | 22.5 |
| 87 | (5'-XXCTGTCGTTCTCTGT)$_2$S/PO | 73.1 | 56.8 | 36.8 |
| 88 | (5'-UCTGTCGTTCTCTGT)$_2$S/PO | | 48.4 | 36.7 |

X = C3-Linker, U, C = 2'-OMe-ribonucleoside

Example 12

Effect of Accessible 5' Ends on Immunostimulatory Activity

BALB/c mouse (4-8 weeks) spleen cells were cultured in RPMI complete medium. Murine macrophage-like cells, J774 (American Type Culture Collection, 101801 University Boulevard, Manassas, Va. 20110-2209) were cultured in Dulbecco's modified Eagle's medium supplemented with 10% and then further incubated at 25° C. for 1.5 hr after the addition of streptavidine-conjugated peroxidase (Sigma). The plates were developed with Sure Blue™ (Kirkegaard and Perry) chromogenic reagent and the reaction was terminated by adding Stop Solution (Kirkegaard and Perry). The color change was measured on a Ceres 900 HDI Spectrophotometer (Bio-Tek Instruments) at 450 nm. The levels of IL-12 and IL-6 in the cell culture supernatants were calculated from the standard curve constructed under the same experimental conditions for IL-12 and IL-6, respectively.

The results are shown in Table 15.

TABLE 15

Phosphorothioate CpG DNA sequences and modifications used in the study[a]

| CpG DNA # SEQ ID NO. | Sequence | Length | 5'-end | 3'-end |
|---|---|---|---|---|
| 89 | 5'-TCCATGA<u>CG</u>TTCCTGATGC-3' | 19-mer | 1 | 1 |
| 90 | 5'-TCCATGA<u>CG</u>TTCCTGATGC-3'-b | 19-mer | 1 | blocked |
| 91 | 5'-TCCATGA<u>CG</u>TTCCTGATGC-3'-3'-g-5' | 20-mer | 2 | blocked |
| 92 | 5'-TCCATGA<u>CG</u>TTCCTGATGC-3'-3'-h-5' | 23-mer | 2 | blocked |
| 93 | 5'-TCCATGA<u>CG</u>TTCCTGATGC-3'-3'-i-5' | 27-mer | 2 | blocked |
| 94 | 5'-TCCATGA<u>CG</u>TTCCTGATGC-3'-3'-j-5' | 38-mer | 2 | blocked |
| 95 | b-5'-TCCATGA<u>CG</u>TTCCTGATGC-3' | 19-mer | blocked | 1 |
| 96 | 3'-c-5'-5'-TCCATGA<u>CG</u>TTCCTGATGC-3' | 20-mer | blocked | 2 |
| 97 | 3'-d-5'-5'-TCCATGA<u>CG</u>TTCCTGATGC-3' | 23-mer | blocked | 2 |
| 98 | 3'-e-5'-5'-TCCATGA<u>CG</u>TTCCTGATGC-3' | 27-mer | blocked | 2 |
| 99 | 3'-f-5'-5'-TCCATGA<u>CG</u>TTCCTGATGC-3' | 38-mer | blocked | 2 |
| 100 | 5'-TCCATGA<u>CG</u>TTCCTGATGC-3'-k | 19-mer | 1 | blocked |
| 101 | l-5'-TCCATGA<u>CG</u>TTCCTGATGC-3' | 19-mer | blocked | 1 |

[a]See Chart I for chemical structures b-l; 5'-CG-3' dinucleotide is shown underlined.

Chart 1

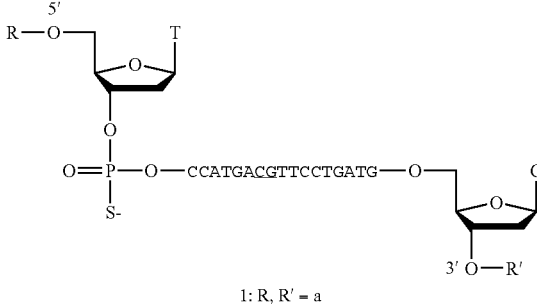

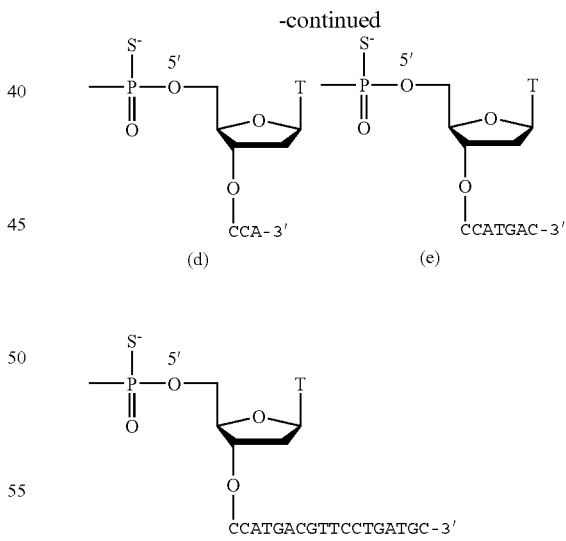

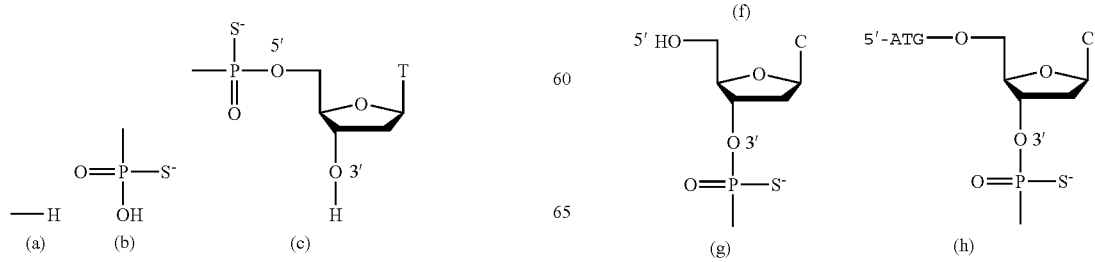

-continued

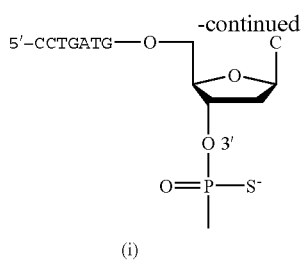

(i)

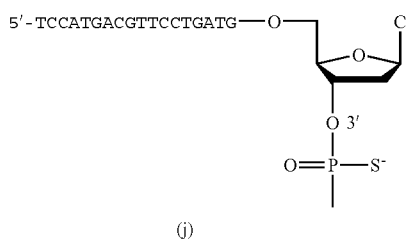

(j)

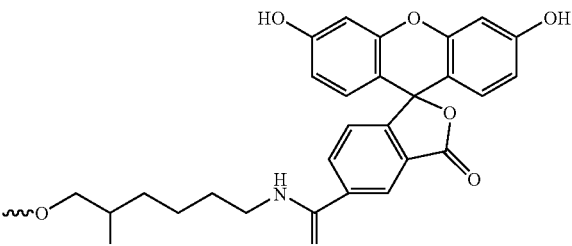

(k): X = CH$_2$OH;
(l): X = H.

TABLE 16

Induction of IL-12 and IL-6 secretion by CpG DNA-conjugates in BALB/c mice spleen cell cultures

| CpG DNA #[a] | IL-12 (pg/mL) ± SD | | | | | IL-6 (pg/mL) ± SD | | | | |
|---|---|---|---|---|---|---|---|---|---|---|
| | 0.1 μg/mL | 0.3 μg/mL | 1.0 μg/mL | 3.0 μg/mL | 10.0 μg/mL | 0.1 μg/mL | 0.3 μg/mL | 1.0 μg/mL | 3.0 μg/mL | 10.0 μ/mL |
| 89 | 991 ± 121 | 1820 ± 224 | 2391 ± 175 | 3507 ± 127 | 2615 ± 279 | 652 ± 48 | 2858 ± 180 | 13320 ± 960 | 18625 ± 1504 | 17229 ± 1750 |
| 90 | 526 ± 32 | 2100 ± 175 | 1499 ± 191 | 3019 ± 35 | 3489 ± 162 | 1387 ± 152 | 1426 ± 124 | 5420 ± 370 | 19096 ± 484 | 19381 ± 2313 |
| 91 | 1030 ± 11 | 1348 ± 102 | 2060 ± 130 | 3330 ± 130 | 3582 ± 259 | 923 ± 22 | 2542 ± 81 | 9054 ± 120 | 14114 ± 179 | 13693 ± 264 |
| 92 | 1119 ± 159 | 1726 ± 207 | 2434 ± 100 | 2966 ± 204 | 3215 ± 464 | 870 ± 146 | 1905 ± 56 | 7841 ± 350 | 17146 ± 1246 | 15713 ± 693 |
| 93 | 1175 ± 68 | 2246 ± 124 | 1812 ± 75 | 2388 ± 320 | 2545 ± 202 | 1152 ± 238 | 3499 ± 116 | 7142 ± 467 | 14064 ± 167 | 13566 ± 477 |
| 94 | 1087 ± 121 | 1705 ± 163 | 1797 ± 141 | 2522 ± 195 | 3054 ± 103 | 1039 ± 105 | 2043 ± 157 | 4848 ± 288 | 15527 ± 224 | 21021 ± 1427 |
| 95 | 1173 ± 107 | 2170 ± 155 | 2132 ± 58 | 2812 ± 203 | 3689 ± 94 | 807 ± 0.5 | 927 ± 0.5 | 3344 ± 0.5 | 10233 ± 0.5 | 9213 ± 0.5 |
| 96 | 866 ± 51 | 1564 ± 63 | 1525 ± 63 | 2666 ± 97 | 4030 ± 165 | 750 ± 63 | 1643 ± 30 | 5559 ± 415 | 11549 ± 251 | 11060 ± 651 |
| 97 | 227 ± 3 | 495 ± 96 | 1007 ± 68 | 897 ± 15 | 1355 ± 97 | 302 ± 18 | 374 ± 22 | 1000 ± 68 | 9106 ± 271 | 13077 ± 381 |
| 98 | 139 ± 18 | 211 ± 12 | 452 ± 22 | 458 ± 29 | 1178 ± 237 | 220 ± 23 | 235 ± 18 | 383 ± 35 | 1706 ± 33 | 11530 ± 254 |
| 99 | 181 ± 85 | 282 ± 105 | 846 ± 165 | 2082 ± 185 | 3185 ± 63 | 467 ± 122 | 437 ± 85 | 1697 ± 283 | 9781 ± 13 | 11213 ± 294 |
| Medium | 86 ± 6 | | | | | 60 ± 12 | | | | |

[a]See Table 1 for sequences.

Taken together, the current results suggest that an accessible 5'-end of CpG DNA is required for its optimal immunostimulatory activity and smaller groups such as a phosphorothioate, a mononucleotide, or a dinucleotide do not effectively block the accessibility of the 5'-end of CpG DNA to receptors or factors involved in the immunostimulatory pathway. However, the conjugation of molecules as large as fluorescein or larger at the 5'-end of CpG DNA could abrogate immunostimulatory activity. These results have a direct impact on the studies of immunostimulatory activity of CpG DNA-antigen/vaccine/monoclonal antibody (mAb) conjugates. The conjugation of large molecules such as vaccines or mAbs at the 5'-end of a CpG DNA could lead to suboptimal immunostimulatory activity of CpG DNA. The conjugation of functional ligands at the 3'-end of CpG DNA not only contributes to increased nuclease stability but also increased immunostimulatory potency of CpG DNA in vivo.

Example 13

Effect of Linkers on Cytokine Secretion

The following oligonucleotides were synthesized for this study. Each of these modified oligonucleotides can be incorporated into an immunomer.

TABLE 17

| (CpG DNA Number) SEQ ID NO. | Sequence (5'→3')[a] |
|---|---|
| 102 | CCTACTAGCGTTCTCATC |
| 103 | CCTACTAGC2TTCTCATC |
| 104 | CCTACT2GCGTTCTCATC |
| 105 | CCTA2TAGCGTTCTCATC |
| 106 | CCT22TAGCGTTCTCATC |
| 107 | 22TACTAGCGTTCTCATC |
| 108 | CCTACTAGCGT2CTCATC |
| 109 | CCTACTAGCGTTC2CATC |
| 110 | CCTACTAGCGTTC22ATC |
| 111 | CCT6CTAGCGTTCTCATC |
| 112 | CCTACTAGCGTTC6CATC |
| 113 | CCT7CTAGCGTTCTCATC |
| 114 | CCTACTAGCGTTC7CATC |
| 4 | CTATCTGACGTTCTCTGT |
| 115 | CTAT1TGACGTTCTCTGT |
| 116 | CTA1CTGACGTTCTCTGT |
| 117 | CTATCTG2CGTTCTCTGT |
| 118 | CTATC2GACGTTCTCTGT |
| 119 | CTA2CTGACGTTCTCTGT |
| 120 | 22222TGACGTTCTCTGT |

TABLE 17-continued

| (CpG DNA Number) SEQ ID NO. | Sequence (5'→3')[a] |
|---|---|
| 121 | 2222TGACGTTCTCTGT |
| 122 | 222TGACGTTCTCTGT |
| 123 | 22TGACGTTCTCTGT |
| 124 | 2TGACGTTCTCTGT |
| 125 | CTAT3TGACGTTCTCTGT |
| 126 | CTA3CTGACGTTCTCTGT |
| 127 | CTA33TGACGTTCTCTGT |
| 128 | 33TGACGTTCTCTGT |
| 129 | CTAT4TGACGTTCTCTGT |
| 130 | CTA4CTGACGTTCTCTGT |
| 131 | CTA44TGACGTTCTCTGT |
| 132 | 44TGACGTTCTCTGT |
| 133 | CTAT5TGACGTTCTCTGT |
| 134 | CTA5CTGACGTTCTCTGT |
| 135 | CTA55TGACGTTCTCTGT |
| 136 | 55TGACGTTCTCTGT |
| 137 | CTA6CTGACGTTCTCTGT |
| 138 | CTATCTGACGTTC6CTGT |
| 139 | CTA7CTGACGTTCTCTGT |
| 140 | CTATCTGACGTTC7CTGT |
| 141 | CTATCTG8CGTTCTCTGT |
| 142 | CTATCT8ACGTTCTCTGT |
| 143 | CTATC8GACGTTCTCTGT |
| 144 | CTAT8TGACGTTCTCTGT |
| 145 | CTA8CTGACGTTCTCTGT |
| 146 | CTATCTGACG8TCTCTGT |
| 147 | CTATCTGACGT8CTCTGT |
| 148 | CTATCTGACGTT8TCTGT |
| 149 | CTATCTGACGTTC8CTGT |
| 150 | CTATCTG9CGTTCTCTGT |
| 151 | CTATCT9ACGTTCTCTGT |
| 152 | CTA9CTGACGTTCTCTGT |

TABLE 17-continued

Sequences of CpG DNA showing the position of substitution.

| (CpG DNA Number) SEQ ID NO. | Sequence (5'→3')[a] |
|---|---|
| 153 | CTATCTGACGT9CTCTGT |
| 154 | CTATCTGACGTTC9CTGT |

[a]See FIG. 14 for the chemical structures of substitutions 1-9. All CpG DNAs are phosphorothioate backbone modified.

Figure 15:
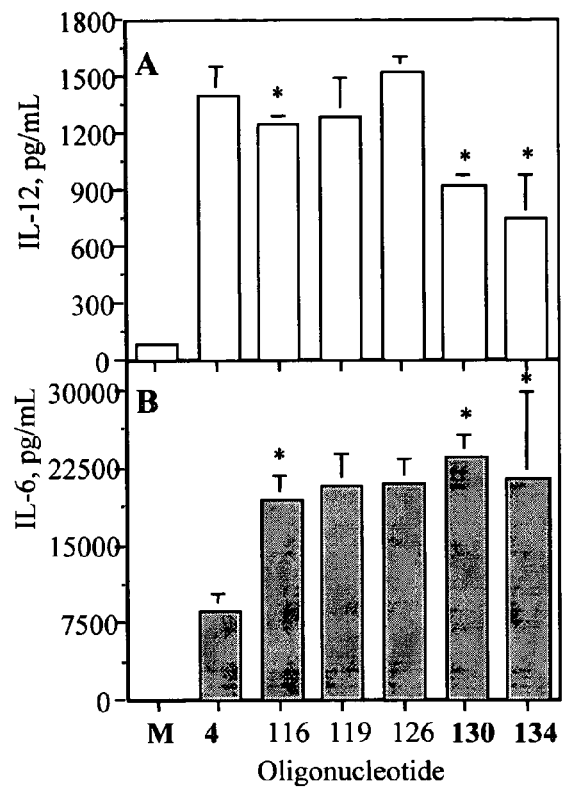
FIG. 15 shows cytokine profiles obtained using the modified oligonucleotides of Example 13. (SEQ ID NOS 4, 116, 119, 126, 130 and 134)

To evaluate the optimal linker size for potentiation of immunostimulatory activity, we measured IL-12 and IL-6 secretion induced by modified CpG DNAs in BALB/c mouse spleen cell cultures. All CpG DNAs induced concentration-dependent IL-12 and IL-6 secretion. FIG. 15 shows data obtained at 1 µg/mL concentration of selected CpG DNAs, 116, 119, 126, 130, and 134, which had a linker at the fifth nucleotide position in the 5'-flanking sequence to the CpG dinucleotide compared with the parent CpG DNA. The CpG DNAs, which contained C2- (1), C3- (2), and C4-linkers (3), induced secretion of IL-12 production similar to that of the parent CpG DNA 4. The CpG DNA that contained C6 and C9-linkers (4 and 5) at the fifth nucleotide position from CpG dinucleotide in the 5'-flanking sequence induced lower levels of IL-12 secretion than did the parent CpG DNA (FIG. 15), suggesting that substitution of linkers longer than a C4-linker results in the induction of lower levels of IL-12. All five CpG DNAs, which had linkers, induced two to three times higher IL-6 secretion than did the parent CpG DNA. The presence of a linker in these CpG DNAs showed a significant effect on the induction of IL-6 compared with CpG DNAs that did not have a linker. However, we did not observe length-dependent linker effect on IL-6-secretion.

To examine the effect on immunostimulatory activity of CpG DNA containing ethylenegylcol-linkers, we synthesized CpG DNAs 137 and 138, in which a triethyleneglycol-linker (6) is incorporated at the fifth nucleotide position in the 5'- and at the fourth nucleotide position in the 3'-flanking sequences to the CpG dinucleotide, respectively. Similarly, CpG DNAs 139 and 140 contained a hexaethyleneglycol-linker (7) in the 5'- or the 3'-flanking sequence to the CpG dinucleotide, respectively. All four modified CpG DNAs (137-140) were tested in BALB/c mouse spleen cell cultures for cytokine induction (IL-12, IL-6, and IL-10) in comparison with parent CpG DNA 4. All CpG DNAs induced concentration-dependent cytokine production over the concentration range tested (0.03-10.0 µg/mL) (data not shown). The levels of cytokines induced at 0.3 µg/mL concentration of CpG DNAs 137-140 are shown in Table 18. CpG DNAs 137 and 139, which had an ethyleneglycol-linker in the 5'-flanking sequence induced higher levels of IL-12 (2106±143 and 2066±153 pg/mL) and IL-6 (2362±166 and 2507±66 pg/mL) secretion than did parent CpG DNA 4 (Table 18). At the same concentration, 137 and 139 induced slightly lower levels of IL-10 secretion than did the parent CpG DNA (Table 18). CpG DNA 138, which had a shorter ethyleneglycol-linker (6) in the 3'-flanking sequence induced IL-12 secretion similar to that of the parent CpG DNA, but significantly lower levels of IL-6 and IL-10 (Table 18). CpG DNA 140, which had a longer ethyleneglycol-linker (7) induced significantly lower levels of all three cytokines tested compared with the parent CpG DNA (Table 18).

Though triethyleneglycol-linker (6) had a chain length similar to that of C9-linker (5), the CpG DNA containing triethyleneglycol-linker had better immunostimulatory activity than did CpG DNA containing C9-linker, as determined by induction of cytokine secretion in spleen cell cultures. These results suggest that the lower immunostimulatory activity observed with CpG DNA containing longer alkyl-linkers (4 and 5) may not be related to their increased length but to their hydrophobic characteristics. This observation prompted us to examine substitution of branched alkyl-linkers containing hydrophilic functional groups on immunostimulatory activity.

TABLE 18

Cytokine secretion induced by CpG DNAs containing an ethyleneglycol-linker in BALB/c mice spleen cell cultures.

| (CpG DNA Number) | Cytokine, pg/mL | | |
|---|---|---|---|
| SEQ ID NO | IL-12 | IL-6 | IL-10 |
| 4 | 1887 ± 233 | 2130 ± 221 | 86 ± 14 |
| 137 | 2106 ± 143 | 2362 ± 166 | 78 ± 21 |
| 138 | 1888 ± 259 | 1082 ± 25 | 47 ± 14 |
| 139 | 2066 ± 153 | 2507 ± 66 | 73 ± 17 |
| 140 | 1318 ± 162 | 476 ± 13 | 25 ± 5 |
| Medium | 84 ± 13 | 33 ± 6 | 2 ± 1 |

To test the effect on immunostimulatory activity of CpG DNA containing branched alkyl-linkers, two branched alkyl-linkers containing a hydroxyl (8) or an amine (9) functional group were incorporated in parent CpG DNA 4 and the effects on immunostimulatory activity of the resulting modified CpG DNAs (150-154-Table 19) were examined. The data obtained with CpG DNAs 150-154, containing amino-linker 9 at different nucleotide positions, in BALB/c mouse spleen cell cultures (proliferation) and in vivo (splenomegaly) are shown in Table 19.

TABLE 19

Spleen cell proliferation induced by CpG DNA containing an aminobutyryl propanediol-linker in BALB/c mice spleen cell cultures and splenomegaly in BALB/c mice.

| (CpG DNA Number[a]) SEQ ID NO. | Spleen cell proliferation (PI)[b] | Spleen weight (mg)[c] |
|---|---|---|
| 4 | 3.7 ± 0.8 | 121 ± 16 |
| 150 | 2.5 ± 0.6 | 107 ± 11 |
| 151 | 9.2 ± 0.7 | 169 ± 16 |
| 152 | 8.8 ± 0.4 | 220 ± 8 |
| 153 | 7.6 ± 0.7 | 127 ± 24 |
| 154 | 7.8 ± 0.04 | 177 ± 12 |
| M/V | 1.2 ± 0.3 | 102 ± 8 |
| LPS | 2.8 ± 0.5 | ND |

Parent CpG DNA 4 showed a proliferation index of 3.7±0.8 at a concentration of 0.1 µg/mL. At the same concentration, modified CpG DNAs 151-154 containing amino-linker 9 at different positions caused higher spleen cell proliferation than did the parent CpG DNA (Table 19). As observed with other linkers, when the substitution was placed adjacent to CpG dinucleotide (150), a lower proliferation index was noted compared with parent CpG DNA (Table 19), further confining that the placement of a linker substitution adjacent to CpG dinucleotide has a detrimental effect on immunostimulatory activity. In general, substitution of an amino-linker for 2'-deoxyribonucleoside in the 5'-flanking sequence (151 and 152) resulted in higher spleen cell proliferation than found with the substitution in the 3'-flanking sequence (153 and 154). Similar results were observed in the splenomegaly assay (Table 19), confirming the results observed in spleen cell cultures. Modified CpG DNAs containing glycerol-linker (8) showed immunostimulatory activity similar to or slightly higher that that observed with modified CpG DNA containing amino-linker (9) (data not shown).

Figure 4:
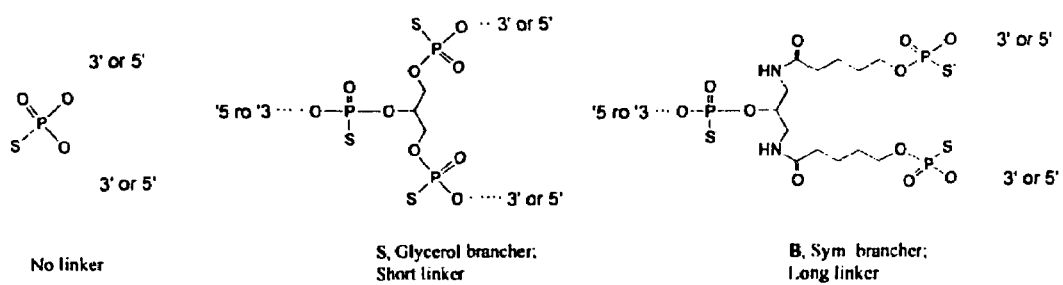
FIG. 4 depicts a group of representative small molecule linkers suitable for parallel synthesis of immunomers of the invention.
Figure 16:
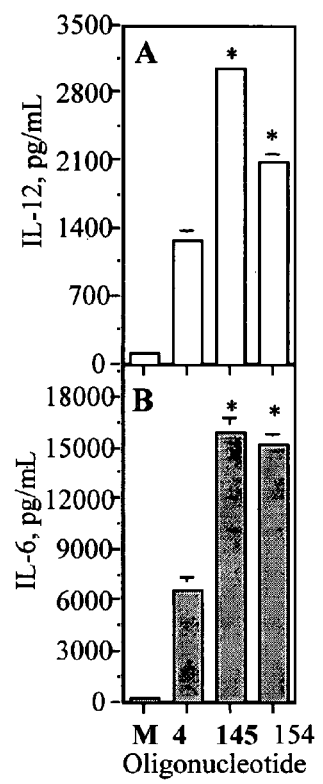
FIG. 16 shows relative cytokine induction for glycerol linkers compared with amino linkers. (SEQ ID NOS 4, 145 and 154)

In order to compare the immunostimulatory effects of CpG DNA containing linkers 8 and 9, we selected CpG DNAs 145 and 152, which had substitution in the 5'-flanking sequence and assayed their ability to induce cytokines IL-12 and IL-6 secretion in BALB/c mouse spleen cell cultures. Both CpG DNAs 145 and 152 induced concentration-dependent cytokine secretion. FIG. 4 shows the levels of IL-12 and IL-6 induced by 145 and 152 in mouse spleen cell cultures at 0.3 μg/mL concentration compared with parent CpG DNA 4. Both CpG DNAs induced higher levels of IL-12 and IL-6 than did parent CpG DNA 4. CpG DNA containing glycerol-linker (8) induced slightly higher levels of cytokines (especially IL-12) than did CpG DNA containing amino-linker (9) (FIG. 16). These results further confirm that the linkers containing hydrophilic groups are more favorable for immunostimulatory activity of CpG DNA.

We examined two different aspects of multiple linker substitutions in CpG DNA. In one set of experiments, we kept the length of nucleotide sequence to 13-mer and incorporated one to five C3-linker (2) substitutions at the 5'-end (120-124). These modified CpG DNAs permitted us to study the effect of an increase in the length of linkers without causing solubility problems. In the second set of experiments, we incorporated two of the same linker substitutions (3, 4, or 5) in adjacent positions in the 5'-flanking sequence to the CpG dinucleotide to study if there would be any additive effect on immunostimulatory activity.

Modified CpG DNAs were studied for their ability to induce cytokine production in BALB/c mouse spleen cell cultures in comparison with parent CpG DNA 4. All CpG DNAs induced concentration-dependent cytokine production. The data obtained at 1.0 μg/mL concentration of CpG DNAs is shown in Table 20. In this assay, parent CpG DNA 4 induced 967±28 pg/mL of IL-12, 1593±94 pg/mL of IL-6, and 14±6 pg/mL of IL-10 secretion at 1 μg/mL of concentration. The data presented in Table 20 suggest that as the number of linker substitutions decreased IL-12 induction decreased. However, the induction of lower levels of IL-12 secretion by CpG DNAs 123 and 124 could be the result of the shorter length of CpG DNAs. Our studies with unmodified CpG DNA shorter than 15-nucleotides showed insignificant immunostimulatory activity (data not shown). Neither length nor the number of linker substitutions have a lesser effect on IL-6 secretion. Though IL-10 secretion increased with linker substitutions, the overall IL-10 secretion by these CpG DNAs was minimal.

Figure 17:
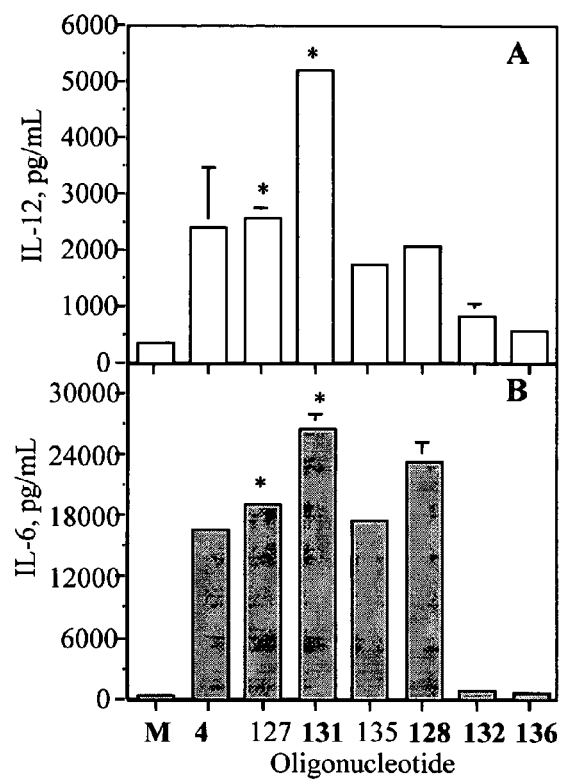
FIG. 17 shows relative cytokine induction for various linkers and linker combinations. (SEQ ID NOS 4, 127, 131, 135, 128, 132 and 136)

CpG DNAs containing two linker substitutions (linker 3-127; linker-4-131; linker-5-135) at the fourth and fifth positions in the 5'-flanking sequences to the CpG dinucleotide and the corresponding 5'-truncated versions 128, 132, and 136, respectively, were tested for their ability to induce cytokine secretion in BALB/c mouse spleen cell cultures. The levels of IL-12 and IL-6 secreted at 1.0 μg/mL concentration are shown in FIG. 17. The results presented in FIG. 17 suggest that the immunostimulatory activity is dependent on the nature of the linker incorporated. The substitution of the fourth and fifth nucleosides with C4-linker 3 (CpG DNA 127) had an insignificant effect on cytokine secretion compared with parent CpG DNA 4, suggesting that the nucleobase and sugar ring at these positions are not required for receptor recognition and/or binding. The deletion of the nucleotides beyond the linker substitutions (CpG DNA 128) caused higher IL-12 and IL-6 secretion than that found with CpG DNAs 4 and 127. As expected, the substitution of two C6-linkers (4) resulted in IL-12 secretion lower than and IL-6 secretion similar to that induced by parent CpG DNA 4. The 5'-truncated CpG DNA 132 induced higher cytokine secretion than did CpG DNA 131. The CpG DNAs 135 and 136, which had two C9-linkers (5), induced insignificant cytokine secretion, confirming the results obtained with mono-substituted CpG DNA containing the same linker as described above.

Example 14

Effect of Phosphodiester Linkages on Cytokine Induction

To test the effect of phosphodiester linkages on immunomer-induced cytokine induction, the following molecules were synthesized.

TABLE 21

PO-Immunomer sequences and analytical data

| CpG DNA SEQ ID NO | Sequence[a] | Backbone[b] | Molecular Weight | | |
|---|---|---|---|---|---|
| | | | Calculated | Found[c] | |
| 4 | 5'-CTATCTGACGTTCTCTGT-3' | PS PO | 5702 5432 | 5704 5428 | 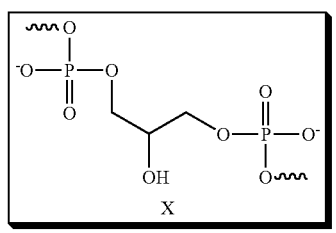 |
| 155 | 5'-CTATCTGACGTTCTCTGT-3' | | | | |

TABLE 21-continued

PO-Immunomer sequences and analytical data

| CpG DNA SEQ ID NO | Sequence[a] | Backbone[b] | Molecular Weight Calculated | Found[c] | |
|---|---|---|---|---|---|
| 156 | 5'-CTGACGTTCTCTGT-X-TGTCTCTTGCAGTC-5' | PO | 8656 | 8649 | 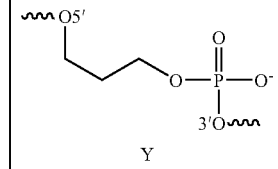 |
| 157 | 5'-YYCTGACGTTCTCTGT-X-TGTCTCTTGCAGTCYY-5' | PO | 9208 | 9214 | |

[a] Arrows indicate 5'-3' directionality of CpG dinucleotide in each DNA molecule and structures of X and Y are shown in boxes.
[b] PS and PO stand for phosphorothioate and phosphodiester backbones, respectively.
[c] As determined by MALDI-TOF mass spectrometry.

PS-CpG DNA 4 (Table 21) was found to induce an immune response in mice (data not shown) with PO-CpG DNA 155 serving as a control. PO-immunomers 156 and 157 each contain two identical, truncated copies of the parent CpG DNA 155 joined through their 3'-ends via a glyceryl linker, X (Table 21). While 156 and 157 each contain the same oligonucleotide segments of 14 bases, the 5'-ends of 157 were modified by the addition of two C3-linkers, Y (Table 21). All oligonucleotides 4, 155-157 contain a 'GACGTT' hexameric motif known to activate the mouse immune system.

Figure 18:
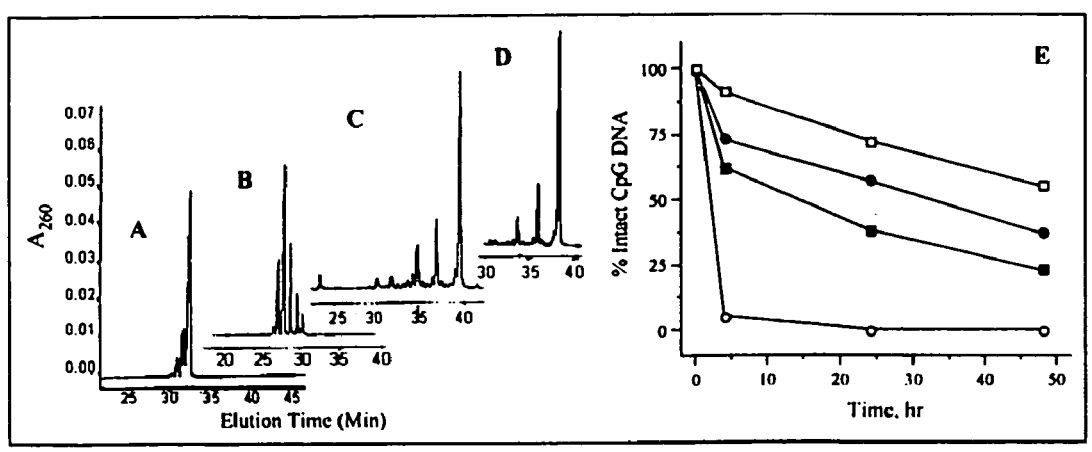
FIGS. 18 A-E shows relative nuclease resistance for various PS and PO immunomers and oligonucleotides.

The stability of PO-immunomers against nucleases was assessed by incubating CpG DNAs 4, 155-157 in cell culture medium containing 10% fetal bovine serum (FBS) (non-heat-inactivated) at 37° C. for 4, 24, and 48 hr. Intact CpG DNA remaining in the reaction mixtures were then determined by CGE. FIGS. 18A-D shows the nuclease digestion profiles of CpG DNAs 4, 155-157 incubated in 10% FBS for 24 hr. The amount of full-length CpG DNA remaining at each time point is shown in FIG. 18E. As expected, the parent PS-CpG DNA 4 is the most resistant to serum nucleases. About 55% of 18-mer 4 remained undegraded after 48 hr incubation. In contrast, only about 5% of full-length PO-immunomer 155 remained after 4 hr under the same experimental conditions confirming that DNA containing phosphodiester linkages undergoes rapid degradation. As expected, both PO-immunomers 156 and 157 were more resistant than 155 to serum nucleases. After 4 hr, about 62% and 73% of 156 and 157 respectively were intact compared with about 5% of 155 (FIG. 18 E). Even after 48 hr, about 23% and 37% of 156 and 157, respectively, remained undegraded. As well as showing that 3'-3'-linked PO-immunomers are more stable against serum nucleases, these studies indicate that chemical modifications at the 5'-end can further increase nuclease stability.

Figure 19:
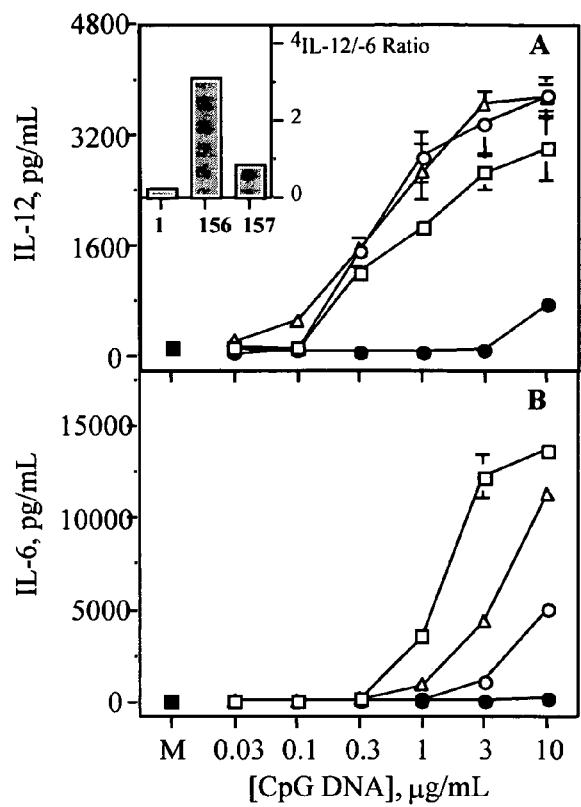
FIG. 19 shows relative cytokine induction for PO immunomers compared with PS immunomers in BALB/c mouse spleen cell cultures. (SEQ ID NOS 1, 156 and 157)

The immunostimulatory activity of CpG DNAs was studied in BALB/c and C3H/HeJ mice spleen cell cultures by measuring levels of cytokines IL-12 and IL-6 secreted. All CpG DNAs induced a concentration-dependent cytokine secretion in BALB/c mouse spleen cell cultures (FIG. 19). At 3 μg/mL, PS-CpG DNA 4 induced 2656±256 and 12234±1180 pg/mL of IL-12 and IL-6 respectively. The parent PO-CpG DNA 155 did not raise cytokine levels above background except at a concentration of 10 μg/mL. This observation is consistent with the nuclease stability assay results. In contrast, PO-immunomers 156 and 157 induced both IL-12 and IL-6 secretion in BALB/c mouse spleen cell cultures.

The results presented in FIG. 19 show a clear distinction in cytokine induction profiles of PS- and PO-CpG DNAs. PO-immunomers 156 and 157 induced higher levels of IL-12 than did PS-CpG DNA 4 in BALB/c mouse spleen cell cultures (FIG. 19A). In contrast, at concentrations up to 3 μg/mL, they produced negligible amounts of IL-6 (FIG. 19B). Even at the highest concentration (10 μg/mL), PO-immunomer 156 induced significantly less IL-6 than did PS-CpG DNA 4. The presence of C3 linkers at the 5'-terminus of PO-immunomer 157 resulted in slightly higher levels of IL-6 secretion compared with 156. However, importantly, the levels of IL-6 produced by PO-immunomer 157 are much lower than those induced by PS CpG DNA 4. The inset of FIG. 19A shows the ratio of IL-12 to IL-6 secreted at 3 μg/mL concentration. In addition to increasing IL-12 secretion, PO-immunomers 156 and 157 induced higher levels of IFN-γ than did PS-CpG DNA 4 in BALB/c mouse spleen cell cultures (data not shown).

The different cytokine profiles induced by PO- and PS-CpG DNAs in BALB/c mouse spleen cell cultures prompted us to study the pattern of cytokine induction of CpG DNAs in C3H/HeJ mouse spleen cell cultures (an LPS lower-responsive strain). All three CpG DNAs tested in this assay induced concentration-dependent cytokine secretion (FIGS. 20A and B). Since PO-CpG DNA 155 failed to induce cytokine secretion in BALB/c mouse spleen cell cultures, it was not further tested in C3H/HeJ spleen cell cultures. Both PO-immunomers 156 and 157 induced higher IL-12 production than did PS-CpG DNA 4 (FIG. 21A). However, at concentrations up to 3 μg/mL, neither induced IL-6 production. At the highest concentration tested (10 μg/mL), both induced significantly less IL-6 than did PS-CpG DNA 4 (FIG. 21B). The ratio of IL-12 to IL-6 secreted is calculated to distinguish cytokine secretion profiles of PS and PO CpG DNAs (FIG. 21A inset). In addition, the C3H/HeJ spleen cell culture results suggest that the responses observed with CpG DNAs are not due to LPS contamination.

PS-CpG DNAs have been shown to induce potent antitumor activity in vivo. Since PO-CpG DNAs exhibited greater nuclease stability and induced higher levels of IL-12 and IFN-γ secretion in in vitro assays, we were interested to see if these desirable properties of PO-immunomers improve the antitumor activity in vivo. We administered PO-immunomer 157 subcutaneously at a dose of 0.5 mg/kg every other day to nude mice bearing tumor xenografts of MCF-7 breast cancer cells that express wild-type p53, or DU-145 prostate cancer cells that express mutated p53. PO-immunomer 157 gave 57% growth inhibition of MCF-7 tumors on day 15 compared with the saline control (FIG. 22A). It also produced 52% growth inhibition of DU-145 tumors on day 34 (FIG. 22B).

These antitumor studies suggest that PO-immunomers of the proposed design exhibit potent antitumor activity in vivo.

Example 15

Short Immunomers

To test the effects of short immunomers on cytokine induction, the following immunomers were used. These results show that immunomers as short as 5 nucleotides per segment are effective in inducing cytokine production.

TABLE 22

Immunomer Structure and Immunostimulatory Activity in BABL/C Mouse Spleen Cell Cultures

| (Oligo No.) SEQ ID NO. | Sequences and Modification (5'-3') | Oligo Length/ or Each Chain | IL-12 (pg/mL) 10 μg/mL | IL-6 (pg/mL) 10 μg/mL |
|---|---|---|---|---|
| 4 | 5'-CTATCTGACGTTCTCTGT-3' | 18mer | 2731 | 4547 |
| 25 | 5'-CTATCTGTCGTTCTCTGT-3' | 18mer | 795 | 789 |
| 158 | 5'-TCTGACGTTCT-3'⟍<br>　　　　　　　　　$X_1$<br>5'-TCTGACGTTCT-3'⟋ | 11mer | 3490 | 5319 |
| 159 | 5'-TCTGTCGTTCT-3'⟍<br>　　　　　　　　　$X_1$<br>5'-TCTGTCGTTCT-3'⟋ | 11mer | 3265 | 4625 |
| 160 | 5'-TCGTTG-3'⟍<br>　　　　　　$X_1$<br>5'-TCGTTG-3'⟋ | 6mer | 2085 | 2961 |
| 161 | 5'-TCGTTG-3'XX⟍<br>　　　　　　　　$X_1$<br>5'-TCGTTG-3'XX⟋ | 6mer | 3169 | 5194 |
| 162 | 5'-TCGTTG-3'X⟍<br>　　　　　　　$X_1$<br>5'-TCGTTG-3'X⟋ | 6mer | 1015 | 705 |
| 163 | 5'-TCGTT-3'X⟍<br>　　　　　　$X_1$<br>5'-TCGTT-3'X⟋ | 5mer | 2623 | 3619 |
| 164 | 5'-ACGTTG-3'X⟍<br>　　　　　　　$X_1$<br>5'-ACGTTG-3'X⟋ | 6mer | 564 | 845 |
| 165 | 5'-GCGTTG-3'X⟍<br>　　　　　　　$X_1$<br>5'-GCGTTG-3'X⟋ | 6mer | 196 | 0 |
| 166 | 5'-CCGTTG-3'X⟍<br>　　　　　　　$X_1$<br>5'-CCGTTG-3'X⟋ | 6mer | 219 | 0 |
| 167 | 5'-GTCGTT-3'X⟍<br>　　　　　　　$X_1$<br>5'-GTCGTT-3'X⟋ | 6mer | 1441 | 5056 |
| 168 | 5'-TGTCGT-3'X⟍<br>　　　　　　　$X_1$<br>5'-TGTCGT-3'X⟋ | 6mer | 198 | 0 |
| 169 | 5'-TCGTTG-3'X⟍<br>　　　　　　　$X_1$-X3'-GTTGCT-5'<br>5'-TCGTTG-3'X⟋ | 6mer | 2410 | 4857 |

Normal phase represents a phosphorothioate linkage.

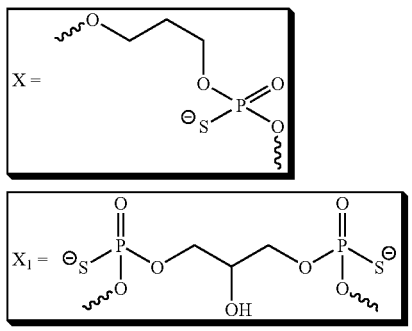

Example 16

Figure 20:
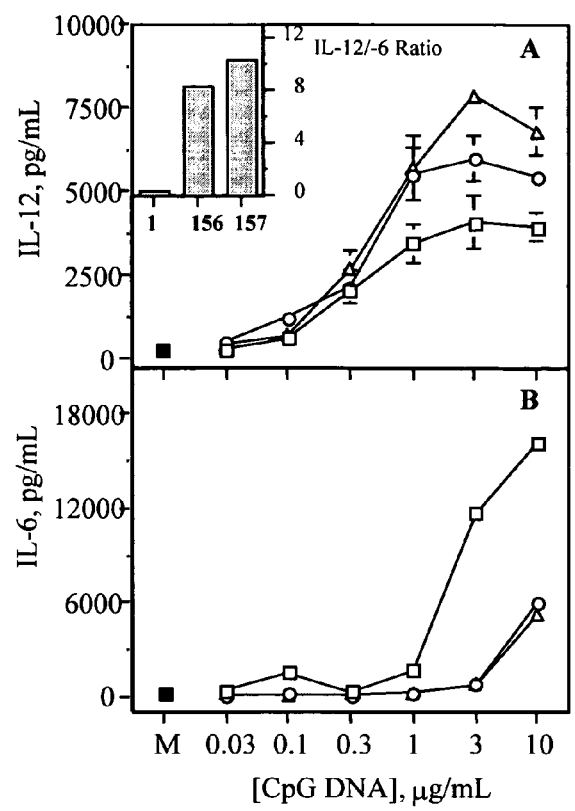
FIG. 20 shows relative cytokine induction for PO immunomers compared with PS immunomers in C3H/Hej mouse spleen cell cultures. (SEQ ID NOS 1, 156 and 157)
Figure 21:
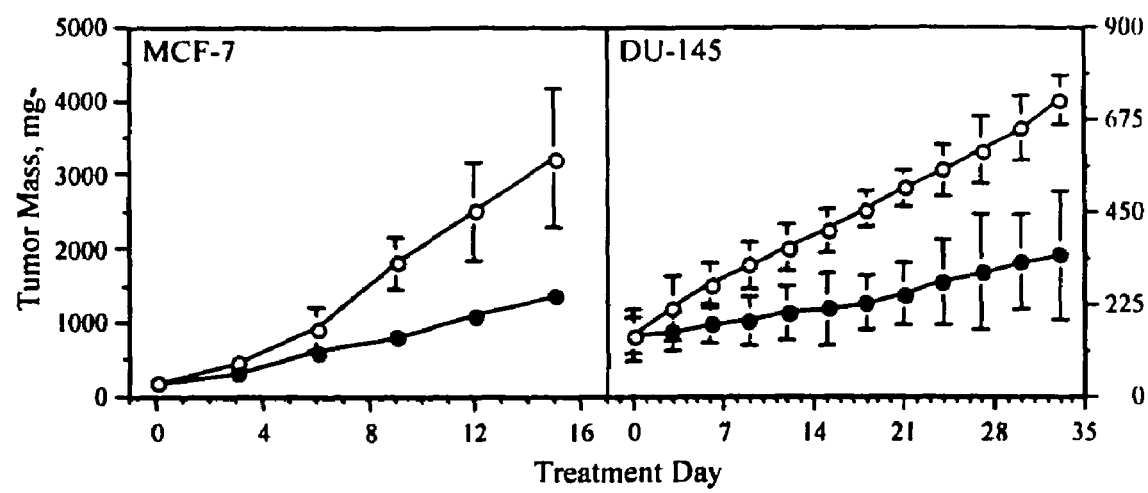
FIG. 21 shows relative cytokine induction for PO immunomers compared with PS immunomers in C3H/Hej mouse spleen cell cultures at high concentrations of immunomers.
Figure 22:
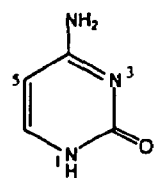
FIG. 22 shows some pyrimidine and purine structures.
Figure 22:
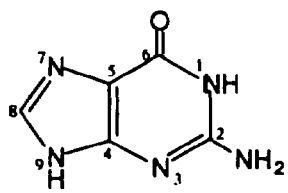
Figure 22:
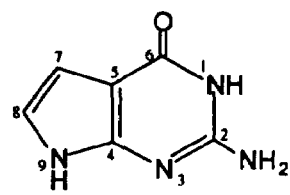
Figure 22:
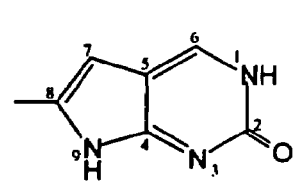
Figure 23:
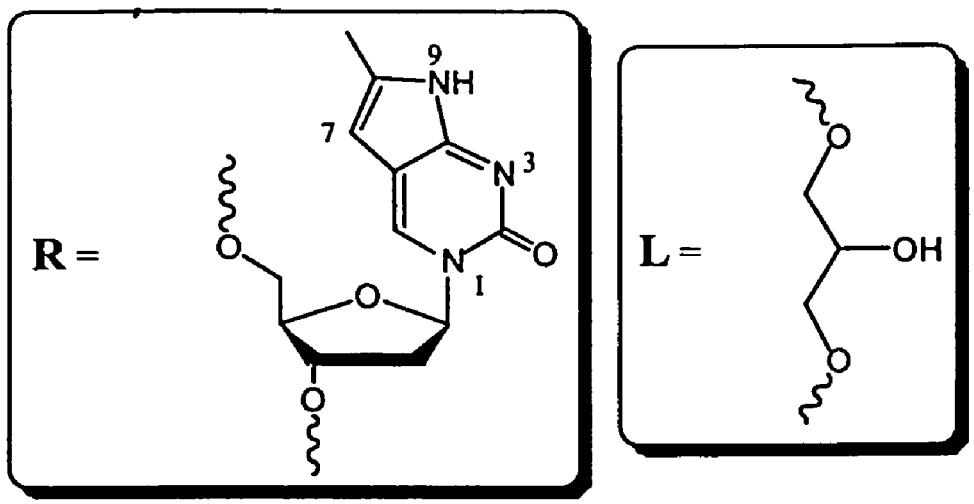
FIG. 23 shows some immunostimulatory oligonucleotides or immunomers used in the present study (SEQ ID NOS 4, 189, 10, 25 and 190-192, respectively in order of appearance).
Figure 24:
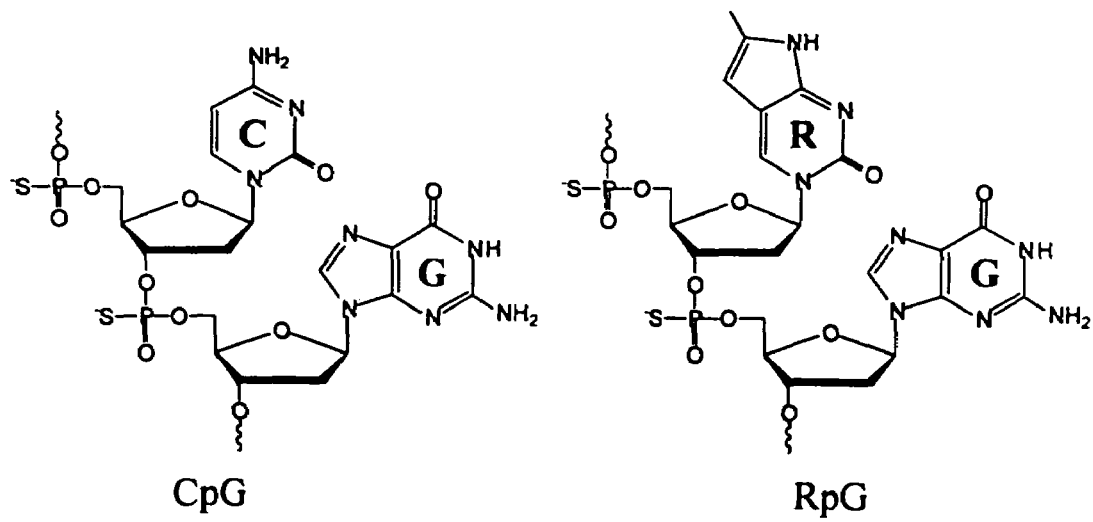
FIG. 24 shows a comparison of a natural CpG motif and an immonostimulatory motif having a synthetic purine-pG dinucleotide.
Figure 25:
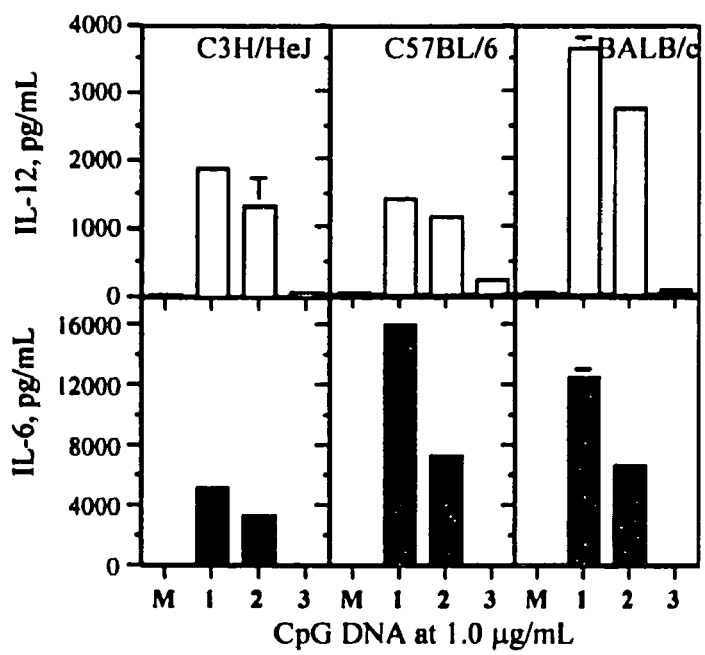
FIG. 25 shows the IL-12 and IL-6 profiles of various immunostimulatory oligonucleotides used in the present study. (SEQ ID NOS 1, 2 and 3)
Figure 26:
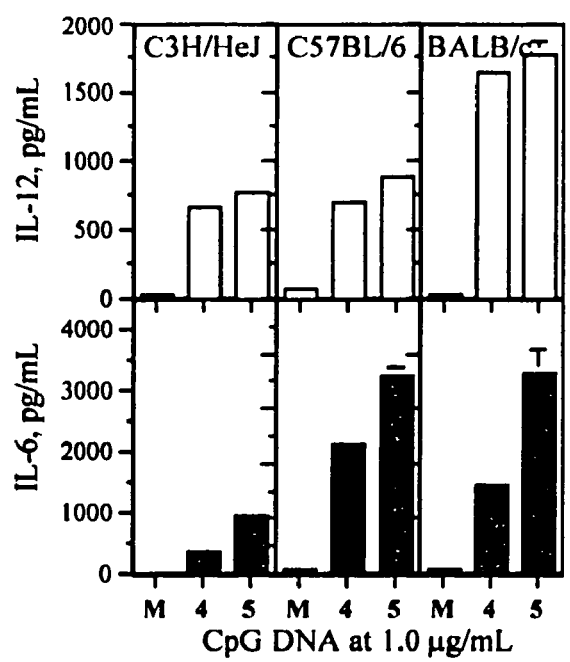
FIG. 26 shows the IL-12 and IL-6 profiles of additional immunostimulatory oligonucleotides used in the present study. (SEQ ID NOS 4 and 5)
Figure 27:
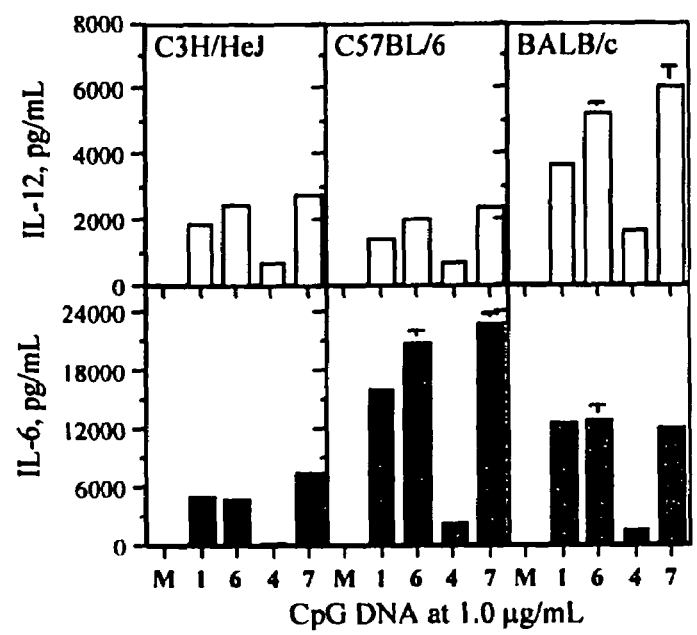
FIG. 27 shows the IL-12 and IL-6 profiles of immunostimulatory oligonucleotides and immunomers used in the present study. (SEQ ID NOS 1, 6, 4 and 7)
Figure 28:
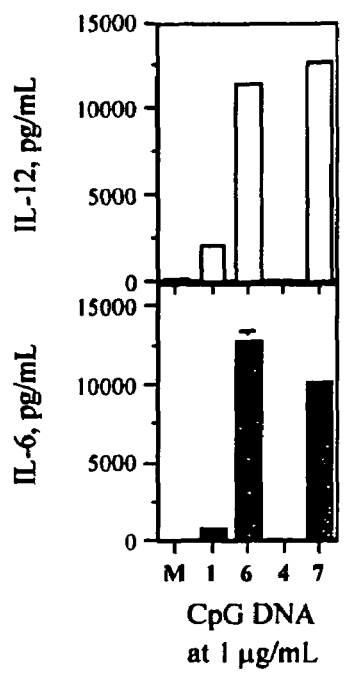
FIG. 28 compares IL-12 and IL-6 profiles provided by mouse and human motifs in immunostimulatory oligonucleotides and immunomers. (SEQ ID NOS 1, 6, 4 and 7)
Figure 29:
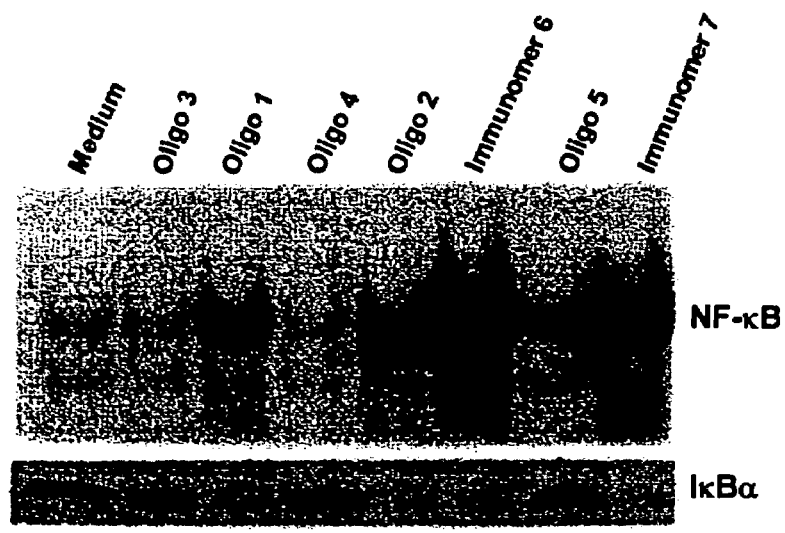
FIG. 29 shows activation of NF-κB and degradation of Iκ-Bα in J774 cells treated with various immunostimulatory oligonucleotides and immunomers. (SEQ ID NOS 3, 1, 4, 2, 6, 5 and 7)
Figure 30:
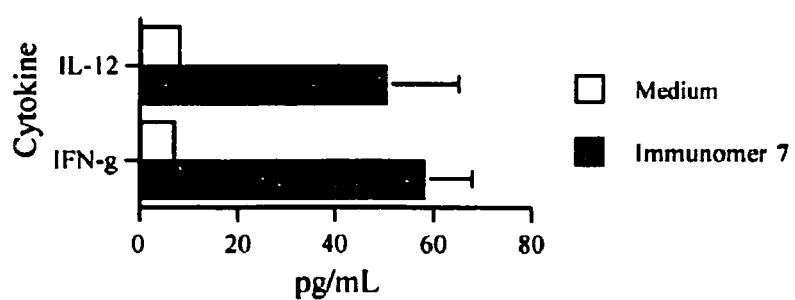
FIG. 30 shows immunostimulatory activity of an immunomer in human PBMC culture. (SEQ ID NO 7)

Effect of Incorporation of 2-oxo-7-deaza-8-methyl-purine into Mouse-Specific and Human-Specific Immunostimulatory Motifs Mouse spleenocyte cultures were prepared and treated as described in Example 4. Cultures were treated with medium or with oligonucleotides 170, 171, or 172. (See FIG. 15). All oligonucleotides contained mouse-specific immunostimulatory motifs (GACGTT), but oligonucleotide 171 contained an RpG substitution and oligonucleotide 172 contained a CpR substitution, wherein R is 2-oxo-7-deaza-8-methyl-purine. The results are shown in FIG. 17. The RpG substitution was recognized by the mouse spleen cultures resulting in cytokine production, whereas the CpR substitution was not. Treatment of the cultures with oligonucleotides 173 or 174, containing a human-specific immunostimulatory motif GTCGTT or with an RpG substitution, respectively, showed better recognition by the mouse spleenocytes with the RpG substitution than with the native human sequence (FIG. 18). Treatment with parent oligonucleotides 170 (mouse-specific) or 173 (human-specific), compared with their respective immunomers 175 or 176 (each containing the RpG substitution) showed better results for the immunomers, suggesting that incorporation of the RpG substitution into the immunomers may overcome species-dependent selectivity (FIG. 19). Treatment of human macrophage-like cell cultures with oligonucleotides 170 or 173, compared with immunomers 175 or 176 further suggests that incorporation of the RpG substitution into immunomers overcomes species-selective activity (FIG. 20). Similar results are shown for activation of NF-κB and degradation of Iκ-Bα in J774 cells (FIG. 21). Immunomer 176 also showed immunostimulatory activity in cultures of human peripheral blood mononuclear cells (FIG. 22).

Example 17

Isolation of Human B Cells and Plasmacytoid Dendritic Cells (pDCs)

PBMCs from freshly drawn healthy volunteer blood (CBR Laboratories, Boston, Mass.) were isolated by Ficoll density gradient centrifugation method (Histopaque-1077, Sigma) and B cells were isolated from PBMCs by positive selection using the CD19 cell isolation kit (Miltenyi Biotec) according to the manufacturer's instructions.

Example 18

B Cell Assay

B-Cells were plated in 96-well plates using $1\times10^6$ cells/mL, 200 µL/well). The Immunomers were added to a final concentration of 0.3, 1.0, 3.0, or 10.0 µg/mL to the cell cultures and incubated at 37° C. for 24 hr. Supernatants were then harvested and assayed for IL-6 and IL-10 using ELISA kit (provided by PBL). Tables 23A-23D show an average ±SD for Donors 1-4 with Immunomers at a final concentration of 10.0 µg/mL.

TABLE 23A

Immunomer Structure and Immunostimulatory Activity in Human B-Cell Assay for Donor 1 (48 hs).

| (Oligo No.) SEQ ID NO. | Sequences and Modification (5'-3') | IL-6 (pg/ml) 10 µg/ml DN1 | IL-10 (pg/ml) 10 µg/ml DN1 |
|---|---|---|---|
| 26 | 5'-TCTGTCG$_1$TTCT-X-TCTTG$_1$CTGTCT-5' | 2718 ± 35.5 | 132.7 ± 5.5 |
| 173 | 5'-TCTGTCG$_2$TTCT-X-TCTTG$_2$CTGTCT-5' | 2737 ± 19 | 144 ± 3.1 |
| 170 | 5'-TCTGTC$_1$GTTCT-X-TCTTGC$_1$TGTCT-5' | 2210 ± 8.5 | 122.5 ± 5.1 |
| 175 | 5'-TCTGTC$_3$GTTCT-X-TCTTGC$_3$TGTCT-5' | 2175 ± 28.7 | 60.2 ± 1.2 |
| 171 | 5'-CTGTCG$_2$TTCTC-X-CTCTTG$_2$CTGTC-5' | 2714 ± 2.7 | 132.1 ± 1 |
| 178 | 5'-CTGTC$_2$GTTCTC-X-CTCTTGC$_2$TGTC-5' | 2166 ± 29.6 | 30.9 ± 0.2 |
| 172 | 5'-TCG$_1$TCG$_1$TTCTG-X-GTCTTG$_1$CTG$_1$CT-5' | 2956 ± 75 | 158.8 ± 7.8 |
| 180 | 5'-TCG$_2$TCG$_2$TTCTG-X-GTCTTG$_2$CTG$_2$CT-5' | 3057 ± 37.2 | 132.7 ± 2.7 |
| 181 | 5'-TC$_1$GTC$_1$GTTCTG-X-GTCTTGC$_1$TGC$_1$T-5' | 2171 ± 18.6 | 50.9 ± 1.6 |
| 182 | 5'-TC$_2$GTC$_2$GTTCTG-X-GTCTTGC$_2$TGC$_2$T-5' | 3067 ± 21 | 53.6 ± 0.2 |

TABLE 23A-continued

Immunomer Structure and Immunostimulatory Activity in Human B-Cell Assay for Donor 1 (48 hs).

| (Oligo No.) SEQ ID NO. | Sequences and Modification (5'-3') | IL-6 (pg/ml) 10 µg/ml DN1 | IL-10 (pg/ml) 10 µg/ml DN1 |
|---|---|---|---|
| 183 | 5'-TC$_3$GTC$_3$GTTCTG-X-GTCTTGC$_3$TGC$_3$T-5' | 1760 ± 2.4 | 37.7 ± 1.3 |
| 185 | 5'-TG$_1$CTG$_1$CTTG-X-GTTCG$_1$TCG$_1$T-5' | 2138 ± 41.3 | 25.7 ± 0.2 |
| media | | 1674 ± 22 | 2.8 ± 0.1 |

TABLE 23B

Immunomer Structure and Immunostimulatory Activity in Human B-Cell Assay for Donor 2 (48 hs).

| (Oligo No.) SEQ ID NO. | Sequences and Modification (5'-3') | IL-6 (pg/ml) 10 µg/ml DN2 | IL-10 (pg/ml) 10 µg/ml DN2 |
|---|---|---|---|
| 26 | 5'-TCTGTCG$_1$TTCT-X-TCTTG$_1$CTGTCT-5' | 521 ± 2.6 | 0 ± 0 |
| 170 | 5'-TCTGTC$_1$GTTCT-X-TCTTGC$_1$TGTCT-5' | 1157 ± 0.9 | 30.9 ± 0 |
| 172 | 5'-TCG$_1$TCG$_1$TTCTG-X-GTCTTG$_1$CTG$_1$CT-5' | 2198 ± 2.6 | 158 ± 9.7 |
| 180 | 5'-TCG$_2$TCG$_2$TTCTG-X-GTCTTG$_2$CTG$_2$CT-5' | 2464 ± 34.5 | 289 ± 23.6 |
| 181 | 5'-TC$_1$GTC$_1$GTTCTG-X-GTCTTGC$_1$TGC$_1$T-5' | 686 ± 1.7 | 18.6 ± 1 |
| 182 | 5'-TC$_2$GTC$_2$GTTCTG-X-GTCTTGC$_2$TGC$_2$T-5' | 867 ± 17 | 31.3 ± 1.5 |
| 183 | 5'-TC$_3$GTC$_3$GTTCTG-X-GTCTTGC$_3$TGC$_3$T-5' | 355 ± 6.1 | 0 ± 0 |
| 185 | 5'-TG$_1$CTG$_1$CTTG-X-GTTCG$_1$TCG$_1$T-5' | 132 ± 0 | 0 ± 0 |
| media | | 65.6 ± 2.8 | 0 ± 0 |

TABLE 23C

Immunomer Structure and Immunostimulatory Activity in Human B-Cell Assay for Donor 3 (48 hs).

| (Oligo No.) SEQ ID NO. | Sequences and Modification (5'-3') | IL-6 (pg/ml) 10 µg/ml DN3 | IL-10 (pg/ml) 10 µg/ml DN3 |
|---|---|---|---|
| 26 | 5'-TCTGTCG$_1$TTCT-X-TCTTG$_1$CTGTCT-5' | 495 ± 2.9 | 14.8 ± 0.3 |
| 170 | 5'-TCTGTC$_1$GTTCT-X-TCTTGC$_1$TGTCT-5' | 1043 ± 0 | 28.4 ± 1.4 |
| 172 | 5'-TCG$_1$TCG$_1$TTCTG-X-GTCTTG$_1$CTG$_1$CT-5' | 1521 ± 24.9 | 27.2 ± 1.4 |
| 180 | 5'-TCG$_2$TCG$_2$TTCTG-X-GTCTTG$_2$CTG$_2$CT-5' | 1018 ± 13.4 | 33.5 ± 0.7 |
| 181 | 5'-TC$_1$GTC$_1$GTTCTG-X-GTCTTGC$_1$TGC$_1$T-5' | 423 ± 3.9 | 9.5 ± 0.2 |
| 182 | 5'-TC$_2$GTC$_2$GTTCTG-X-GTCTTGC$_2$TGC$_2$T-5' | 524 ± 36.2 | 9.0 ± 0.1 |
| 183 | 5'-TC$_3$GTC$_3$GTTCTG-X-GTCTTGC$_3$TGC$_3$T-5' | 184 ± 3.3 | 5.8 ± 0.3 |
| 185 | 5'-TG$_1$CTG$_1$CTTG-X-GTTCG$_1$TCG$_1$T-5' | 139.4 ± 0 | 7.1 ± 0.3 |
| media | | 40.9 ± 2.6 | 6.1 ± 2.4 |

TABLE 23D

Immunomer Structure and Immunostimulatory Activity in Human B-Cell Assay for Donor 4 (48 hs).

| (Oligo No.) SEQ ID NO. | Sequences and Modification (5'-3') | IL-6 (pg/ml) 10 µg/ml DN4 | IL-10 (pg/ml) 10 µg/ml DN4 |
|---|---|---|---|
| 26 | 5'-TCTGTCG$_1$TTCT-X-TCTTG$_1$CTGTCT-5' | 1027 ± 0 | 360 ± 59.8 |
| 173 | 5'-TCTGTCG$_2$TTCT-X-TCTTG$_2$CTGTCT-5' | 1470 ± 46.9 | 559 ± 0 |
| 170 | 5'-TCTGTC$_1$GTTCT-X-TCTTGC$_1$TGTCT-5' | 1272 ± 23 | 470 ± 1.1 |
| 175 | 5'-TCTGTC$_3$GTTCT-X-TCTTGC$_3$TGTCT-5' | 848 ± 6.8 | 133 ± 4.5 |
| 171 | 5'-CTGTCG2TTCTC-X-CTCTTG2CTGTC-5' | 1424 ± 22 | 634 ± 2.7 |
| 178 | 5'-CTGTC$_2$GTTCTC-X-CTCTTGC$_2$TGTC-5' | 407 ± 3.1 | 61.8 ± 0.1 |
| 172 | 5'-TCG$_1$TCG$_1$TTCTG-X-GTCTTG$_1$CTG$_1$CT-5' | 2837 ± 72.2 | 738 ± 5.5 |
| 180 | 5'-TCG$_2$TCG$_2$TTCTG-X-GTCTTG$_2$CTG$_2$CT-5' | 1986 ± 34.8 | 765 ± 7.9 |
| 181 | 5'-TC$_1$GTC$_1$GTTCTG-X-GTCTTGC$_1$TGC$_1$T-5' | 1126 ± 23.1 | 165 ± 1.6 |
| 182 | 5'-TC$_2$GTC$_2$GTTCTG-X-GTCTTGC$_2$TGC$_2$T-5' | 1372 ± 14.3 | 150 ± 0.9 |
| 183 | 5'-TC$_3$GTC$_3$GTTCTG-X-GTCTTGC$_3$TGC$_3$T-5' | 618 ± 4.9 | 73 ± 3.1 |
| 185 | 5'-TG$_1$CTG$_1$CTTG-X-GTTCG$_1$TCG$_1$T-5' | 891 ± 13.6 | 37.8 ± 0.5 |
| media | | 88.6 ± 0 | 3.8 ± 0.4 |

Example 19

Human pDC Cultures pDCs were isolated from human PBMCs using a BDCA-4 cell isolation kit (Miltenyi Biotec) according to the manufacturer's instructions. pDC were plated in 96-well plates using 1×10$^6$ cells/mL, 200 µL/well). The Immunomers were added to a final concentration of 0.3, 1.0, 3.0, or 10.0 µg/mL to the cell cultures and incubated at 37° C. for 24 hr. Supernatants were then harvested and assayed for IFN-α, IL-6 and TNF-α using ELISA kit (provided by PBL). Tables 24A-24D show an average±SD of IFN-α, IL-6 and TNF-α for Donors 1-4 with Immunomers at a concentrations of 10.0 µg/mL.

TABLE 24A

Immunomer Structure and Immunostimulatory Activity in Human Dendritic Cell Assay for Donor 1 (24 hs)

| (Oligo No.) SEQ ID NO. | Sequences and Modification (5'-3') | IFN-α (pg/ml) 10 µg/ml DN1 | IL-6 (pg/ml) 10 µg/ml DN1 | TNF-α (pg/ml) 10 µg/ml DN1 |
|---|---|---|---|---|
| 26 | 5'-TCTGTCG$_1$TTCT-X-TCTTG$_1$CTGTCT-5' | 2524 ± 99 | 6089 ± 127 | 2643 ± 22 |
| 173 | 5'-TCTGTCG$_2$TTCT-X-TCTTG$_2$CTGTCT-5' | 21219 ± 1253 | 4581 ± 54 | 7939 ± 0 |
| 170 | 5'-TCTGTC$_1$GTTCT-X-TCTTGC$_1$TGTCT-5' | 6692 ± 195 | 4787 ± 105 | 6021 ± 0 |
| 175 | 5'-TCTGTC$_3$GTTCT-X-TCTTGC$_3$TGTCT-5' | 4503 ± 515 | 2379 ± 188 | 3842 ± 0 |
| 171 | 5'-CTGTCG$_2$TTCTC-X-CTCTTG$_2$CTGTC-5' | 21903 ± 64 | 5632 ± 190 | 6790 ± 0 |
| 178 | 5'-CTGTC$_2$GTTCTC-X-CTCTTGC$_2$TGTC-5' | 284 ± 2 | 2271 ± 22 | 2086 ± 0 |
| 172 | 5'-TCG$_1$TCG$_1$TTCTG-X-GTCTTG$_1$CTG$_1$CT-5' | 27183 ± 88 | 6859 ± 38 | 7543 ± 39 |
| 180 | 5'-TCG$_2$TCG$_2$TTCTG-X-GTCTTG$_2$CTG$_2$CT-5' | 774 ± 32 | 4632 ± 35 | 5335 ± 27 |
| 181 | 5'-TC$_1$GTC$_1$GTTCTG-X-GTCTTGC$_1$TGC$_1$T-5' | 25260 ± 2311 | 3678 ± 32 | 3010 ± 60 |
| 182 | 5'-TC$_2$GTC$_2$GTTCTG-X-GTCTTGC$_2$TGC$_2$T-5' | 28228 ± 2202 | 3993 ± 42 | 2793 ± 15 |

TABLE 24A-continued

Immunomer Structure and Immunostimulatory Activity in Human Dendritic Cell Assay for Donor 1 (24 hs)

| (Oligo No.) SEQ ID NO. | Sequences and Modification (5'-3') | IFN-α (pg/ml) 10 µg/ml DN1 | IL-6 (pg/ml) 10 µg/ml DN1 | TNF-α (pg/ml) 10 µg/ml DN1 |
|---|---|---|---|---|
| 183 | 5'-TC$_3$GTC$_3$GTTCTG-X-GTCTTGC$_3$TGC$_3$T-5' | 19735 ± 423 | 3905 ± 5 | 2510 ± 3 |
| 185 | 5'-TG$_1$CTG$_1$CTTG-X-GTTCG$_1$TCG$_1$T-5' | 302 ± 2 | 1394 ± 123 | 1426 ± 23 |
| media | | 321 ± 2 | 891 ± 0 | 1595 ± 0 |

TABLE 24B

Immunomer Structure and Immunostimulatory Activity in Human Dendritic Cell Assay for Donor 2 (24 hs)

| (Oligo No.) SEQ ID NO. | Sequences and Modification (5'-3') | IFN-α (pg/ml) 10 µg/ml DN2 | TNF-α (pg/ml) 10 µg/ml DN2 | IL-6 (pg/ml) 10 µg/ml DN2 |
|---|---|---|---|---|
| 26 | 5'-TCTGTCG$_1$TTCT-X-TCTTG$_1$CTGTCT-5' | 1372 ± 126 | 1942 ± 11 | 804 ± 15 |
| 170 | 5'-TCTGTC$_1$GTTCT-X-TCTTGC$_1$TGTCT-5' | 4097 ± 292 | 2671 ± 13 | 835 ± 14 |
| 172 | 5'-TCG$_1$TCG$_1$TTCTG-X-GTCTTG$_1$CTG$_1$CT-5' | 10952 ± 208 | 828 ± 14 | 1094 ± 18 |
| 180 | 5'-TCG$_2$TCG$_2$TTCTG-X-GTCTTG$_2$CTG$_2$CT-5' | 5669 ± 367 | 2868 ± 133 | 4734 ± 19 |
| 181 | 5'-TC$_1$GTC$_1$GTTCTG-X-GTCTTGC$_1$TGC$_1$T-5' | 3860 ± 180 | 1760 ± 14 | 845 ± 12 |
| 182 | 5'-TC$_2$GTC$_2$GTTCTG-X-GTCTTGC$_2$TGC$_2$T-5' | 3093 ± 127 | 2006 ± 70 | 582 ± 2 |
| 183 | 5'-TC$_3$GTC$_3$GTTCTG-X-GTCTTGC$_3$TGC$_3$T-5' | 0 ± 0 | 1406 ± 18 | 466 ± 0 |
| 185 | 5'-TG$_1$CTG$_1$CTTG-X-GTTCG$_1$TCG$_1$T-5' | 0 ± 0 | 803 ± 17 | 436 ± 3 |
| media | | 0 ± 0 | 0 ± 0 | 0 ± 0 |

TABLE 24C

Immunomer Structure and Immunostimulatory Activity in Human Dendritic Cell Assay For Donor 3 (24 hs)

| (Oligo No.) SEQ ID NO. | Sequences and Modification (5'-3') | IFN-α (pg/ml) 10 µg/ml DN3 | TNF-α (pg/ml) 10 µg/ml DN3 | IL-6 (pg/ml) 10 µg/ml DN3 |
|---|---|---|---|---|
| 26 | 5'-TCTGTCG$_1$TTCT-X-TCTTG$_1$CTGTCT-5' | 0 ± 0 | 2101 ± 26 | 804 ± 15 |
| 170 | 5'-TCTGTC$_1$GTTCT-X-TCTTGC$_1$TGTCT-5' | 2151 ± 28 | 3810 ± 5 | 835 ± 14 |
| 172 | 5'-TCG$_1$TCG$_1$TTCTG-X-GTCTTG$_1$CTG$_1$CT-5' | 4977 ± 2 | 678 ± 13 | 1094 ± 18 |
| 180 | 5'-TCG$_2$TCG$_2$TTCTG-X-GTCTTG$_2$CTG$_2$CT-5' | 2951 ± 39 | 2085 ± 60 | 4734 ± 19 |
| 181 | 5'-TC$_1$GTC$_1$GTTCTG-X-GTCTTGC$_1$TGC$_1$T-5' | 5075 ± 154 | 1787 ± 14 | 845 ± 12 |
| 182 | 5'-TC$_2$GTC$_2$GTTCTG-X-GTCTTGC$_2$TGC$_2$T-5' | 3203 ± 5 | 2069 ± 15 | 582 ± 2 |
| 183 | 5'-TC$_3$GTC$_3$GTTCTG-X-GTCTTGC$_3$TGC$_3$T-5' | 0 ± 0 | 1936 ± 13 | 466 ± 0 |
| 185 | 5'-TG$_1$CTG$_1$CTTG-X-GTTCG$_1$TCG$_1$T-5' | 0 ± 0 | 846 ± 12 | 605 ± 8 |
| media | | 0 ± 0 | 0 ± 0 | 0 ± 0 |

TABLE 24D

Immunomer Structure and Immunostimulatory Activity in Human Dendritic Cell Assay for Donor 4 (24 hs)

| (Oligo No.) SEQ ID NO. | Sequences and Modification (5'-3') | IL-6 (pg/ml) 10 μg/ml DN4 | TNF-α (pg/ml) 10 μg/ml DN4 |
|---|---|---|---|
| 26 | 5'-TCTGTCG$_1$TTCT-X-TCTTG$_1$CTGTCT-5' | 1144 ± 182 | 411 ± 93 |
| 173 | 5'-TCTGTCG$_2$TTCT-X-TCTTG$_2$CTGTCT-5' | 3386 ± 28 | 2936 ± 5 |
| 170 | 5'-TCTGTC$_1$GTTCT-X-TCTTGC$_1$TGTCT-5' | 4267 ± 18 | 1832 ± 68 |
| 175 | 5'-TCTGTC$_3$GTTCT-X-TCTTGC$_3$TGTCT-5' | 2254 ± 41 | 1173 ± 23 |
| 171 | 5'-CTGTCG2TTCTC-X-CTCTTG2CTGTC-5' | 5532 ± 3 | 3494 ± 142 |
| 178 | 5'-CTGTC$_2$GTTCTC-X-CTCTTGC$_2$TGTC-5' | 1430 ± 17 | 1127 ± 55 |
| 172 | 5'-TCG$_1$TCG$_1$TTCTG-X-GTCTTG$_1$CTG$_1$CT-5' | 6564 ± 77 | 2932 ± 52 |
| 180 | 5'-TCG$_2$TCG$_2$TTCTG-X-GTCTTG$_2$CTG$_2$CT-5' | 5360 ± 147 | 1584 ± 24 |
| 181 | 5'-TC$_1$GTC$_1$GTTCTG-X-GTCTTGC$_1$TGC$_1$T-5' | 3507 ± 118 | 2326 ± 60 |
| 182 | 5'-TC$_2$GTC$_2$GTTCTG-X-GTCTTGC$_2$TGC$_2$T-5' | 2273 ± 92 | 1297 ± 36 |
| 183 | 5'-TC$_3$GTC$_3$GTTCTG-X-GTCTTGC$_3$TGC$_3$T-5' | 2352 ± 78 | 1237 ± 28 |
| 185 | 5'-TG$_1$CTG$_1$CTTG-X-GTTCG$_1$TCG$_1$T-5' | 1396 ± 20 | 1000 ± 0 |
| media | | 695 ± 19 | 651 ± 3 |

Example 20

Human peripheral blood mononuclear cells (PBMCs) were isolated from peripheral blood of healthy volunteers and prepared as discussed above in Example 4.). Tables 25A-25D show an average±SD of IL-6 and IL-10 for Donors 1-4 with Immunomers at a concentrations of 10.0 μg/mL.

TABLE 25A

Immunomer Structure and Immunostimulatory Activity in Human PBMC Assay for Donor 1 (48 hs)

| (Oligo No.) SEQ ID NO. | Sequences and Modification (5'-3') | IL-6 (pg/ml) 10 μg/ml DN1 | IL-10 (pg/ml) 10 μg/ml DN2 |
|---|---|---|---|
| 26 | 5'-TCTGTCG$_1$TTCT-X-TCTTG$_1$CTGTCT-5' | 483 ± 2.6 | 49.9 ± 1.3 |
| 173 | 5'-TCTGTCG$_2$TTCT-X-TCTTG$_2$CTGTCT-5' | 722 ± 9.1 | 50.3 ± 1.6 |
| 170 | 5'-TCTGTC$_1$GTTCT-X-TCTTGC$_1$TGTCT-5' | 502 ± 14.2 | 46.9 ± 1.9 |
| 175 | 5'-TCTGTC$_3$GTTCT-X-TCTTGC$_3$TGTCT-5' | 400 ± 2.8 | 39.4 ± 0.5 |
| 171 | 5'-CTGTCG$_2$TTCTC-X-CTCTTG$_2$CTGTC-5' | 466 ± 17.8 | 47.6 ± 0.4 |
| 178 | 5'-CTGTC$_2$GTTCTC-X-CTCTTGC$_2$TGTC-5' | 194 ± 3.5 | 13.6 ± 0.1 |
| 172 | 5'-TCG$_1$TCG$_1$TTCTG-X-GTCTTG$_1$CTG$_1$CT-5' | 994 ± 12.2 | 57.5 ± 0.1 |
| 180 | 5'-TCG$_2$TCG$_2$TTCTG-X-GTCTTG$_2$CTG$_2$CT-5' | 652 ± 5 | 57.1 ± 7.9 |
| 181 | 5'-TC$_1$GTC$_1$GTTCTG-X-GTCTTGC$_1$TGC$_1$T-5' | 370 ± 1.9 | 37.6 ± 6.1 |
| 182 | 5'-TC$_2$GTC$_2$GTTCTG-X-GTCTTGC$_2$TGC$_2$T-5' | 416 ± 2.7 | 28.9 ± 0.7 |
| 183 | 5'-TC$_3$GTC$_3$GTTCTG-X-GTCTTGC$_3$TGC$_3$T-5' | 323 ± 5.9 | 29.7 ± 0.3 |

TABLE 25A-continued

Immunomer Structure and Immunostimulatory Activity in Human PBMC Assay for Donor 1 (48 hs)

| (Oligo No.) SEQ ID NO. | Sequences and Modification (5'-3') | IL-6 (pg/ml) 10 µg/ml DN1 | IL-10 (pg/ml) 10 µg/ml DN2 |
|---|---|---|---|
| 185 | 5'-TG$_1$CTG$_1$CTTG-X-GTTCG$_1$TCG$_1$T-5' | 281 ± 3.1 | 30.2 ± 0.3 |
| media | | 345 ± 7.9 | 8.7 ± 0.3 |

TABLE 25B

Immunomer Structure and Immunostimulatory Activity in Human PBMC Assay for Donor 2 (48 hs)

| (Oligo No.) SEQ ID NO. | Sequences and Modification (5'-3') | IFN-γ (pg/ml) 10 µg/ml DN2 | IL-6 (pg/ml) 10 µg/ml DN2 | IL-10 (pg/ml) 10 µg/ml DN2 |
|---|---|---|---|---|
| 26 | 5'-TCTGTCG$_1$TTCT-X-TCTTG$_1$CTGTCT-5' | 7.8 ± 0.6 | 742 ± 0.8 | 175 ± 3.7 |
| 170 | 5'-TCTGTC$_1$GTTCT-X-TCTTGC$_1$TGTCT-5' | 26.6 ± 1.1 | 939 ± 34.1 | 147 ± 5.8 |
| 172 | 5'-TCG$_1$TCG$_1$TTCTG-X-GTCTTG$_1$CTG$_1$CT-5' | 29.1 ± 0.2 | 1508 ± 12.3 | 179 ± 5.3 |
| 180 | 5'-TCG$_2$TCG$_2$TTCTG-X-GTCTTG$_2$CTG$_2$CT-5' | 22.3 ± 0.3 | 1294 ± 51.2 | 397 ± 11 |
| 181 | 5'-TC$_1$GTC$_1$GTTCTG-X-GTCTTGC$_1$TGC$_1$T-5' | 3.8 ± 0.5 | 276 ± 2.6 | 58 ± 0.6 |
| 182 | 5'-TC$_2$GTC$_2$GTTCTG-X-GTCTTGC$_2$TGC$_2$T-5' | 3.6 ± 0.1 | 590 ± 3.4 | 73 ± 4.1 |
| 183 | 5'-TC$_3$GTC$_3$GTTCTG-X-GTCTTGC$_3$TGC$_3$T-5' | 1.1 ± 0.2 | 233 ± 5.2 | 62.1 ± 1.4 |
| 185 | 5'-TG$_1$CTG$_1$CTTG-X-GTTCG$_1$TCG$_1$T-5' | 3.6 ± 0.5 | 203 ± 12.3 | 34.8 ± 2.7 |
| media | | 0 ± 0 | 97.4 ± 2.7 | 3.6 ± 1.1 |

TABLE 25C

Immunomer Structure and Immunostimulatory Activity in Human PBMC Assay for Donor 3 (48 hs)

| (Oligo No.) SEQ ID NO. | Sequences and Modification (5'-3') | IFN-γ (pg/ml) 10 µg/ml DN3 | IL-6 (pg/ml) 10 µg/ml DN3 | IL-10 (pg/ml) 10 µg/ml DN3 |
|---|---|---|---|---|
| 26 | 5'-TCTGTCG$_1$TTCT-X-TCTTG$_1$CTGTCT-5' | 63.8 ± 6.3 | 642 ± 12.6 | 75.2 ± 5.2 |
| 170 | 5'-TCTGTC$_1$GTTCT-X-TCTTGC$_1$TGTCT-5' | 30.7 ± 1.1 | 569 ± 6.3 | 53.9 ± 2.2 |
| 172 | 5'-TCG$_1$TCG$_1$TTCTG-X-GTCTTG$_1$CTG$_1$CT-5' | 63.9 ± 2.7 | 783 ± 0.9 | 44.5 ± 0.3 |
| 180 | 5'-TCG$_2$TCG$_2$TTCTG-X-GTCTTG$_2$CTG$_2$CT-5' | 32.9 ± 2.4 | 570 ± 3.6 | 74 ± 1.1 |
| 181 | 5'-TC$_1$GTC$_1$GTTCTG-X-GTCTTGC$_1$TGC$_1$T-5' | 32.7 ± 4.3 | 283 ± 4.9 | 37.5 ± 0.4 |
| 182 | 5'-TC$_2$GTC$_2$GTTCTG-X-GTCTTGC$_2$TGC$_2$T-5' | 33.7 ± 1.6 | 376 ± 10.4 | 48.7 ± 0.6 |
| 183 | 5'-TC$_3$GTC$_3$GTTCTG-X-GTCTTGC$_3$TGC$_3$T-5' | 23 ± 1.4 | 355 ± 5.7 | 41.6 ± 0.2 |
| 185 | 5'-TG$_1$CTG$_1$CTTG-X-GTTCG$_1$TCG$_1$T-5' | 12.3 ± 1.2 | 57.3 ± 1.2 | 39.4 ± 1.3 |
| media | | 0 ± 0 | 25.3 ± 2.9 | 11.2 ± 0.2 |

TABLE 25D

Immunomer Structure and Immunostimulatory Activity in Human PBMC Assay for Donor 4 (48 hs)

| (Oligo No.) SEQ ID NO. | Sequences and Modification (5'-3') | IL-6 (pg/ml) 10 µg/ml DN4 | IL-10 (pg/ml) 10 µg/ml DN4 |
|---|---|---|---|
| 26 | 5'-TCTGTCG$_1$TTCT-X-TCTTG$_1$CTGTCT-5' | 316 ± 20.4 | 175 ± 0 |
| 173 | 5'-TCTGTCG$_2$TTCT-X-TCTTG$_2$CTGTCT-5' | 758 ± 61.6 | 174 ± 13.2 |
| 175 | 5'-TCTGTC$_3$GTTCT-X-TCTTGC$_3$TGTCT-5' | 228 ± 21.2 | 95 ± 3.4 |
| 171 | 5'-CTGTCG$_2$TTCTC-X-CTCTTG$_2$CTGTC-5' | 498 ± 5.9 | 197 ± 3 |
| 178 | 5'-CTGTC$_2$GTTCTC-X-CTCTTGC$_2$TGTC-5' | 63 ± 0 | 39 ± 1.1 |
| 172 | 5'-TCG$_1$TCG$_1$TTCTG-X-GTCTTG$_1$CTG$_1$CT-5' | 1318 ± 32.8 | 215 ± 0.9 |
| 180 | 5'-TCG$_2$TCG$_2$TTCTG-X-GTCTTG$_2$CTG$_2$CT-5' | 976 ± 24.9 | 251 ± 9.3 |
| 181 | 5'-TC$_1$GTC$_1$GTTCTG-X-GTCTTGC$_1$TGC$_1$T-5' | 449 ± 0.9 | 96 ± 1.4 |
| 182 | 5'-TC$_2$GTC$_2$GTTCTG-X-GTCTTGC$_2$TGC$_2$T-5' | 210 ± 4.2 | 62 ± 6.3 |
| 183 | 5'-TC$_3$GTC$_3$GTTCTG-X-GTCTTGC$_3$TGC$_3$T-5' | 237 ± 2.1 | 80 ± 3.9 |
| 185 | 5'-TG$_1$CTG$_1$CTTG-X-GTTCG$_1$TCG$_1$T-5' | 636 ± 15.5 | 107 ± 8.7 |
| media | | 76.5 ± 2.4 | 12.6 ± 0.2 |

Solely for the purposes of Tables 23A-23D, 24A-24D, and 25A-25D: Normal phase represents a phosphorothioate linkage; $G_1$=2'-deoxy-7-deazaguanosine, $G_2$=Arabinoguanosine, $C_1$=1-(2'-deoxy-β-D-ribofuranosyl)-2-oxo-7-deaza-8-methylpurine, $C_2$=Arabinocytidine, $C_3$=2'-deoxy-5-hydroxycytidine, X=Glycerol linker

EQUIVALENTS

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. An immunostimulatory oligonucleotide having the structure 5'-TCG$_1$TCG$_1$TTCTG-X-GTCTTG$_1$CTG$_1$CT-5'; wherein X is a glycerol linker and G$_1$ is 2'-deoxy-7-deazaguanosine.

2. A composition comprising the oligonucleotide according to claim 1, and further comprising an antibody, antisense oligonucleotide, protein, antigen, allergen, chemotherapeutic agent or adjuvant.

3. A composition comprising the oligonucleotide according to claim 1 and a physiologically acceptable carrier.

4. The composition according to claim 3, further comprising an antibody, antisense oligonucleotide, protein, antigen, allergen, chemotherapeutic agent or adjuvant.

5. A method for generating an immune response in a mammal, the method comprising administering to the mammal an immunostimulatory oligonucleotide having the structure 5'-TCG$_1$TCG$_1$TTCTG-X-GTCTTG$_1$CTG$_1$CT-5'; wherein X is a glycerol linker and G$_1$ is 2'-deoxy-7-deazaguanosine.

6. The method according to claim 5, wherein the route of administration is selected from the group consisting of parenteral, oral, sublingual, transdermal, topical, intranasal, aerosol, intraocular, intratracheal, intrarectal, vaginal, gene gun, dermal patch, eye drop and mouthwash.

7. The method according to claim 5, further comprising administering an antibody, antisense oligonucleotide, protein, antigen, allergen, chemotherapeutic agent or adjuvant.

* * * * *

SEQUENCE LISTING

<160> NUMBER OF SEQ ID NOS: 192

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1
gagaacgctc gacctt                                                    16

<210> SEQ ID NO 2
<211> LENGTH: 16
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 2
gagaacgctc gacctt                                                        16

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gagaacgctc gacctt                                                        16

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ctatctgacg ttctctgt                                                      18

<210> SEQ ID NO 5
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tgacgttctc tgt                                                           13

<210> SEQ ID NO 6
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tgacgttctc tgt                                                           13

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ctatctgacg ttctctgt                                                      18

<210> SEQ ID NO 8
<211> LENGTH: 18
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 8
ctatctgacg ttctctgt                                                 18

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)
<223> OTHER INFORMATION: 5OHdC

<400> SEQUENCE: 9
ctatctgang ttctctgt                                                 18

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)
<223> OTHER INFORMATION: 7-deaza-dG

<400> SEQUENCE: 10
ctatctgacn ttctctgt                                                 18

<210> SEQ ID NO 11
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)
<223> OTHER INFORMATION: 5OHdC

<400> SEQUENCE: 11
ctgangttct ctgt                                                     14

<210> SEQ ID NO 12
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: 7-deaza-dG

<400> SEQUENCE: 12
ctgacnttct ctgt                                                     14

<210> SEQ ID NO 13
<211> LENGTH: 14
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ctgacgttct ctgt                                                      14

<210> SEQ ID NO 14
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ctgacgttct ctgt                                                      14

<210> SEQ ID NO 15
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)
<223> OTHER INFORMATION: 5OHdC

<400> SEQUENCE: 15
ctgangttct ctgt                                                      14

<210> SEQ ID NO 16
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: 7-deaza-dG

<400> SEQUENCE: 16
ctgacnttct ctgt                                                      14

<210> SEQ ID NO 17
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: 1',2'-dideoxyriboside

<400> SEQUENCE: 17
nntgacgttc tctgt                                                     15

<210> SEQ ID NO 18
<211> LENGTH: 16
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 1',2'-dideoxyriboside

<400> SEQUENCE: 18
nnntgacgtt ctctgt                                                    16

<210> SEQ ID NO 19
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 1',2'-dideoxyriboside
<220> FEATURE:
<221> NAME/KEY: modified_base
<222> LOCATION: (7)
<223> OTHER INFORMATION: 5OHdC

<400> SEQUENCE: 19
nnntgangtt ctctgt                                                    16

<210> SEQ ID NO 20
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 1',2'-dideoxyriboside
<220> FEATURE:
<221> NAME/KEY: modified_base
<222> LOCATION: (8)
<223> OTHER INFORMATION: 7-deaza-dG

<400> SEQUENCE: 20
nnntgacntt ctctgt                                                    16

<210> SEQ ID NO 21
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tctgacgttc t                                                         11

<210> SEQ ID NO 22
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 1',2'-dideoxyriboside
```

```
<400> SEQUENCE: 22
nnntctgacg ttct                                                     14

<210> SEQ ID NO 23
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 1',2'-dideoxyriboside
<220> FEATURE:
<221> NAME/KEY: modified_base
<222> LOCATION: (9)
<223> OTHER INFORMATION: 5OHdC

<400> SEQUENCE: 23
nnntctgang ttct                                                     14

<210> SEQ ID NO 24
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 1',2'-dideoxyriboside
<220> FEATURE:
<221> NAME/KEY: modified_base
<222> LOCATION: (10)
<223> OTHER INFORMATION: 7-deaza-dG

<400> SEQUENCE: 24
nnntctgacn ttct                                                     14

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ctatctgtcg ttctctgt                                                 18

<210> SEQ ID NO 26
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: 7-deaza-dG

<400> SEQUENCE: 26
tctgtcgttc t                                                        11

<210> SEQ ID NO 27
```

```
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: AraG

<400> SEQUENCE: 27
tctgtcnttc t                                                          11

<210> SEQ ID NO 28
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: AraC
<220> FEATURE:
<221> NAME/KEY: modified_base
<222> LOCATION: (7)
<223> OTHER INFORMATION: AraG

<400> SEQUENCE: 28
tctgtnnttc t                                                          11

<210> SEQ ID NO 29
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: 1',2'-dideoxyriboside
<220> FEATURE:
<221> NAME/KEY: modified_base
<222> LOCATION: (9)
<223> OTHER INFORMATION: 7-deaza-dG

<400> SEQUENCE: 29
nntctgtcnt tct                                                        13

<210> SEQ ID NO 30
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: AraG

<400> SEQUENCE: 30
ctgtcnttct ctgt                                                       14

<210> SEQ ID NO 31
<211> LENGTH: 14
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)
<223> OTHER INFORMATION: AraC
<220> FEATURE:
<221> NAME/KEY: modified_base
<222> LOCATION: (6)
<223> OTHER INFORMATION: AraG

<400> SEQUENCE: 31
ctgtnnttct ctgt                                                         14

<210> SEQ ID NO 32
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: 7-deaza-dG

<400> SEQUENCE: 32
tctgacnttc t                                                            11

<210> SEQ ID NO 33
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: 1',2'-dideoxyriboside
<220> FEATURE:
<221> NAME/KEY: modified_base
<222> LOCATION: (9)
<223> OTHER INFORMATION: 7-deaza-dG

<400> SEQUENCE: 33
nntctgacnt tct                                                          13

<210> SEQ ID NO 34
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: AraG

<400> SEQUENCE: 34
tctgacnttc t                                                            11

<210> SEQ ID NO 35
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (6)
<223> OTHER INFORMATION: AraC
<220> FEATURE:
<221> NAME/KEY: modified_base
<222> LOCATION: (7)
<223> OTHER INFORMATION: AraG

<400> SEQUENCE: 35
tctgannttc t                                                              11

<210> SEQ ID NO 36
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)
<223> OTHER INFORMATION: AraC

<400> SEQUENCE: 36
ctgangttct ctgt                                                           14

<210> SEQ ID NO 37
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: AraG

<400> SEQUENCE: 37
ctgacnttct ctgt                                                           14

<210> SEQ ID NO 38
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)
<223> OTHER INFORMATION: AraC
<220> FEATURE:
<221> NAME/KEY: modified_base
<222> LOCATION: (6)
<223> OTHER INFORMATION: AraG

<400> SEQUENCE: 38
ctgannttct ctgt                                                           14

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
```

```
ctatctgacg ttctctgt                                              18
```

<210> SEQ ID NO 40
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40

```
ctgacgttct ctgt                                                  14
```

<210> SEQ ID NO 41
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41

```
tctgacgttc t                                                     11
```

<210> SEQ ID NO 42
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42

```
gacgttct                                                          8
```

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43

```
ctatctgtcg ttctctgt                                              18
```

<210> SEQ ID NO 44
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44

```
ctgtcgttct ctgt                                                  14
```

<210> SEQ ID NO 45
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45

```
ctgtcgttct ct                                                    12
```

```
<210> SEQ ID NO 46
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
tctgtcgttc t                                                              11

<210> SEQ ID NO 47
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47 gtcgttct                                                                   8

<210> SEQ ID NO 48
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48 gtcgttc                                                                    7

<210> SEQ ID NO 49
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49 gtcgtt                                                                     6

<210> SEQ ID NO 50
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50 tcgtt                                                                      5

<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ctcactttcg ttctctgt                                                       18
```

<210> SEQ ID NO 52
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
ctcactttcg ttctctgt                                                 18

<210> SEQ ID NO 53
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
ctttcgttct ctgt                                                     14

<210> SEQ ID NO 54
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
ctttcgttct ct                                                       12

<210> SEQ ID NO 55
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55 ttcgttct                                                             8

<210> SEQ ID NO 56
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56 tcgttct                                                              7

<210> SEQ ID NO 57
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: 5OHdC

<400> SEQUENCE: 57

```
tctttngttc t                                              11

<210> SEQ ID NO 58
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: 7-deaza-dG

<400> SEQUENCE: 58
tctttcnttc t                                              11

<210> SEQ ID NO 59
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 5OHdC

<400> SEQUENCE: 59 ttngttct                                                   8

<210> SEQ ID NO 60
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)
<223> OTHER INFORMATION: 7-deaza-dG

<400> SEQUENCE: 60 ttcnttct                                                   8

<210> SEQ ID NO 61
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: 5OHdC

<400> SEQUENCE: 61
tctgtngttc t                                              11

<210> SEQ ID NO 62
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (7)
<223> OTHER INFORMATION: 7-deaza-dG

<400> SEQUENCE: 62
tctgtcnttc t                                                            11

<210> SEQ ID NO 63
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 5OHdC

<400> SEQUENCE: 63 gtngttct                                                                 8

<210> SEQ ID NO 64
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)
<223> OTHER INFORMATION: 7-deaza-dG

<400> SEQUENCE: 64 gtcnttct                                                                 8

<210> SEQ ID NO 65
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)
<223> OTHER INFORMATION: 5OHdC

<400> SEQUENCE: 65
ctatctgang ttctctgt                                                     18

<210> SEQ ID NO 66
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)
<223> OTHER INFORMATION: 7-deaza-dG

<400> SEQUENCE: 66
ctatctgacn ttctctgt                                                     18

<210> SEQ ID NO 67
```

```
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)
<223> OTHER INFORMATION: 5OHdC

<400> SEQUENCE: 67
ctgangttct ctgt                                                        14

<210> SEQ ID NO 68
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: 7-deaza-dG

<400> SEQUENCE: 68
ctgacnttct ctgt                                                        14

<210> SEQ ID NO 69
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: 5OHdC

<400> SEQUENCE: 69
tctgangttc t                                                           11

<210> SEQ ID NO 70
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: 7-deaza-dG

<400> SEQUENCE: 70
tctgacnttc t                                                           11

<210> SEQ ID NO 71
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 5OHdC
```

```
<400> SEQUENCE: 71 gangttct                                                                    8

<210> SEQ ID NO 72
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)
<223> OTHER INFORMATION: 7-deaza-dG

<400> SEQUENCE: 72 gacnttct                                                                    8

<210> SEQ ID NO 73
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
ctgacgttct                                                                 10

<210> SEQ ID NO 74
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
ctgacgttct                                                                 10

<210> SEQ ID NO 75
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
ctgacgttct                                                                 10

<210> SEQ ID NO 76
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
ctgacgttct                                                                 10

<210> SEQ ID NO 77
<211> LENGTH: 10
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 77
ctgacgttct                                                              10

<210> SEQ ID NO 78
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
ctgacgttct                                                              10

<210> SEQ ID NO 79
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
ctgacgttct                                                              10

<210> SEQ ID NO 80
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
ctgacgttct                                                              10

<210> SEQ ID NO 81
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
ctgacgttct                                                              10

<210> SEQ ID NO 82
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
ctgacgttct                                                              10

<210> SEQ ID NO 83
<211> LENGTH: 10
<212> TYPE: DNA
<213> ORGANISM: Artificial Sequence
<220> FEATURE:
<223> OTHER INFORMATION: Description of Artificial Sequence: Synthetic

```
oligonucleotide

<400> SEQUENCE: 83
ctgacgttct                                                                      10

<210> SEQ ID NO 84
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
ctgacgttct ctgt                                                                 14

<210> SEQ ID NO 85
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
ctgacgttct ctgt                                                                 14

<210> SEQ ID NO 86
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
ctgtcgttct ctgtctgtcg ttctctgt                                                  28

<210> SEQ ID NO 87
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
ctgtcgttct ctgt                                                                 14

<210> SEQ ID NO 88
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: 2,-OMe-ribonucleoside
<220> FEATURE:
<221> NAME/KEY: modified_base
<222> LOCATION: (16)..(17)
<223> OTHER INFORMATION: 2,-OMe-ribonucleoside

<400> SEQUENCE: 88
nntgtcgttc tctgtnntgt cgttctctgt                                                30
```

```
<210> SEQ ID NO 89
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
tccatgacgt tcctgatgc                                                  19

<210> SEQ ID NO 90
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
tccatgacgt tcctgatgc                                                  19

<210> SEQ ID NO 91
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
tccatgacgt tcctgatgc                                                  19

<210> SEQ ID NO 92
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
tccatgacgt tcctgatgc                                                  19

<210> SEQ ID NO 93
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
tccatgacgt tcctgatgc                                                  19

<210> SEQ ID NO 94
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
tccatgacgt tcctgatgc                                                  19
```

```
<210> SEQ ID NO 95
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
tccatgacgt tcctgatgc                                                19

<210> SEQ ID NO 96
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
tccatgacgt tcctgatgc                                                19

<210> SEQ ID NO 97
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
tccatgacgt tcctgatgc                                                19

<210> SEQ ID NO 98
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
tccatgacgt tcctgatgc                                                19

<210> SEQ ID NO 99
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
tccatgacgt tcctgatgc                                                19

<210> SEQ ID NO 100
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
tccatgacgt tcctgatgc                                                19

<210> SEQ ID NO 101
```

```
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
tccatgacgt tcctgatgc                                                19

<210> SEQ ID NO 102
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
cctactagcg ttctcatc                                                 18

<210> SEQ ID NO 103

<400> SEQUENCE: 103

000

<210> SEQ ID NO 104
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
gcgttctcat c                                                        11

<210> SEQ ID NO 105
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
tagcgttctc atc                                                      13

<210> SEQ ID NO 106
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
tagcgttctc atc                                                      13

<210> SEQ ID NO 107
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 107
tactagcgtt ctcatc                                               16

<210> SEQ ID NO 108
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
cctactagcg t                                                    11

<210> SEQ ID NO 109
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
cctactagcg ttc                                                  13

<210> SEQ ID NO 110
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
cctactagcg ttc                                                  13

<210> SEQ ID NO 111
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
ctagcgttct catc                                                 14

<210> SEQ ID NO 112
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
cctactagcg ttc                                                  13

<210> SEQ ID NO 113
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
```

-continued

```
ctagcgttct catc                                         14

<210> SEQ ID NO 114
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
cctactagcg ttc                                          13

<210> SEQ ID NO 115
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
tgacgttctc tgt                                          13

<210> SEQ ID NO 116
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
ctgacgttct ctgt                                         14

<210> SEQ ID NO 117
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
cgttctctgt                                              10

<210> SEQ ID NO 118
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
gacgttctct gt                                           12

<210> SEQ ID NO 119
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
```
ctgacgttct ctgt                                    14

<210> SEQ ID NO 120
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
tgacgttctc tgt                                     13

<210> SEQ ID NO 121
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
tgacgttctc tgt                                     13

<210> SEQ ID NO 122
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
tgacgttctc tgt                                     13

<210> SEQ ID NO 123
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
tgacgttctc tgt                                     13

<210> SEQ ID NO 124
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
tgacgttctc tgt                                     13

<210> SEQ ID NO 125
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
tgacgttctc tgt                                     13

```
<210> SEQ ID NO 126
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
ctgacgttct ctgt                                                         14

<210> SEQ ID NO 127
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
tgacgttctc tgt                                                          13

<210> SEQ ID NO 128
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
tgacgttctc tgt                                                          13

<210> SEQ ID NO 129
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
tgacgttctc tgt                                                          13

<210> SEQ ID NO 130
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
ctgacgttct ctgt                                                         14

<210> SEQ ID NO 131
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
tgacgttctc tgt                                                          13
```

```
<210> SEQ ID NO 132
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
tgacgttctc tgt                                                          13

<210> SEQ ID NO 133
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
tgacgttctc tgt                                                          13

<210> SEQ ID NO 134
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
ctgacgttct ctgt                                                         14

<210> SEQ ID NO 135
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
tgacgttctc tgt                                                          13

<210> SEQ ID NO 136
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
tgacgttctc tgt                                                          13

<210> SEQ ID NO 137
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
ctgacgttct ctgt                                                         14
```

```
<210> SEQ ID NO 138
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
ctatctgacg ttc                                                          13

<210> SEQ ID NO 139
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
ctgacgttct ctgt                                                         14

<210> SEQ ID NO 140
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
ctatctgacg ttc                                                          13

<210> SEQ ID NO 141
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
cgttctctgt                                                              10

<210> SEQ ID NO 142
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
acgttctctg t                                                            11

<210> SEQ ID NO 143
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
gacgttctct gt                                                           12

<210> SEQ ID NO 144
```

```
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
tgacgttctc tgt                                                          13

<210> SEQ ID NO 145
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
ctgacgttct ctgt                                                         14

<210> SEQ ID NO 146
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
ctatctgacg                                                              10

<210> SEQ ID NO 147
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
ctatctgacg t                                                            11

<210> SEQ ID NO 148
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
ctatctgacg tt                                                           12

<210> SEQ ID NO 149
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
ctatctgacg ttc                                                          13

<210> SEQ ID NO 150
<211> LENGTH: 10
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
cgttctctgt                                                              10

<210> SEQ ID NO 151
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
acgttctctg t                                                            11

<210> SEQ ID NO 152
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
ctgacgttct ctgt                                                         14

<210> SEQ ID NO 153
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
ctatctgacg t                                                            11

<210> SEQ ID NO 154
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
ctatctgacg ttc                                                          13

<210> SEQ ID NO 155
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
ctatctgacg ttctctgt                                                     18

<210> SEQ ID NO 156
<211> LENGTH: 14
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 156
ctgacgttct ctgt                                                     14

<210> SEQ ID NO 157
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
ctgacgttct ctgt                                                     14

<210> SEQ ID NO 158
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
tctgacgttc t                                                        11

<210> SEQ ID NO 159
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
tctgtcgttc t                                                        11

<210> SEQ ID NO 160
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160 tcgttg                                                               6

<210> SEQ ID NO 161
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161 tcgttg                                                               6

<210> SEQ ID NO 162
<211> LENGTH: 6
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 162 tcgttg                                                                   6

<210> SEQ ID NO 163
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163 tcgtt                                                                    5

<210> SEQ ID NO 164
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164 acgttg                                                                   6

<210> SEQ ID NO 165
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165 gcgttg                                                                   6

<210> SEQ ID NO 166
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166 ccgttg                                                                   6

<210> SEQ ID NO 167
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167 gtcgtt                                                                   6

<210> SEQ ID NO 168
<211> LENGTH: 6
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 168 tgtcgt                                                                    6

<210> SEQ ID NO 169
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169 tcgttg                                                                    6

<210> SEQ ID NO 170
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: 1-(2'-deoxy-beta-D-ribofuranosyl)-2-oxo-7-
      deaza-8-methylpurine

<400> SEQUENCE: 170
tctgtngttc t                                                             11

<210> SEQ ID NO 171
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: AraG

<400> SEQUENCE: 171
ctgtcnttct c                                                             11

<210> SEQ ID NO 172
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 7-deaza-dG
<220> FEATURE:
<221> NAME/KEY: modified_base
<222> LOCATION: (6)
<223> OTHER INFORMATION: 7-deaza-dG

<400> SEQUENCE: 172
tcntcnttct g                                                             11

<210> SEQ ID NO 173
<211> LENGTH: 11

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: AraG

<400> SEQUENCE: 173
tctgtcnttc t                                                              11

<210> SEQ ID NO 174
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: AraC

<400> SEQUENCE: 174
tctgtngttc t                                                              11

<210> SEQ ID NO 175
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: 2'-deoxy-5-hydroxycytidine

<400> SEQUENCE: 175
tctgtngttc t                                                              11

<210> SEQ ID NO 176
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: 7-deaza-dG

<400> SEQUENCE: 176
ctgtcnttct c                                                              11

<210> SEQ ID NO 177
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)
<223> OTHER INFORMATION: 1-(2'-deoxy-beta-D-ribofuranosyl)-2-oxo-7-
      deaza-8-methylpurine
```

-continued

```
<400> SEQUENCE: 177
ctgtngttct c                                                              11

<210> SEQ ID NO 178
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)
<223> OTHER INFORMATION: AraC

<400> SEQUENCE: 178
ctgtngttct c                                                              11

<210> SEQ ID NO 179
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)
<223> OTHER INFORMATION: 2'-deoxy-5-hydroxycytidine

<400> SEQUENCE: 179
ctgtngttct c                                                              11

<210> SEQ ID NO 180
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: AraG
<220> FEATURE:
<221> NAME/KEY: modified_base
<222> LOCATION: (6)
<223> OTHER INFORMATION: AraG

<400> SEQUENCE: 180
tcntcnttct g                                                              11

<210> SEQ ID NO 181
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)
<223> OTHER INFORMATION: 1-(2'-deoxy-beta-D-ribofuranosyl)-2-oxo-7-
      deaza-8-methylpurine
<220> FEATURE:
<221> NAME/KEY: modified_base
<222> LOCATION: (5)
<223> OTHER INFORMATION: 1-(2'-deoxy-beta-D-ribofuranosyl)-2-oxo-7-
      deaza-8-methylpurine

<400> SEQUENCE: 181
```

```
tngtngttct g                                                        11

<210> SEQ ID NO 182
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)
<223> OTHER INFORMATION: AraC
<220> FEATURE:
<221> NAME/KEY: modified_base
<222> LOCATION: (5)
<223> OTHER INFORMATION: AraC

<400> SEQUENCE: 182
tngtngttct g                                                        11

<210> SEQ ID NO 183
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)
<223> OTHER INFORMATION: 2'-deoxy-5-hydroxycytidine
<220> FEATURE:
<221> NAME/KEY: modified_base
<222> LOCATION: (5)
<223> OTHER INFORMATION: 2'-deoxy-5-hydroxycytidine

<400> SEQUENCE: 183
tngtngttct g                                                        11

<210> SEQ ID NO 184
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)
<223> OTHER INFORMATION: May be 2'-deoxycytidine,
      1-(2'-deoxy-beta-D-ribfuranosyl)-2-oxo-7-deaza-8-
      methylpurine, AraC, or 2'-deoxy-5-hydroxycytidine
<220> FEATURE:
<221> NAME/KEY: modified_base
<222> LOCATION: (3)
<223> OTHER INFORMATION: May be 2'-deoxyguanosine, 7-deaza-dG or AraG
<220> FEATURE:
<221> NAME/KEY: modified_base
<222> LOCATION: (5)
<223> OTHER INFORMATION: May be 2'-deoxycytidine,
      1-(2'-deoxy-beta-D-ribfuranosyl)-2-oxo-7-deaza-8-
      methylpurine, AraC, or 2'-deoxy-5-hydroxycytidine
<220> FEATURE:
<221> NAME/KEY: modified_base
<222> LOCATION: (6)
<223> OTHER INFORMATION: May be 2'-deoxyguanosine, 7-deaza-dG or AraG

<400> SEQUENCE: 184
tnntnnttct g                                                        11
```

```
<210> SEQ ID NO 185
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)
<223> OTHER INFORMATION: 7-deaza-dG
<220> FEATURE:
<221> NAME/KEY: modified_base
<222> LOCATION: (5)
<223> OTHER INFORMATION: 7-deaza-dG

<400> SEQUENCE: 185 tnctncttg                                                            9

<210> SEQ ID NO 186
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
ccatgacgtt cctgatg                                                  17

<210> SEQ ID NO 187
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
tccatgacgt tcctgatg                                                 18

<210> SEQ ID NO 188
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
ccatgacgtt cctgatgc                                                 18

<210> SEQ ID NO 189
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)
<223> OTHER INFORMATION: 7-deaza-dG

<400> SEQUENCE: 189
ctatctgang ttctctgt                                                 18

<210> SEQ ID NO 190
<211> LENGTH: 18
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)
<223> OTHER INFORMATION: 7-deaza-dG

<400> SEQUENCE: 190
ctatctgtng ttctctgt                                                    18

<210> SEQ ID NO 191
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: 7-deaza-dG

<400> SEQUENCE: 191
tctgangttc t                                                           11

<210> SEQ ID NO 192
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: 7-deaza-dG

<400> SEQUENCE: 192
tctgtngttc t                                                           11
```